United States Patent [19]

Oku et al.

[11] Patent Number: 4,889,851
[45] Date of Patent: Dec. 26, 1989

[54] BENZOTHIADIAZINE COMPOUNDS, AND PHARMACEUTICAL COMPOSITION COMPRISING THE SAME

[75] Inventors: Teruo Oku; Eishiro Todo; Chiyoshi Kasahara; Katsuya Nakamura; Hiroshi Kayakiri, Masashi Hashimoto, all of Ibaraki, Japan

[73] Assignee: Fujisawa Pharmaceutical Co, Ltd., Osaka, Japan

[21] Appl. No.: 116,913

[22] Filed: Nov. 5, 1987

[30] Foreign Application Priority Data

Nov. 21, 1986 [GB] United Kingdom ................ 8627857
Jun. 22, 1987 [GB] United Kingdom ................ 8714598
Sep. 2, 1987 [GB] United Kingdom ................ 8720659

[51] Int. Cl.$^4$ .................... C07D 285/24; A61K 31/54
[52] U.S. Cl. .................................... 514/223.2; 544/12
[58] Field of Search ........................ 544/12; 514/223.2

[56] References Cited

U.S. PATENT DOCUMENTS

| 3,267,096 | 8/1966 | Hayao | 544/12 |
| 3,287,362 | 11/1966 | Hurner et al. | 544/12 |
| 3,296,070 | 1/1967 | Topliss et al. | 544/12 |
| 3,892,738 | 7/1975 | Novello | 544/12 |

FOREIGN PATENT DOCUMENTS 1067028 10/1959 Fed. Rep. of Germany .
460032 7/1968 Switzerland .

OTHER PUBLICATIONS

Il Farmaco, Edizione Scientifica, vol. 34, No. 3, Mar. 1979, pp. 199–210.
Chemical Abstracts, vol. 67, No. 1, Jul. 3, 1967, p. 156, Abstract No. 1740m.
Chemical Abstracts 53 18962 (1959); 56 2462–2463 (1962); 59 644 (1963); 64 19614 (1966) and 68 39602b (1968).

*Primary Examiner*—John M. Ford
*Attorney, Agent, or Firm*—Oblon, Spivak, McClelland, Maier & Neustadt

[57] ABSTRACT

A compound of the formula:

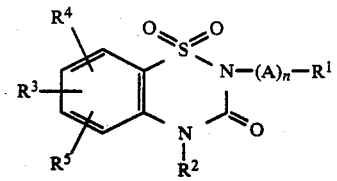

wherein R' is phenyl, phenyl which is substituted with halogen, lower alkyl, lower alkoxy, halo lower alkyl, lower alkylamino, lower alkylthio, phenoxy, carboxy, lower alkoxycarbonyl, carboxy lower alkyl, lower alkoxycarbonyl, lower alkyl, cyclo lower alkyl; lower alkyl which is substituted with carboxy or lower alkoxycarbonyl; or pyrimidinyl, pyridyl or pyridyl which is substituted with lower alkyl;

A is lower alkylene;
n is an integer of 0 or 1;
$R^2$ is lower alkyl;
$R^3$ is hydrogen; hydroxy; halogen; halo lower alkyl; lower alkyl; lower alkylamino; lower alkanoyl amino; lower alkanoyl lower alkylamino; lower alkoxy; lower alkoxy which is substituted with phenyl, phthalimido, pyranyl, amino, carboxy, lower alkoxycarbonyl, cyclo lower alkyl or cyclo lower alkyl which is substituted with amino lower alkyl or lower alkoxycarbonylamino lower alkyl; or cyclo lower alkyloxy or cyclo lower alkyloxy which is substituted with carboxy or lower alkoxycarbonyl;
$R^4$ is hydrogen or halogen, and
$R^5$ is hydrogen or halogen, with the proviso
$R^1$ is phenyl substituted with lower alkoxy, lower alkylamino, lower alkylthio, phenoxy, carboxy, lower alkoxycarbonyl, carboxyl lower alkyl or lower alkoxycarbonyl lower alkyl; lower alkyl or lower alkyl substituted with carboxy or lower alkoxycarbonyl; pyrimidinyl; pyridyl or pyridyl substituted with lower alkyl, when $R^3$ is hydrogen or halogen, or a pharmaceutically acceptable salt thereof. The compounds and compositions containing the same are useful in the treatment of bone diseases.

7 Claims, No Drawings

BENZOTHIADIAZINE COMPOUNDS, AND PHARMACEUTICAL COMPOSITION COMPRISING THE SAME

This invention relates to new benzothiadiazine compounds and pharmaceutically acceptable salts thereof.

More particularly, it relates to new benzothiadiazine compounds and pharmaceutically acceptable salts thereof which have, for example, inhibitory activities on bone resorption, to processes for the preparation thereof, to a pharmaceutical composition comprising the same and to a method for the treatment of bone diseases characterized by abnormal bone metabolism in human being or animals.

One object of this invention is to provide new and useful benzothiadiazine compounds and pharmaceutically acceptable salts thereof which possess, for example, inhibitory activities on bone resorption.

Another object of this invention is to provide processes for the preparation of said benzothiadiazine compounds or salts thereof.

A further object of this invention is to provide a pharmaceutical composition comprising, as an active ingredient, said benzothiadiazine compounds and ceutically acceptable salts thereof.

Still further object of this invention is to provide a therapeutical method for the treatment of bone diseases characterized by abnormal bone metabolism such as osteoporosis, Paget's bone disease, osteolysis, hypercalcemia of malignancy and rheumatoid arthritis.

The object benzothiadiazine compounds of this invention are new and can be represented by the following general formula [I]:

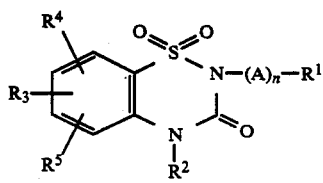

wherein $R^1$ is phenyl which may be substituted with halogen, lower alkyl, lower alkoxy, halo(lower)alkyl, lower alkylamino, lower alkylthio, aryloxy, carboxy, esterified carboxy, carboxy(lower)-alkyl or esterified carboxy(lower)alkyl; cyclo(lower)alkyl;

lower alkyl which may be substituted with carboxy or esterified carboxy; or heterocyclic group which may be substituted with lower alkyl;

A is lower alkylene, n is an integer $R^2$ is hydrogen or lower alkyl, $R^3$ is hydrogen; hydroxy; halo(lower)alkyl; lower alkyl; lower alkylamino; acylamino; acyl(lower)alkylamino; lower alkoxy which may be substituted with aryl, protected amino, heterocyclic group-,amino, carboxy, esterified carboxy, or cyclo(lower)alkyl which may be substituted with amino(lower)alkyl or protected amino-(lower)alkyl; or cyclo(lower)alkyloxy which may be substituted with carboxy or esterified carboxy;

$R^4$ is hydrogen or halogen, and $R^5$ is hydrogen or halogen, provided that $R^1$ is phenyl substituted with lower alkoxy, lower alkylamino, lower alkylthio, aryloxy, carboxy, esterified carboxy, carboxy(lower)-alkyl or esterified carboxy(lower)alkyl; lower alkyl substituted with carboxy or esterified carboxy; or heterocyclic group substituted with lower alkyl, when $R^3$ is hydrogen or halogen.

The object compound [I] of the present invention can be prepared by the following processes.

PROCESS 1

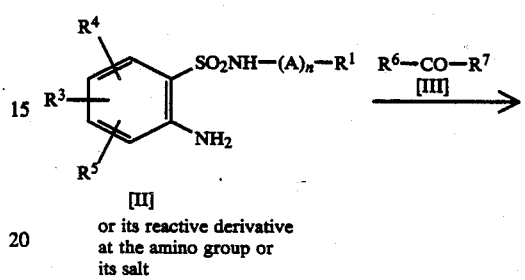

[II]
or its reactive derivative
at the amino group or
its salt

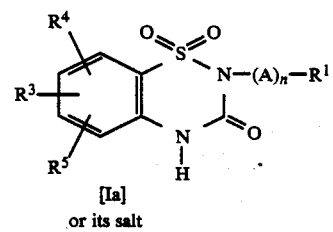

[Ia]
or its salt

PROCESS 2

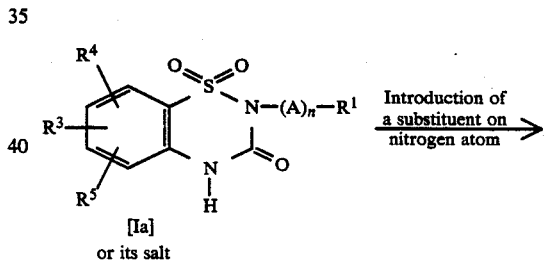

[Ia]
or its salt

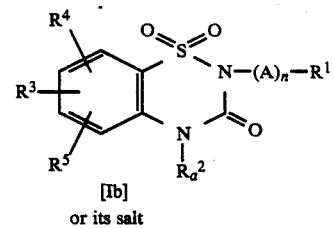

[Ib]
or its salt

PROCESS 3

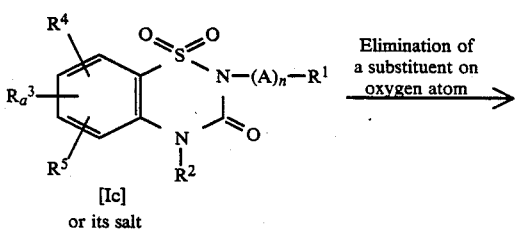

[Ic]
or its salt

-continued
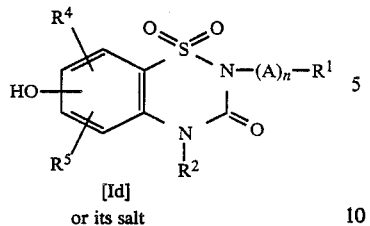
[Id] or its salt
-continued
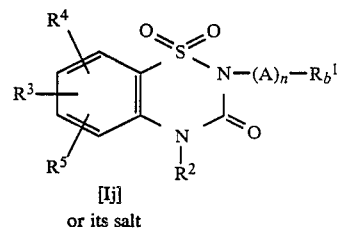
[Ij] or its salt
PROCESS 4
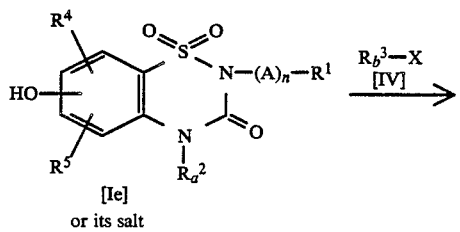
[Ie] or its salt
[If] or its salt
PROCESS 7
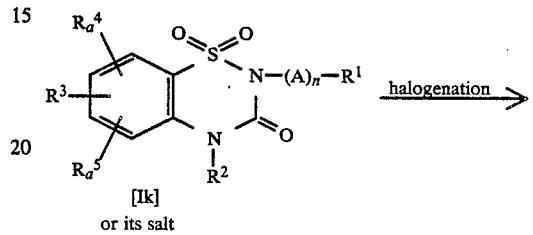
[Ik] or its salt
[Il] or its salt
PROCESS 5
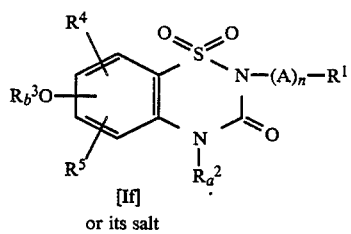
[Ig] or its salt
[Ih] or its salt
PROCESS 8
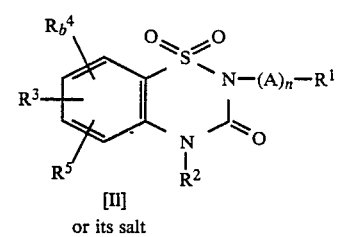
[Im] or its salt
[In] or its salt
PROCESS 6
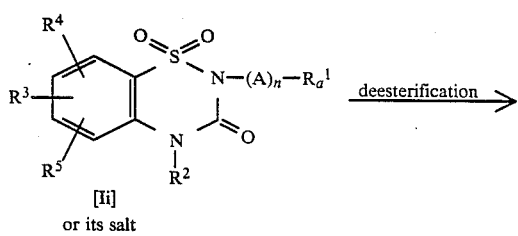
[Ii] or its salt
PROCESS 9
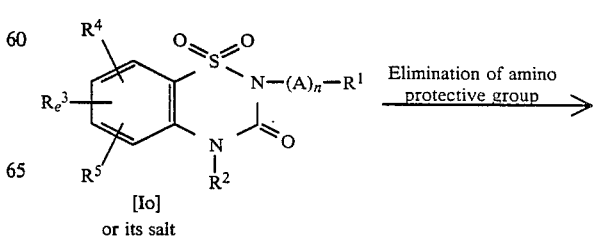
[Io] or its salt

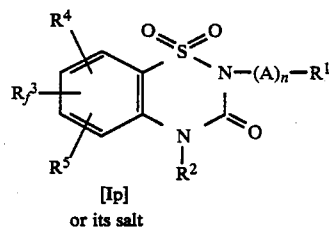

[Ip] or its salt

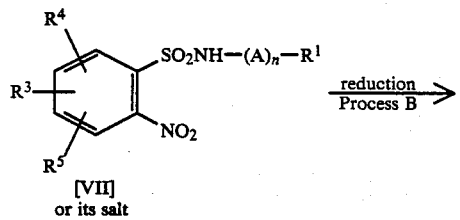

[VII] or its salt

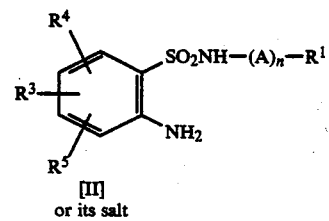

[II] or its salt wherein $R^1$, $R^2$, $R^3$, $R^4$, $R^5$, A and n are each as defined above, $R_a^1$ is phenyl substituted with esterified carboxy(lower)alkyl or esterified carboxy; or esterified carboxy(lower)alkyl;

$R_b^1$ is phenyl substituted with carboxy(lower) alkyl or carboxy; or carboxy(lower)alkyl;

$R_a^2$ is lower alkyl, $R_a^3$ is lower alkoxy which may be substituted with aryl, cyclo(lower)alkyl, carboxy or esterified carboxy; or cyclo(lower)alkyloxy which may be substituted with carboxy or esterified carboxy;

$R_b^3$ is lower alkyl which may be substituted with aryl, protected amino, heterocyclic group, carboxy, esterified carboxy or cyclo(lower)-alkyl which may be substituted with protected amino(lower)alkyl; or cyclo(lower)alkyl which may be substituted with carboxy or esterified carboxy;

$R_c^3$ is esterified carboxy(lower)alkoxy which may be substituted with cyclo(lower)alkyl;or, esterified carboxycyclo(lower)alkyloxy;

$R_d^3$ is carboxy(lower)alkoxy which may be substituted with cyclo(lower)alkyl;or carboxycyclo(lower)alkyloxy;

$R_e^3$ is acyl(lower)alkylamino or lower alkoxy substituted with protected amino or cyclo(lower)alkyl substituted with protected amino(lower)alkyl, $R_f^3$ is lower alkylamino or lower alkoxy substituted with amino or cyclo(lower)alkyl substituted with amino(lower)alkyl, $R_a^4$ is hydrogen, $R_b^4$ is halogen, $R_a^5$ is hydrogen, $R^6$ and $R^7$ are each halogen, lower alkoxy or imidazolyl, $R^8$ and $R^9$ are each lower alkyl, and X is leaving group.

Among the starting compounds in the above processes, the compound [II] is novel and can be prepared by the processes as illustrated in the following.

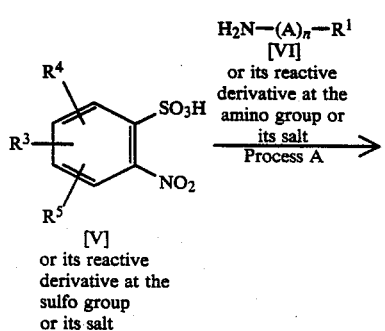

[V] or its reactive derivative at the sulfo group or its salt

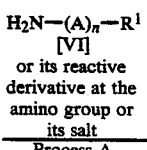

wherein $R^1$, $R^3$, $R^4$, $R^5$, A and n are each as defined above.

In the above and subsequent description of the present specification, suitable example and illustrations for the various definitions to be included within the scope of the invention are explained in detail as follows:

The term "lower" is intended to mean 1 to 6 carbon atom (s) unless otherwise indicated.

The number of the substituent on phenyl for $R^1$ may be 1 to 3, preferably 1 or 2.

Suitable examples of the lower alkyl may be a straight or branched one such as methyl, ethyl, propyl, isopropyl, butyl, isobutyl, tert-butyl, pentyl, hexyl or the like.

Suitable example of "lower alkyl" moiety in the terms "halo(lower)alkyl", "lower alkylamino", "lower alkylthio", "amino(lower)alkyl", "protected amino(lower)alkyl", "acyl(lower)alkylamino", "carboxy(lower)alkyl" and "esterified carboxy(lower)alkyl" can be referred to the ones as exemplified above.

Suitable example of "halo(lower)alkyl" may include "monohalo(lower)alkyl" [e.g. chloromethyl, bromomethyl fluoromethyl, etc.], "dihalo(lower)alkyl" [e.g. dichloromethyl, dibromomethyl, difluoromethyl, etc.] and "trihalo(lower)alkyl" [e.g. trichloromethyl, tribromomethyl, trifluoromethyl, trifluoroethyl, etc.] and the like.

Suitable example of "lower alkylamino" may include "mono(lower)alkylamino" [e.g. methylamino, ethylamino, isopropylamino, hexylamino, etc.] and "di(lower)alkylamino" [e.g. dimethylamino, diethylamino, dipropylamino, methylethylamino, etc.] and the like.

Suitable examples of the lower alkylene group may be a straight or branched one such as methylene, ethylene, trimethylene, tetramethylene, pentamethylene, hexamethylene, propylene, methylethylene, ethylethylene, propylethylene, isopropylethylene, methylpentamethylene or the like.

Suitable examples of "halogen" may include chlorine, bromine, iodine and fluorine.

Suitable examples of "lower alkoxy" and "lower alkoxy" moiety in the terms "carboxy(lower)alkoxy" and "esterified carboxy(lower)alkoxy" may include methoxy, ethoxy, propoxy, isopropoxy, butoxy, isoutoxy, t-butoxy, pentyloxy, hexyloxy and the like.

Suitable examples of "aryl" may include phenyl, tolyl, xylyl, cunenyl, naphthyl, and the like.

Suitable example of "aryloxy" may include phenoxy tolyloxy, naphthyloxy, and the like.

Suitable examples of "cyclo(lower)alkyl" may include cyclopropyl, cyclobutyl, cyclopentyl, cyclohexyl, and the like.

Suitable example of "cyclo(lower)alkyl" moiety in the terms "cyclo(lower)alkyloxy", "carboxycyclo(lower)alkyloxy" and "esterified carboxycyclo(lower)alkyloxy" can be referred to the ones as exemplified above.

Suitable examples of "acyl" moiety in the terms "acylamino" and "acyl(lower)alkylamino" may include lower alkanoyl [e.g. formyl, acetyl, propionyl, valeryl, pivaloyl, etc.], lower alkoxycarbonyl [e.g. methoxycarbonyl, ethoxycarbonyl, propoxycarbonyl, isopropoxycarbonyl, butoxycarbonyl, t-butoxycarbonyl, pentyloxycarbonyl, hexyloxycarbonyl, etc.], lower alkanesulfonyl [e.g. methanesulfonyl, ethanesulfonyl, propanesulfonyl, butanesulfonyl, pentanesulfonyl, hexanesulfonyl, etc.], aroyl [e.g. benzoyl, naphthoyl, etc.] which may be substituted with halogen as exemplified above, arylcarbamoyl [e.g. phenylcarbamoyl, tolylcarbamoyl, etc.] which may be substituted with halogen as mentioned above, and the like.

Suitable "leaving group" may include hydroxy and acid residue, and suitable example of "acid residue" may be halogen (e.g. chlorine, bromine, iodine, or fluorine), sulfonyloxy (e.g. methanesulfonyloxy, benzenesulfonyloxy, toluenesulfonyloxy, etc.) or the like, in which the preferred example may be halogen.

Suitable "protected amino" and "protected amino" moiety in the term "protected amino(lower)alkyl" may include acylamino wherein "acyl" moiety can be referred to the ones as mentioned above, phthalimido phosphonoamino, ar(lower)alkylamino such as benzylamino, phenethylamino, tritylamino; and the like.

Suitable "esterified carboxy" and "esterified carboxy" moiety in the terms "esterified carboxy(lower)alkyl", "esterified carboxy(lower)alkoxy" and "esterified carboxycyclo(lower)alkyloxy" may include lower alkoxycarbonyl (e.g. methoxycarbonyl, ethoxycarbonyl, propoxycarbonyl, isopropoxycarbonyl, butoxycarbonyl, tert-butoxycarbonyl, etc.), mono(or di or tri)-phenyl(lower)alkoxycarbonyl which may have a nitro group (e.g. benzyloxycarbonyl, 4-nitrobenzyloxycarbonyl, phenethyloxycarbonyl, benzhydryloxycarbonyl, trityloxycarbonyl, etc.), and the like, in which more preferred example may be $C_1$-$C_4$ alkoxycarbonyl and the most preferred one may be ethoxycarbonyl.

Suitable "heterocyclic group" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6 membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.; saturated 3 to 6-membered heteromonocyclic group containing 1 to 4 nitrogen atom (e.g. pyrrolidinyl, imidazolyidinyl, piperidino, piperazinyl, etc.); unsaturated condensed heterocyclic group containing 1 5 nitrogen atoms for example indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.), etc.; saturated 3 to 6-membered heteromonocyclic group containing 1 to 2 oxygen atoms and 1 to 3 nitrogen atoms (e.g., morpholinyl, etc.); unsaturated condensed heterocyclic group containing 1 to 2 oxygen atoms and 1 to 3 nitrogen atoms (e.g., benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.), etc.; saturated 3 to 6-membered heteromonocyclic group containing 1 to 2 sulfur atoms and 1 to 3 nitrogen atoms (e.g., thiazolidinyl, etc.); unsaturated condensed heterocyclic group containing 1 to 2 sulfur atoms and 1 to 3 nitrogen atoms (e.g., benzothiazolyl, benzothiadiazolyl, etc.) and the like. Said "heterocyclic group" may have 1 to 4 substitutents such as lower alkyl as exemplified above.

Suitable pharmaceutically acceptable salts of the object compound [I] are conventional non-toxic salts and include an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, ornithine salt, etc.], a salt with base such as alkali metal salt [e.g. sodium salt, potassium salt, etc.],an alkaline earth metal salt [e.g. calcium salt, magnesium salt, etc.] or the like, and the like.

In this respect, it is to be noted that the compounds [Ia] to [Ip] are included within the scope of the compound [I], and accordingly the suitable salts of these compounds [Ia] to [Ip] are to be referred to those as exemplified for the object compound [I] in the above.

It is also to be noted that each of the object compound [I] and the starting compound [II] include one or more stereoisomers due to asymmetric carbon atom in the molecule, and all of such isomers of the compound [I] and [II] are included within the scope of this invention.

The processes for preparing the object compound [I] or salts thereof are explained in detail in the following.

PROCESS 1

The object compound [Ia] or its salt can be prepared by reacting the compound [II] or its reactive derivative at the amino group or its salt with the compound [III].

Suitable reactive derivatives at the amino group of the compound [II] include conventional ones used in amidation, for example, Schiff's base type imino or its tautomeric enamine type isomer formed by reaction of the compound [II] with a carbonyl compound, a silyl derivative formed by reaction of the compound [II] with a silyl compound such as trimethylsilylacetamide, bis(trimethylsilyl)acetamide or the like, a derivative formed by reaction of the compound [II] with phosphorus trichloride or phosgene, and the like.

This reaction is usually carried out in a conventional solvent such as tetrahydrofuran, dioxane, methylene chloride, chloroform, benzene, dimethylformamide, dimethyl sulfoxide or any other organic solvent which does not adversely influence the reaction.

The reaction temperature is not critical, and the reaction can be carried out under cooling to heating.

PROCESS 2

The compound [Ib] or its salt can be prepared by subjecting the compound [Ia] or its salt to introduction reaction of a substituent on nitrogen atom.

The present introduction reaction can be carried out by reacting the compound [Ia] or its salt with a compound of the formula: $R_a^2$-X wherein $R_a^2$ and X are each as defined above.

The present introduction reaction can also be carried out by reacting the compound [Ia] or its salt with di(lower)alkyl sulfate [e.g. dimethyl sulfate, diethyl sulfate, etc.], diazo(lower)alkane [e.g. diazomethane, diazoethane, etc.], and the like.

The reaction using di(lower)alkyl sulfate or a compound of the formula: $R_a^2$-X is usually carried out in a solvent such as water, acetone, ethanol, ether, N,N-dimethylformamide or any other solvent which does not adversely influence the reaction. The present reaction is preferably carried out in the presence of a base such as an inorganic base or an organic base.

Suitable organic or inorganic base may be alkali metal hydride [e.g. sodium hydride, potassium hydride, etc.], alkaline earth metal hydride [e.g. calcium hydride, magnesium hydride, etc.], alkali metal hydroxide [e.g. sodium hydroxide, potassium hydroxide, etc.], alkali metal carbonate [e.g. sodium carbonate, potassium carbonate, etc.], alkali metal bicarbonate [e.g. sodium bicarbonate, potassium bicarbonate, etc.], alkali metal fluoride [e.g. potassium fluoride, cesium fluoride, etc.], alkali metal alkoxide [e.g. sodium methoxide, sodium ethoxide, potassium tert-butoxide, etc.], trialkylamine [e.g. trimethylamine, triethylamine, etc.], picoline, 1,5-diazabicyclo[4,3,0]non-5-ene, 1,4-diazabicyclo[2,2,2]octane, 1,5-diazabicyclo[5,4,0]-undecene-5 or the like.

The reaction temperature is not critical and the reaction is usually carried out under cooling to heating.

The reaction using diazoalkane is usually carried out in a solvent such as ether, tetrahydrofuran or the like. The reaction temperature is not critical and the reaction is usually carried out under cooling or at ambient temperature.

PROCESS 3

The object compound [Id] or its salt can be prepared by subjecting the compound [Ic] or its salt to elimination reaction of a substituent on oxygen atom.

The reaction is preferably carried out in the presence of a Lewis acid, for example, boron halide (e.g. boron trichloride, boron tribromide, etc.), hydrohalogenic acid (e.g. hydrobromic acid, hydroiodic acid etc.) and the like.

The reaction is usually carried out without a solvent or in a solvent which does not adversely influence the reaction such as chloroform, methylene chloride, carbon tetrachloride or the like.

The reaction temperature is not critical, and the reaction is usually carried out under cooling to heating.

PROCESS 4

The object compound [If] or its salt can be prepared by reacting the compound [Ie] or its salt with the compound [IV].

The present reaction is preferably carried out in the presence of a base such as an inorganic base or an organic base as explained in Process 2.

This reaction is usually carried out in a conventional solvent such as water, methanol, ethanol, propanol, tetralin, tetrahydrofuran, dioxane, chloroform, toluene, N,N-dimethylformamide, dimethylsulfoxide or any other organic solvent which does not adversely influence the reaction.

The reaction temperature is not critical, and the reaction is usually carried out under cooling, at ambient temperature or under heating.

PROCESS 5

The object compound [Ih] or its salt can be prepared by subjecting the compound [Ig] or its salt to deesterification reaction.

The deesterification reaction can be carried out by conventional hydrolysis, reduction and the like.

The hydrolysis reaction can be carried out in the presence of a base or an acid, and suitable base may be the inorganic base as explained in Process 2. Suitable acid may be an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.).

This reaction is usually carried out in a conventional solvent which does not adversely influence the reaction such as water, acetone, dichloromethane, methanol, ethanol, propanol, pyridine, N,N-dimethylformamide, tetrahydrofuran, etc., or a mixture thereof, and further in case that the base or acid to be used in this reaction is in liquid, it can also be used as a solvent.

The reaction temperature is not critical and the reaction is usually carried out under from cooling to heating. In the present reaction, in case that $R^1$ is phenyl substituted with esterified carboxy or esterified carboxy(lower)alkyl or esterified carboxy(lower)alkyl, it may be converted during the reaction to phenyl substituted with carboxy or carboxy(lower)alkyl; or carboxy(lower)alkyl, respectively. This case is also included within the scope of the present reaction.

PROCESS 6

The object compound [Ij] or its salt can be prepared by subjecting the compound [Ii] or its salt to deesterification reaction.

This reaction may be carried out in substantially the same manner as Process 5, and therefore the reaction mode [e.g. hydrolysis, reduction, etc.] and reaction conditions [e.g. reducing agent, base, acid, solvent, reaction temperature, etc.] of this reaction are to be referred to those as explained in Process 5. In the present reaction, in case that R3 is lower alkoxy substituted with esterified carboxy or cyclo(lower)-alkyloxy substituted with esterified carboxy, it may be converted during the reaction to lower alkoxy substituted with carboxy or cyclo(lower)alkyloxy substituted with carboxy, respectively. This case is also included within the scope of the present reaction.

PROCESS 7

The object compound [Il] or its salt can be prepared by halogenating the compound [Ik] or its salt.

Suitable halogenating agent of this reaction may include conventional ones for example, halogen [e.g. chlorine, bromine, iodine, etc.], sulfuryl halide [e.g.

sulfuryl chloride, sulfuryl bromide, etc.], N-halosuccinimide [e.g. N-chlorosuccinimide, N-bromosuccinimide, etc.], pyridinium hydrohalide perhalide [e.g. pyridinium hydrobromide perbromide, pyridinium hydrochloride perchloride, etc.], quarternary ammonium perhalide [e.g. phenyltrimethylammonium perbromide, etc.], ω-trihaloacetophenone [e.g. ω-tribromoacetophenone, etc.], cupric or potassium bromide, selenium oxychloride, or the like. These halogenating agents may be selected according to the kind of the starting compound [Ik] to be used.

This reaction is usually carried out in a conventional solvent such as chloroform, methylene chloride, carbon tetrachloride, acetic acid, a mixture of hydrogen halide [e.g. hydrogen bromide, hydrogen chloride, etc.] and acetic acid, water, dimethylformamide or the like.

The reaction temperature is not critical, and the reaction is usually carried out under cooling, at ambient temperature or under warming or heating.

PROCESS 8

The compound [In] or its salt can be prepared by subjecting the compound [Im] or its salt to alkylation reaction.

The alkylating agent to be used in the present alkylation reaction may include di(lower)alkyl sulfate [e.g. dimethyl sulfate, diethyl sulfate, etc.], diazo(lower)alkane [e.g. diazomethane, diazoethane, etc.], lower alkyl halide [e.g. methyl iodide, ethyl iodide, etc.], lower alkyl sulfonate [e.g. methyl p-toluene-sulfonate, etc.], and the like.

The reaction using di(lower)alkyl sulfate, lower alkyl halide or lower alkyl sulfonate is usually carried out in a solvent such as water, acetone, ethanol, ether tetrahydrofuran dimethylformamide or any other solvent which does not adversely influence the reaction. The present reaction is preferably carried out in the presence of a base such as an inorganic base or an organic base as mentioned for Process 2. The reaction temperature is not critical and the reaction is usually carried out under cooling to heating around boiling point of the solvent.

The reaction using diazoalkane is usually carried out in a solvent such as ether, tetrahydrofuran or the like. The reaction temperature is not critical and the reaction is usually carried out under cooling or at ambient temperature. The compound [In] or its salt can also be prepared by reacting the compound [Im] or its salt with alkane aldehyde in the presence of reducing agent. Suitable alkane aldehyde may include formaldehyde, acetaldehyde, propionaldehyde and the like. Suitable reducing agent can be referred to the ones as mentioned for Process B. This reaction is usually carried out in a conventional solvent such as water, methanol, ethanol, propanol, tetralin, tetrahydrofuran, acetonitrile, dioxane, chloroform, toluene, dimethylformamide, dimethylsulfoxide or any other organic solvent which does not adversely influence the reaction.

The reaction temperature is not critical, and the reaction is usually carried out at ambient temperature or under cooling or warming.

PROCESS 9

The object compound [Ip] or its salt thereof can be prepared by subjecting the compound [Io] or its salt to elimination reaction of amino protective group.

The present elimination reaction is carried out in accordance with a conventional method such as hydrolysis; reduction; a method by reacting the compound [Io] wherein the protective group is acyl group with iminohalogenating agent and then with iminoetherifying agent, and, if necessary, subjecting the resulting compound to hydrolysis; or the like. The hydrolysis may include a method using an acid or base or hydrazine and the like. These methods may be selected depending on the kind of the protective groups to be eliminated.

Among these methods, hydrolysis using an acid is one of the common and preferable method for eliminating the protective group such as substituted or unsubstituted alkoxycarbonyl (e.g. t-pentyloxycarbonyl, t-butoxycarbonyl, etc.), alkanoyl (e.g. formyl, acetyl, etc.), cycloalkoxycarbonyl, substituted or unsubstituted aralkoxycarbonyl (e.g. benzyloxycarbonyl, substituted benzyloxycarbonyl, etc.), ar(lower)alkyl (e.g. benzyl, trityl, etc.) or the like.

Suitable acid may include an organic or an inorganic acid, for example, formic acid, trifluoroacetic acid, benzenesulfonic acid, p-toluenesulfonic acid, hydrochloric acid and the like, and preferable acid is, for example, formic acid, trifluoroacetic acid, hydrochloric acid, etc. The acid suitable for the reaction can be selected according to the kind of protective group to be eliminated. When the elimination reaction is conducted with the acid, it can be carried out in the presence or absence of a solvent. Suitable solvent may include a conventional organic solvent (e.g., methanol, ethanol, tetrahydrofuran, etc.), water or a mixture thereof. When trifluoroacetic acid is used, the elimination reaction may preferably be carried out in the presence of anisole.

The hydrolysis using hydrazine is commonly applied for eliminating the protective group, for example, succinyl or phthaloyl.

The hydrolysis with a base is preferably applied for eliminating acyl agroup, for example, haloalkanoyl (e.g. dichloroacetyl, trifluoroacetyl, etc.) etc. Suitable base may include, for example, an inorganic base and an organic base as exemplified above for Process 2. The hydrolysis using a base is often carried out in water, a conventional organic solvent or a mixture thereof.

Among the protective group, the acyl group can be generally eliminated by hydrolysis as mentioned above or by the other conventional hydrolysis. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, substituted benzyloxycarbonyl etc.), 2-pyridylmethoxycarbonyl, etc. Suitable reduction may include, for example, reduction with an alkali metal borohydride (e.g. sodium borohydride, etc.) and the like.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The processes for preparing the starting compound [II] or its salt are explained in detail in the following.

PROCESS A

The compound [VII] or its salt can be prepared by reacting the compound [V] or its reactive derivative at the sulfo group or its salt with the compound [VI] or its reactive derivative at the amino group or its salt.

Suitable example of the reactive derivative at the sulfo group may include conventional ones such as acid halide (e.g. acid chloride, acid bromide, etc.) acid anhydride, activated ester or amide, and the like.

Suitable example of the reactive derivative at the amino group can be referred to the ones as mentioned above for Process 1.

The reaction can preferably be conducted in the presence of an organic or inorganic base as explained in Process 2.

The reaction is usually carried out in a solvent. A suitable solvent to be used may be water, alcohol [e.g. methanol, ethanol, propanol, etc.], acetonitrile or any other conventional organic solvent such as diethyl ether, dioxane, tetrahydrofuran, etc. or a mixture thereof. Additionally, the aforementioned liquid bases can also be used as a solvent.

The reaction is preferably carried out under cooling to heating.

PROCESS B

The compound [II] or its salt can be prepared by reducing the compound [VII] or its salt.

The reaction may include chemical reduction and catalytic reduction, which are carried out in a conventional manner.

Suitable reducing agents to be used in chemical reduction are a metal [e.g. tin, zinc, iron, etc.], a combination of such metal and/or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], a combination of such metal and/or metallic compound and base [e.g. ammonia, ammonium chloride, sodium hydroxide, etc.], a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, bonane, diborane, etc.], a phosphorus compound [e.g. phosphorus trichloride, phosphorus tribromide, triphenylphosphine, triethylphosphine, etc.] and the like.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.], or the like.

The reduction is usually carried out in a solvent. A suitable solvent to be used may be water, alcohol [e.g. methanol, ethanol, propanol, etc.], acetonitrile or any other conventional organic solvent such as diethyl ether, dioxane, tetrahydrofuran, etc. or a mixture thereof.

The reaction is preferably carried out under warming to heating.

The compounds thus obtained by Processes 1 to 9 and Processes A and B may be converted into aforesaid pharmaceutically acceptable salts thereof according to a conventional manner.

The object compound [I] and pharmaceutically acceptable salts thereof possess, for example, strong inhibitory activities on bone resorption, and useful for therapeutical treatment of bone diseases characterized by abnormal bone metabolism such as osteoporosis, Paget's bone disease, osteolysis, hypercalcemia of malignancy and rheumatoid arthritis.

For therapeutic purpose, the compounds [I] and pharmaceutically acceptable salts thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compounds [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating said bone diseases. In general, amounts between 0.1 mg/body and about 1,000 mg/body may be administered per day.

In order to illustrate the usefulness of the object compound [I], the pharmacological test data of same representative compounds of the compound [I] are shown in the following.

TEST METHOD

Neonatal calvaria were dissected aseptically from 1–2 day old rat (Wistar), washed in Dulbecco's modified eagle's medium and divided along the sagittal suture. The calvaria halves were pooled and randomized in the different groups. The calvaria halves were cultured separately as free-floating bones in multi-well dishes containing a 2 ml of Dubecco's modified eagle's medium, with 10% heat-inactivated (56° C. for 1 hr) fetal calf serum. Treatment of hPTH(1-34)($1 \times 10^{-8}$M) and the Test Compound ($1 \times 10^{-5}$M) was begun at zero time. All incubations were performed at 37° C., under an atmosphere of 95% air and 5% $CO_2$ for 6 days. Bone resorption was determined by measuring the accumulation of calcium in the medium at 6 days. The concentration of total calcium in culture medium was measured by OCPC method with a spectrophotometer (Hitachi model U-3200, Tokyo, Japan).

As comparative data, similar tests were conducted using culture medium with hPTH ($1 \times 10^{-8}$M) only, and culture medium without both hPTH and Test Compound.

Test results were represented in terms of percentage of inhibition calculated by the following formula:

$$\text{Inhibition (\%)} = \frac{C_P - C_D}{C_P - C_O} \times 100$$

$C_D$ the concentration of total calcium in culture medium treated with both hPTH and Test Compound $C_O$ the concentration of total calcium in control culture medium without both hPTH and Test Compound $C_P$ the concentration of total calcium in culture medium treated with hPTH only

TEST COMPOUNDS (a) 2-(4-Chlorophenyl)-6-isopropoxy-4-methyl-2H-1,2,4-benzothiadiazine-3(4H)-one 1,1-dioxide (Example 4 and Example 6-(22))

(b) 2-(4-Chlorophenyl)-4-methyl-6-(2-methylpropoxy)-2H-1,2,4-benzothiadiazine-3(4H)-one 1,1-dioxide (Example 6-(24) and Example 10)

(c) 2-(4-Chlorophenyl)-4-methyl-6-cyclohexylmethoxy-2H-1,2,4-benzothiadiazine-3(4H)-one 1,1-dioxide (Example 6-(25) and Example 11)

(d) 2-(4-Trifluoromethylphenyl)-4-methyl-6-isopropoxy-2H-1,2,4-benzothiadiazine-3(4H)-one 1,1-dioxide (Example 6-(23) and Example 9)

(e) 2-(4-Chlorophenyl)-6-(1-carboxyethoxy)-4-methyl-2H-1,2,4-benzothiadiazine-3(4H)-one 1,1-dioxide (R,S mixture) (Example 6-(29), Example 14, Example 15-(5))

(f) (1R)-(+)-2-(4-Chlorophenyl)-6-(1-carboxyethoxy)-4-methyl-2H-1,2,4-benzothiadiazine-3(4H)-one 1,1-dioxide
(Example 6-(44), Example 15-(12), Example 16-(5))

TEST RESULTS

| Test Results: | |
|---|---|
| Test Compound | Inhibition (%) |
| (a) | 79.7 |
| (b) | 56.1 |
| (c) | 62.5 |
| (d) | 52.9 |
| (e) | 67.9 |
| (f) | 50.2 |

The following Preparations and Examples are given for the purpose of illustrating the present invention in more detail.

PREPARATION 1

To a mixture of 4-chloroaniline (14.51 g) and 4-methoxy-2-nitrobenzenesulfonyl chloride (28.54 g) was added dropwise aqueous sodium hydroxide solution (0.7 N, 162 ml) over a period of 30 minutes at 70° C. After addition, the mixture was stirred for 30 minutes at the same temperature. The colled mixture was diluted with aqueous 1N-hydrochloric acid. The separated oil was extracted with ethyl acetate. The extract was dried over magnesium sulfate and concentrated under reduced pressure. The yellow solid was triturated with n-hexame and collected by filtration to yield 4-methoxy-2-nitro-N-(4-chlorophenyl) benzenesulfonamide (37,23 g).

mp: 56°-60° C.

IR (CHCl$_3$): 1600, 1540,, 1490, 1170 cm$^{-1}$.

NMR (CDCl$_3$, δ): 3.92 (3H, s), 6.90–7.80 (7H, m), 7.70 (1H, d, J=9Hz).

PREPARATION 2

To a mixture of 4-methoxy-2-nitro-N-(4-chlorophenyl)benzenesulfonamide (37.2 g) and ammonium chloride (75.4 g) in a mixture of methanol (400 ml) and water (400 ml) was added iron (76.4 g) in small portions over a period of one and half hours at 100° C. The reaction mixture was refluxed for 8 hours and the hot mixture was filtrated. The filtrated cake was washed with hot methanol. The combined filtrates were evaporated under reduced pressure and the residue was extracted three times with ethyl acetate. The extracts were washed with water, dried, and concentrated to give crude product, which was purified by silica gel column-chromatography (elution by methylene chloride) to yield 2-amino-4-methoxy-N-(4-chlorophenyl) benzenesulfonamide (25.77 g).

mp: 94°–96° C.

IR (Nujol): 3400, 3300, 1600, 1580, 1500 cm$^{-1}$.

NMR (CDCl$_3$, δ): 3.76 (3H, s), 4.90 (2H, br s), 6.20–6.30 (2H, m), 6.90–7.50 (6H, m).

PREPARATION 3

In a similar manner to that of Preparation 1, there were obtained the following compounds.

(1) 4-Methoxy-2-nitro-N-(P-tolyl)benzenesulfonamide mp: 100°–101° C.

IR (Nujol): 3320, 1600, 1540, 1390, 1240, 1150 cm$^{-1}$.

NMR (CDCl$_3$, δ): 2.28 (3H, s), 3.90 (3H, s), 6.90–7.40 (6H, m), 7.70 (1H, d, J=9Hz).

(2) 4-Methoxy-2-nitro-N-(phenyl)benzenesulfonamide mp: 126°–28° C.

IR (Nujol): 3400, 3300, 1600, 1540, 1460, 1170 cm$^{-1}$.

NMR (CDCl$_3$, δ): 3.90 (3H, s), 6.96 (1H, dd, J=2 Hz and 9 Hz), 7.10–7.40 (5H, m), 7.72 (1H, d, J=9 Hz).

(3) 4-Methoxy-2-nitro-N-(4-trifluoromethylphenyl)-benzenesulfonamide mp: 108°–110° C.

IR (Nujol): 1600, 1540, 1460, 1330, 1170, 1120 cm$^{-1}$.

NMR (CDCl$_3$, δ): 3.90 (3H, s), 7.02 (1H, dd, J=2 Hz and 9 Hz), 7.20–7.70 (5H, m), 7.83 (1H, d, J=9 Hz).

(4) 4-Methoxy-2-nitro-N-(3,4-dichlorophenyl)benzene-sulfonamide mp: 146°–50° C.

IR (Nujol): 3300, 1610, 1550, 1470, 1380 cm$^{-1}$.

NMR (CDCl$_3$, δ): 3.90 (3H, s), 6.90–7.40 (5H, m), 7.30 (1H, d, J=9 Hz).

(5) 4-Methoxy-2-nitro-N-(4-fluorophenyl)benzenesulfonamide mp: 988°–100° C.

IR (Nujol): 3350, 1600, 1530, 1380, 1240, 1170 cm$^{-1}$.

NMR (DMSO-d$_6$, δ): 3.85 (3H, s), 7.00–7.20 (4H, m), 7.30 (1H, dd, J=2 Hz and 9 Hz), 7.55 (1H, d, J=2 Hz), 7.82 (1H, d, J=9 Hz), 10.5 (1H, br s).

(6) 4-Isopropoxy-2-nitro-N-(4-methoxyphenyl)benzenesulfonamide

IR (CHCl$_3$): 1600, 1540, 1510, 1390, 1240, 1160 cm$^{-1}$.

NMR (CDCl$_3$, δ): 1.37 (6H, d, J=6 Hz)<3.77 (3H, s), 4.62 (1H, m), 6.78 (1H, d, J=9 Hz), 6.90 (1H, dd, J=2 Hz and 9 Hz), 7.00–7.30 (4H, m), 7.62 (1H, d, J=9 Hz).

(7) 2-Nitro-N-(4-chlorophenyl)benzenesulfonamide mp: 120°–123° C.

IR (Nujol): 3300, 1600, 1550, 1490, 1460, 1340, 1170, 1160 cm$^{-1}$.

NMR (CDCl$_3$, δ): 7.00–7.40 (4H, m), 7.50–7.95 (4H, m).

(8) 4-Chloro-2-nitro-N-(4-chlorophenyl)benzenesulfonamide mp: 116°–118° C.

IR (Nujol): 1540, 1490, 1460, 1360, 1240, 1180, 1170 cm$^{-1}$.

NMR (CDCl$_3$, δ): 7.10–7.33 (4H,m), 7.55 (1H, dd, J=2 Hz and 9 Hz), 7.75 (1H, d, J=9 Hz). 7.83 (1H, d, J=2 Hz).

(9) 4-Methoxy-2-nitro-N-(2-chlorophenyl)benzenesulfonamide mp: 94°–95° C.

IR (Nujol): 3350, 3300, 1600, 1540, 1480, 1460, 1180 cm$^{-1}$.

NMR (CDCl$_3$, δ): 3.90 (3H, s), 6.90–7.40 (5H, m), 7.60–7.90 (2H, m).

(10) 4-Methoxy-2-nitro-N-(3-chlorophenyl)benzenesulfonamide mp: 137°–38° C.

IR (Nujol): 3300, 1610, 1590, 1550, 1330, 1170 cm$^{-1}$.

NMR (CDCl$_3$, δ): 3.82 (3H, s), 7.00 (1H, dd, J=2 Hz and 9 Hz), 7.10–7.40 (5H, m), 7 89 (1H, d, J=9 Hz).

(11) 4-Isopropoxy-2-nitro-N-(4-chlorophenyl)benzenesulfonamide

IR (CDCl$_3$): 1600, 1540, 1490, 1390, 1170 cm$^{-1}$.

NMR (CDCl$_3$, δ) 1.36 (6H, d, J=6 Hz), 4.62 (1H, m), 6.92 (1H, dd, J=2 Hz and 9 Hz), 7.0–7.5 (6H, m), 7.69 (1H, d, J=9 Hz).

(12) 4-Methoxy-2-nitro-N-(4-chlorobenzyl)benzenesulfonamide mp: 110.5–111.5° C.

IR (Nujol): 3320, 1610, 1530, 1165 cm$^{-1}$.

NMR (CDCl$_3$, δ): 3.93 (3H, s), 4.25 (2H, s), 5.65 (1H, br.s), 7.05 (1H, d d, J=2.5 and 8.8 Hz), 7.18 and 7.20 (4H, ABq, J=8.8 Hz), 7.30 (1H, d, J=2.5 Hz), 7.88 (1H, d, J=8.8 Hz)

(13) 4-Methoxy-2-nitro-N-cyclohexylbenzenesulfonamide mp: 91°—93° C.

IR (Nujol): 3320, , 1330, 1155, 1050 cm$^{-1}$.

NMR (CDCl$_3$, δ): 1.05–1.4 (5H, m), 1.45–1.9 (5H, m), 3.27 (1H, br), 3.94 (3H, s), 5.13 (1H, d, J=7.3 Hz), 7.16 (1H, d d, J=2.5 and 8.8 Hz), 7.43 (1H, d, J=2.5 Hz), 8.03 (1H, d, J=8.8 Hz).

(14) 4-Isopropoxy-2-nitro-N-(2-pyridyl)benzenesulfonamide mp: 123°–125° C.

IR (Nujol): 1635, 1620, 1605, 1240, 1150 cm$^{-1}$.

NMR (DMSO-d$_6$, δ): 1.25 (6H, d, J=5.5 Hz), 4.65–4.85 (1H, m), 6.8–6.9 (1H, m), 7.10–7.17 (1H, m), 7.26 (1H, dd, J=2 Hz and 9 Hz), 7.40 (1H, d, J=2 Hz), 7.75–7.87 (1H, m), 7.9–7.98 (2H, m).

(15) 4-Methoxy-2-nitro-N-(pentyl)benzenesulfonamide mp: 48°–50° C.

IR (Nujol): 3300, 1600, 1560, 1350, 1340, 1160 cm$^{-1}$

NMR (DMSO-d$_6$, δ): 0.85 (3H, t, J=7 Hz), 1.10–1.60 6H, m), 3.05 (2H, q, J=7 Hz), 3.94 (3H, s), 5.13 (1H, bs), 7.15 (1H, dd, J=3 Hz and 9 Hz), 7.35 (1H, d, J=3 Hz), 8.04 (1H, d, J=9 Hz).

(16) 4-Acetylamino-2-nitro-N-(4-chlorophenyl)-benzenesulfonamide mp: 207°–209° C.

IR Nujol): 3370, 3230, 1695, 1590, 1250, 1170, 1155 cm$^{-1}$.

NMR (DMSO-d$_6$, δ): 2.15 (3H, s), 7.15 and 7.35 (4H, ABq, J=9.0 Hz), 7.72–7.85 (1H, m), 7.85–8.0 (1H, m), 8.17 (1H, s), 10.7 (1H, s), 10.75 (1H, s).

(17) 4-Methoxy-2-nitro-N-(4-methoxycarbonylphenyl)-benzenesulfonamide mp: 170° C. (dec.).

IR (Nujol): 3250, 1690, 1605, 1545, 1295 cm$^{-1}$.

NMR (DMSO-d$_6$, δ): 3.79 (3H, s), 3.87 (3H, s), 7.25 and 7.90 (4H, ABq, J=8.5 Hz), 7.33 (1H, dd, J=2 Hz and 9 Hz), 7.60 (1H, d, J=2.0 Hz), 7.96 (1H, d, J=9 Hz), 11.11 (1H, s).

(18) 4-Cyclohexylmethoxy-2-nitro-N-(2-pyridyl)-benzenesulfonamide mp: 164° C. (dec.).

IR (Nujol): 3140, 1640, 1610, 1560, 1155 cm$^{-1}$.

NMR (DMSO-d$_6$, δ): 0.9–1.4 (5H, m), 1.5–1.9 (6H, m), 3.89 (2H, d, J=6 Hz), 6.8–6.9 (1H, m), 7.1–7.2 (1H, m), 7.26 (1H, dd, J=2.4 Hz and 8.8 Hz), 7.43 (1H, d, J=2.4 Hz), 7.75–7.90 (1H, m), 7.9–8.0 (1H, m), 7.95 (1H, d J=8 Hz).

(19) 4-Methoxy-2-nitro-N-(4-methoxycarbonylmethylphenyl)-benzenesulfonamide mp: 93°–94° C.

IR (Nujol): 3330, 1715, 1545, 1160 cm$^{-1}$.

NMR (DMSO-d$_6$, δ): 3.33 (2H, s), 3.58 (3H, s), 3.86 (3H, s), 7.05 and 7.15 (4H, ABq, J=8.3 Hz), 7.32 (1H, d d, J=2.0 and 8.8 Hz), 7.56 (1H, d, J=2.0 Hz), 7.56 (1H, d, J=8.8 Hz), 10.52 (1H, s).

(20) 4-Methoxy-2-nitro-N-(3-ethoxycarbonylpropyl)-benzenesulfonamide mp: 55°–56° C.

IR (Nujol): 3350, 1720, 1610, 1550, 1470, 1380, 1280, 1170 cm$^{-1}$.

NMR (CDCl$_3$, δ): 1.25 (3H, t, J=7 Hz), 1.86 (2H, m), 2.39 (2H, t, J=7 Hz), 3.12 (2H, q, J=7 Hz), 4.12 (2H, q, J=7 Hz), 3.94 (3H, s), 5.33 (1H,bs), 7.15 (1H, dd, J=2 Hz and 9 Hz), 7.33 (1H, d, J=2 Hz), 8.03 (1H, d, J=9 Hz).

(21) 4-Methyl-2-nitro-N-(4-chlorophenyl)benzenesulfonamide mp: 112°–114° C.

IR (Nujol): 3350, 1600, 1550, 1490, 1430, 1380, 1360, 1340, 1170 cm$^{-1}$.

NMR (CDCl$_3$, δ) 2.48 (3H, s), 7.14 (2H, d, J=8 Hz), 7.24 (2H, d, J=8 Hz), 7.38 (1H, d, J=8 Hz), 7.67 (1H, s), 7.70 (1H, d, J=8 Hz).

(22) 4-Isopropoxy-2-nitro-N-[2-(4,6-dimethylpyridyl)]-benzenesulfonamide mp: 175°–180° C.

IR (Nujol): 1620, 1540, 1390, 1300, 1230, 1150 cm$^{-1}$.

NMR (DMSO-d$_6$, δ): 1.30 (6H, d, J=6 Hz), 2.20 (3H, s), 2.30 (3H, s), 4.80 (1H, m), J=2 Hz and 9 Hz), 7.42 (1H, d, J=2 Hz), 7.92 (1H, d, J=9 Hz).

(23) 4-Trifluoromethyl-2-nitro-N-(4-chlorophenyl)-benzenesulfonamide mp: 88°–90° C.

IR (Nujol): 3300, 1550, 1490, 1400, 1320, 1160, 1140, 1080 cm$^{-1}$.

NMR (CDCl$_3$, δ): 7.14 (2H, d, J=9 Hz), 7.26 (2H, d, J=9 Hz), 7.86 (1H, d, J=9 Hz), 7.98 (1H, d, J=9 Hz), 8.11 (1H, s).

(24) 4-Isopropoxy-2-nitro-N-(2-pyrimidinyl)-benzenesulfonamide mp: 218°–220° C.

IR (Nujol): 1610, 1580, 1440, 1380, 1350, 1240, 1110 cm$^{-1}$.

NMR (DMSO-d$_6$, δ): 1.30 (6H, d, J=6 Hz), 4.80 (1H, m), 7.05 (1H, t, J=4 Hz), 7.30 (1H, dd, J=2 Hz and 9

Hz), 7.48 (1H, d, J=2 Hz), 8.10 (1H, d, J=9 Hz), 8.50 (2H, d, J=4 Hz).

(25) 4-Methoxy-2-nitro-N-(4-phenoxyphenyl)-benzenesulfonamide
mp: 108°–109° C.
IR (Nujol): 3330, 1600, 1540, 1240, 1170 cm⁻¹.
NMR (CDCl₃, δ): 3.90 (3H, s), 6.85–7.40 (11H, m), 7.70 (1H, d, J=9 Hz).

(26) 4-Methoxy-2-nitro-N-(4-isopropylphenyl)-benzenesulfonamide
mp: 108°–109° C.
IR (Nujol): 3300, 1605, 1545, 1165 cm⁻¹.
NMR (CDCl₃, δ): 1.20 (6H, d, J=7 Hz), 2.85 (1H, m), 3.90 (3H, s), 6.97 (1H, dd, J=2 Hz and 9 Hz), 7.05–7.15 (4H, m), 7.32 (1H, d, J=2 Hz), 7.72 (1H, d, J=9 Hz).

(27) 4-Methoxy-2-nitro-N-[(3-chloro-4-methyl)-phenyl]-benzenesulfonamide
mp: 138°–139° C.
IR (Nujol): 3300, 1600, 1545, 1170 cm⁻¹.
NMR (CDCl₃, δ): 2.38 (3H, s), 3.90 (3H, s), 7.00 (1H, dd, J=2 Hz and 9 Hz), 7.05–7.15 (2H, m), 7.22 (1H, d, J=2 Hz), 7.33 (1H, d, J=2 Hz), 7.75 (1H, d, J=9 Hz).

(28) 4-Methoxy-2-nitro-N-(4-methylthiophenyl)-benzenesulfonamide
mp: 120°–121° C.
IR (Nujol): 3250, 3100, 1600, 1550, 1490, 1245, 1170 cm⁻¹.
NMR (CDCl₃, δ): 2.44 (3H, s), 3.90 (3H, s), 6.97 (1H, dd, J=2 Hz and 9 Hz), 7.12 (4H, s), 7.31 (1H, d, J=2 Hz), 7.70 (1H, d, J=9 Hz).

(29) 4-Methoxy-2-nitro-N-(4-dimethylaminophenyl)-benzenesulfonamide
mp: 127°–128° C.

IR (Nujol): 3350, 3340, 1600, 1540, 1520, 1350, 1280, 1230, 1160 cm⁻¹.
NMR (DMSO-d₆, δ): 2.82 (6H, s), 3.86 (3H, s), 6.60 (2H, d, J=9 Hz), 6.91 (2H, d, J=9 Hz), 7.28 (1H, dd, J=2 Hz and 9 Hz), 7.53 (1H, d, J=2 Hz), 7.73 (1H, d, J=9 Hz).

PREPARATION 4

In a similar manner to that of Preparation 2, there were obtained the following compounds.

(1) 2-Amino-4-methoxy-N-(P-tolyl)benzenesulfonamide
IR (CHCl₃): 3500, 3400, 1610, 1570, 1450, 1150 cm⁻¹.
NMR (CDCl₃, δ): 2.23 (3H, s), 3.75 (3H, s), 4.90 (2H, br s), 6.18–6.25 (2H, m), 6.85–7.10 (4H, m), 7.40 (1H, d, J=9 Hz).

(2) 2-Amino-4-methoxy-N-(phenyl)benzenesulfonamide
mp: 112°–114° C.
IR (Nujol): 3500, 3400, 3200, 1630, 1610, 1500, 1470 cm⁻¹.
NMR (CDCl₃, δ): 3.75 (3H, s), 4.90 (2H, br s), 6.10–6.30 (2H, m), 7.00–7.30 (5H, m), 7.40 (1H, d, J=9 Hz).

(3) 2-Amino-4-methoxy-N-(4-trifluoromethyl-phenyl)-benzenesulfonamide
mp: 92°–94° C.
IR (Nujol): 3400, 3300, 1620, 1600, 1460, 1330, 1130 cm⁻¹.
NMR (CDCl₃, δ): 3.60 (3H, s), 6.00 (2H, br s), 6.18 (1H, dd, J=2 Hz and 9 Hz), 6.22 (1H, d, J=2 Hz), 7.22 (2H, d, J=7 Hz), 7.52 (1H, d, J=9 Hz), 7.60 (2H, d, J=7 Hz), 10.7 (1H, br s)

(4) 2-Amino-4-methoxy-N-(3,4-dichlorophenyl)benzenesulfonamide
mp: 135°–138° C.
IR (Nujol): 3400, 3300, 1600, 1470, 1380 cm⁻¹.
NMR (CDCl₃, δ): 3.77 (3H, s), 4.85 (2H, br s), 6.19 (1H, d, J=2 Hz), 6.27 (1H, dd, J=2 Hz, and 9 Hz), 6.80 (1H, br s).

(5) 2-Amino-4-methoxy-N-(4-Fluorophenyl)benzenesulfonamide
mp: 94°–97° C.
IR (CHCl₃): 3500, 3400, 3200, 1630, 1600, 1460, 1310, 1220 cm⁻¹.
NMR (DMSO-d₆, δ): 3.65 (3H, s), 5.95 (2H, br s), 6.13 (1H, dd, J=2 Hz and 9 Hz), 6.22 (1H, d, J=2 Hz), 7.35 (1H, d, J=9 Hz).

(6) 2-Amino-4-isopropoxy-N-(4-methoxyphenyl)benzenesulfonamide
IR (CHCl₃) 3500, 3350, 1720, 1600, 1510, 1240 cm⁻¹.
NMR (CDCl₃, δ): 1.30 (6H, d, J=6 Hz), 3.75 (3H, s), 4.50 (1H, m), 4.80 (2H, br s), 6.12–6.20 (2H, m), 6.72 (2H, d, J=7 Hz), 6.95 (2H, d, J=7 Hz), 7.80 (1H, d, J=9 Hz).

(7) 2-Amino-N-(4-chlorophenyl)benzenesulfonamide
mp: 100°–105° C.
IR (Nujol): 1620, 1490, 1460, 1450, 1320, 1150, 1140 cm⁻¹.
NMR (CDCl₃, δ): 4.85 (2H, br s), 6.60–6.80 (2H, m), 6.90–7.40 (5H, m), 7.50 (1H, d, J=9 Hz.

(8) 2-Amino-4-chloro-N-(4-cholorphenyl)benzenesulfonamide
mp: 114°–115° C.
IR (Nujol): 1610, 1590, 1480, 1440, 1310, 1160, 1140 cm⁻¹.
NMR (CDCl₃, δ): 4.95 (2H, br s), 6.63 (1H, dd, J=2 Hz and 9 Hz), 6.72 (1H, d, J=2 Hz), 6.90–7.30 (4H, m), 7.38 (1H, d, J=9 Hz).

(9) 2-Amino-4-methoxy-N-(2-chlorophenyl)benzenesulfonamide
mp: 137°–138° C.
IR (Nujol): 3700, 3500, 3300, 1640, 1600, 1570, 1380, 1320, 1220, 1140 cm⁻¹.
NMR (CDCl₃, δ): 3 75 (3H, s), 4.99 (2H, br s), 6.12 (1H, d, J=2 Hz), 6.22 (1H, dd, J=2 Hz and 9 Hz), 6.90–7.70 (5H, m).

(10) 2-Amino-4-methoxy-N-(3-chlorophenyl)benzenesulfonamide
mp: 138°–140° C.
IR (Nujol): 3450, 3350, 3250, 1540, 1600, 1460, 1380, 1160, 1140 cm⁻¹.
NMR (CDCl₃, δ): 3.75 (3H, s), 4.90 (2H, br s), 6.20 (1H, d, J=2 Hz), 6.25 (1H, dd, J=2 Hz and 9 Hz), 6.75 (1H, br s), 6.90–7.30 (3H, m), 7.45 (1H, d, J=9 Hz).

(11) 2-Amino-4-isopropoxy-N-(4-chlorophenyl)benzenesulfonamide
IR (CHCl₃): 3400, 3300, 3100, 1650, 1600, 1490, 1320 cm⁻¹.
NMR (CDCl₃, δ): 1.30 (6H, d, J=6 Hz), 1.50 (1H, m), 4.85 (2H, br s), 6.10–6.25 (2H, m), 6.90–7.25 (4H, m), 7.90 (1H, d, J=9 Hz).

(12) 2-Amino-4-methoxy-N-(4-chlorobenzyl)benzenesulfonamide
mp: 121°–122° C.
IR (Nujol): 3470, 3370, 3250, 1620, 1600, 1565, 1265 cm⁻¹.
NMR (CDCl₃, δ): 3.81 (3H, s), 4.00 (2H, d, J=6.0 Hz), 4.85 (2H, s), 4.96 (1H, t, J=6.0 Hz), 6.21 (1H, d, J=2.4 Hz), 6.34 (1H, dd, J=2.4 and 8.8 Hz), 7.13 and 7.23 (4H, ABq, J=8.5 Hz), 7.61 (1H, d, J=8.8 Hz).

(13) 2-Amino-4-methoxy-N-cyclohexylbenzenesulfonamide mp: 95°–98° C.

IR (Nujol): 3450, 3360, 3280, 1650, 1600, 1575, 1300, 1130, 1065 cm$^{-1}$.

NMR (CDCl$_3$, δ): 1.0–1.4 (5H, m), 1.4–1.8 (5H, m), 2.95–3.15 (1H, m), 3.81 (3H, s), 4.58 (1H, d, J=7.5 Hz), 4.84 (2H, s), 6.22 (1H, d, J=2.3 Hz), 6.35 (1H, dd, J=2.3 and 8.8Hz), 7.64 (1H, d, J=8.8 Hz).

(14) 2-Amino-4-isopropoxy-N-(2-pyridyl)benzenesulfonamide mp 176°–177° C.

NMR (DMSO-d$_6$, δ): 1.23 (6H, d, J=6 Hz), 4.4–4.6 (1H, m), 6.0 (2H, br s), 6.15 (1H, dd, J=2 Hz and 9 Hz), 6.22 (1H, d, J=2 Hz), 6.85–6.95 (1H, m), 7.0–7.10 (1H, m), 7.52 (1H, d, J=9 Hz), 7.6–7.75 (1H, m), 8.03–8.1 (1H, m).

(15) 2-Amino-4-methoxy-N-(pentyl)benzenesulfonamide

IR (Nujol): 3500, 3350, 1620, 1320, 1300, 1160, 1140 cm$^{-1}$.

NMR (DMSO-d$_6$, δ): 0.85 (3H, t, J=7 Hz), 1.05–1.60 (6H, m), 2.85 (2H, q, J=7 Hz), 3.80 (3H, s), 4.60 (1H, t, J=7 Hz), 4.90 (2H, br s), 6.25 (1H, d, J=3 Hz), 6.85 (1H, dd, J=3 Hz and 9 Hz), 7.62 (1H, d, J=9 Hz).

(16) 2-Amino-4-methoxy-N-(4-methoxycarbonylphenyl)-benzenesulfonamide mp: 195° C. (dec.).

IR (Nujol) 3460, 3370, 3230, 1690, 1610, 1300 cm$^{-1}$.

NMR (DMSO-d$_6$, δ): 3.65 (3H, s), 3.75 (3H, s), 6.03 (2H, br s), 6.15–6.30 (2H, m), 7.14 and 7.80 (4H, ABq, J=9.5 Hz), 7.50 (1H, d, J=9.5 Hz), 10.68 (1H, br s).

(17) 2-Amino-4-cyclohexylmethoxy-N-(2-pyridyl)-benzenesulfonamide mp: 213°–214° C.

IR (Nujol): 3460, 3360, 1630, 1620, 1130 cm$^{-1}$.

NMR (DMSO-d$_6$, δ): 0.85–1.4 (5H, m), 1.55–1.85 (6H, m), 3.70 (2H, d, J=6 Hz), 6.0 (2H, br s), 6.16 (1H, dd, J=2.3 Hz and 8.8 Hz), 6.23 (1H, d, J=2.3 Hz), 6.83–6.95 (1H, m), 7.0–7.08 (2H, m), 7.53 (1H, d, J=8.8 Hz), 7.6–7.72 (1H, m), 8.0–8.1 (1H, m).

(18) 2-Amino-4-methoxy-N-(4-methoxycarbonylmethylphenyl)-benzenesulfonamide mp: 111°–113° C.

IR (Nujol): 3450, 3360, 3270, 1720, 1595, 1135 cm$^{-1}$.

NMR (DMSO-d$_6$, δ): 3.54 (2H, s), 3.57 (3H, s), 3.67 (3H, s), 5.99 (2H, s, NH2), 6.1–6.2 (1H, m), 6.22–6.27 (1H, m), 6.96 and 7.10 (4H, ABq, J=8.2 Hz), 7.42 (1H, d, J=8.8 Hz), 10.1 (1H, br s).

(19) 2-Amino-4-methoxy-N-(3-ethoxycarbonylpropyl)-benzenesulfonamide mp 53°–54° C.

IR (Nujol): 3500, 3400, 3300, 1710, 1630, 1610, 1570, 1470, 1380, 1310, 1270, 1220, 1160 cm$^{-1}$.

NMR (CDCl$_3$, δ): 1.24 (3H, t, J=Hz), 1.76 (2H, m), 2.33 (2H, t, J=7 Hz), 2.91 (2H, q, J=7 Hz), 3.80 (3H, s), 4.10 (2H, q, J=7 Hz), 4.85 (1H, br s), 6.23 (1H, d, J=2 Hz), 6.35 (1H, dd, J=2 Hz and 9 Hz), 7.61 (1H, d, J=9 Hz).

(20) 2-Amino-4-methyl-N-(4-chlorophenyl)benzenesulfonamide mp: 96°–98° C.

IR (Nujol): 3400, 3300, 3100, 1610, 1500, 1330, 1230, 1140 cm$^{-1}$.

NMR (CDCl$_3$, δ): 2.25 (3H, s), 4.77 (2H, br s), 6.50 (1H, d, J=8 Hz), 6.54 (1H, s), 7.00 (2H, d, J=8 Hz).

(21) 2-Amino-4-isopropoxy-N-[2-(4,6-dimethylpyridyl)]-benzenesulfonamide mp: 180°–182° C.

IR (Nujol): 340, 3350, 3250, 1620, 1600, 1400, 1250, 1130 cm$^{-1}$.

NMR (DMSO-d$_6$, δ): 1.22 (6H, d, J=6 Hz), 2.15 (3H, s), 2.22 (3H, s), 4.50 (1H, m), 5.85 (2H, br s), 6.12 (1H, d, J=9 Hz), 6.22 (1H, s), 6.50 (1H, s), 6.70 (1H, s), 7.50 (1H, d, J=9 Hz).

(22) 2-Amino-4-trifluoromethyl-N-(4-chlorophenyl)-benzenesulfonamide mp: 100°–102° C.

IR (Nujol): 3420, 3350, 1630, 1500, 1340, 1190, 1140, 1090 cm$^{-1}$.

NMR (CDCl$_3$, δ): 5.00 (2H, br s), 6.70–7.40 (6H, m), 7.70 (1H, d, J=9 Hz).

(23) 2-Amino-4-isopropoxy-N-(2-pyrimidinyl)benzenesulfonamide mp: 204°–206° C.

IR (Nujol): 3400, 3300, 1610, 1580, 1500, 1450, 1380, 1320, 1130 cm$^{-1}$.

NMR (DMSO-d$_6$, δ): 1.25 (6H, d, J=6 Hz), 1.45 (1H, m), 6.00 (2H, br s), 6.15 (1H, d, J=9 Hz), 7.00 (1H, t, J=4 Hz), 7.60 (1H, d, J=9 Hz), 8.50 (2H, d, J=4 Hz), 11.4 (1H, br s).

(24) 2-Amino-4-methoxy-N-(4-phenoxyphenyl)benzenesulfonamide mp: 100°–101° C.

IR (Nujol): 3460, 3360, 3270, 1600, 1310, 1245, 1135 cm$^{-1}$. IR (Nujol): 3460, 3360, 3270, 1600, 1310, 1245, 1135 cm$^{-1}$.

NMR (CDCl$_3$, δ): 3.50 (2H, br), 3.77 (3H, s), 6.25 (1H, d, J=2 Hz), 6.26 (1H, dd, J=2 Hz and 9 Hz), 6.73 (1H, br s), 6.80–7.45 (10H, m).

(25) 2-Amino-4-methoxy-N-(4-isopropylphenyl)benzenesulfonamide mp: 98°–99° C.

IR (Nujol): 3460, 3360, 3260, 1605, 1575, 1305, 1215 cm$^{-1}$.

NMR (CDCl$_3$, δ): 1.18 (6H, d, J=7 Hz), 2.82 (1H, m), 3.45 (2H, br), 3.76 (3H, s), 6.23 (1H, dd, J=2 Hz and 9 Hz), 6.25 (1H, d, J=2 Hz), 6.72 (1H, br s), 6.95 and 7.05 (4H, ABq, J=9 Hz), 7.40 (1H, d, J=9 Hz).

(26) 2-Amino-4-methoxy-N-[(3-chloro-4-methyl)-phenyl]-benzenesulfonamide mp: 138°–139° C.

IR (Nujol): 3420, 3350, 3250, 1600, 1315, 1140 cm$^{-1}$.

NMR (CDCl$_3$, δ): 2.27 (3H, s), 3.45 (2H, br), 6.24 (1H, d, J=2 Hz), 6.27 (1H, dd, J=2 Hz and 9 Hz), 6.80 (1H, br s), 6.85 (1H, dd, J=2 Hz and 9 Hz), 7.05 (1H, d, J=9 Hz), 7.08 (1H, d, J=2 Hz), 7.43 (1H, d, J=9 Hz).

(27) 2-Amino-4-methoxy-N-(4-methylthiophenyl)-benzenesulfonamide mp: 91°–92° C.

IR (Nujol): 3450, 3375, 3250, 1625, 1600, 1570, 1490, 1215, 1160, 1140 cm$^{-1}$.

NMR (CDCl$_3$, δ): 2.51 (3H, s), 3.86 (3H, s), 6.50 (1H, d, J=2 Hz), 6.82 (1H, dd, J=2 Hz and 9 Hz), 7.36 (4H, s), 7.79 (1H, d, J=9 Hz), 8.51 (1H, s).

(28) 2-Amino-4-methoxy-N-(4-dimethylaminophenyl)-benzenesulfonamide mp: 119°–121° C.

IR (Nujol): 3450, 3440, 3350, 3250, 1600, 1520, 1210, 1160, 1140 cm$^{-1}$.

NMR (DMSO-d$_6$, δ): 2.79 (6H, s), 3.68 (3H, s), 6.10 (1H, dd, J=2 Hz and 9 Hz), 6.24 (1H, d, J=2 Hz), 6.55 (2H, d, J=9 Hz), 6.85 (2H, d, J=9 Hz), 7.26 (1H, d, J=9 Hz), 9.42 (1H, s).

PREPARATION 5

To a solution of 4-acetylamino-2-nitro-N-(4-chlorophenyl)benzenesulfonamide (4.85 g) in ethyl acetate (485 ml) was added 10% palladium on carbon, and the mixture was hydrogenated at room temperature under atmospheric pressure for seven hours. The catalyst was removed by filtration and the solvent was evaporated under reduced pressure. The residue was triturated with diisopropyl ether and collected by filtration to give 4-acetylamino-2-amino-N-(4-chlorophenyl)benzenesulfonamide as colorless powder (4.76 g).

mp: 127° C. (dec.).

IR (Nujol): 3340, 1665, 1600, 1310, 1135 cm$^{-1}$.

NMR (DMSO-d$_6$, δ): 2.01 (3H, s), 5.87 (2H, br), 6.67-6.75 (1H, m), 7.0-7.56 (6H, m), 9.95 (1H, br), 10.4 (1H, br).

EXAMPLE 1

A mixture of 2-amino-4-methoxy-N-(4-chlorophenyl)-benzenesulfonamide (24.37 g) and 1,1'-carbonyldiimidazole (18.93 g) in dried dioxane (500 ml) was refluxed overnight and then concentrated to dryness. The residue was washed with methanol and collected by filtration to yield 2-(4-chlorophenyl)-6-methoxy-2H-1,2,4-benzothiadiazine-3(4H)-one 1,1-dioxide (23.9 g).

mp: 229°-230° C.

IR (Nujol): 1700, 1610, 1600, 1480, 1360, 1300 cm$^{-1}$.

NMR (DMSO-d$_6$, δ): 3.38 (1H, br s), 3.85 (3H, s), 6.30-7.00 (2H, m), 7.40-7.70 (4H, m), 7.85 (1H, d, J=9 Hz).

EXAMPLE 2

To a solution of 2-(4-chlorophenyl)-6-methoxy-2H-1,2,4-benzothiadiazine-3(4H)-one 1,1-dioxide (23.50 g) in dried N,N-dimethylformamide (150 ml) was added sodium hydride (60% oil dispersion) in one portion at 0° C. The suspension was stirred for one hour at ambient temperature and then methyl iodide (5.18 ml) was added therein at the same temperature. The reaction mixture was stirred for one and half hours a ambient temperature and then poured into ice water. The separated solid was filtered, dried and recrystrallized from ethanol to yield 2-(4-chlorophenyl)-6-methoxy-4-methyl-2H-1,2,4-benzothiadiazine-3(4H)-one 1,1-dioxide (21.07 g) as a white needle crystal.

mp: 167°-168° C.

IR (Nujol): 1710, 1600, 1330, 1180, 1130, cm$^{-1}$.

NMR (DMSO-d$_6$, δ): 3.42 (3H, s), 3.95 (3H, s), 6.95-7.10 (2H, m), 7.38-7.65 (2H, m), 8.90 (1H, d, J=9 Hz).

EXAMPLE 3

To a solution of 2-(4-chlorophenyl)-6-methoxy-4-methyl-2H-1,2,4-benzothiadiazine-3(4H)-one 1,1-dioxide (21.0 g) in methylene chloride (200 ml) was added boron tribromide (1N solution in methylene chloride, 89.2 ml) at ambient temperature. The mixture was stirred for 8 hours at the same temperature and then poured into ice water. The separated solid was collected by filtration, dried, and recrystallized from ethanol to yield 2-(4-chlorophenyl)-6-hydroxy-4-methyl-2H-1,2,4-benzothiadiazine-3(4H)-one 1,1-dioxide (18.86 g).

mp: >250° C.

IR (Nujol): 3300, 1660, 1650, 1610, cm$^{-1}$.

NMR (DMSO-d$_6$, δ): 3.45 (3H, s), 6.80 (1H, d, J=9 Hz), 7.90 (1H, s), 7.35-7 65 (4H, m), 7.70 (1H, d, J=9 Hz).

EXAMPLE 4

A suspension of 2-(4-chlorophenyl)-6-hydroxy-4-methyl-2H-1,2,4-benzothiadiazine-3(4H)-one 1,1-dioxide (15.33 g), potassium carbonate (7.50 g) and 2-iodopropane (5.43 ml) in N,N-dimethylformamide (150 ml) was stirred for 2 hours at 60° C. The mixture was poured into ice water. The separated solid was collected by filtration, dried, and recrystallized from ethanol to yield 2-(4-chlorophenyl)-6-isopropoxy-4-methyl-2H-1,2,4-benzothiadiazine-3(4H)-one 1,1-dioxide (13.54 g) as a white crystal.

mp: 157°-159° C.

IR (Nujol): 1700, 1605, 1460, 1330, 1320, 1300 cm$^{-1}$.

NMR (DMSO-d$_6$, δ): 1.32 (3H, s), 1.35 (3H, s), 3.50 (3H, s), 4.89 (1H, m), 7.00 (1H, d, J=9 Hz), 7.02 (1H, s), 7.35-7.60 (4H, m), 7,85 (1H, d, J=9 Hz).

EXAMPLE 5

In a similar manner to that of Example 1, there were obtained the following compounds.

(1) 6-Methoxy-2-(P-tolyl)-2H-1,2,4-benzothiadiazine-3(4H)-one 1,1-dioxide mp: 228°-230° C.

IR (Nujol): 1710, 1700, 1630, 1610, 1480, 1400, 1340, 1200, 1120 cm$^{-1}$.

NMR (DMSO-d$_6$, δ): 2 38 (3H, s), 3.88 (3H, s), 6.70-7.10 (2H, m), 7.20-7.50 (4H, m), 7.85 (1H, d, J=9 Hz), 11.45 (1H, br s).

(2) 6-Methoxy-2-phenyl-2H-1,2,4-benzothiadiazine-3(4H)-one 1,1-dioxide mp: 203°-235° C.

IR (Nujol): 3500, 1700, 1690, 1610, 1590, 1460, 1370 cm$^{-1}$.

NMR (DMSO-d$_6$, δ): 3.85 (3H, s), 6.80 (1H, s), 6.95 (1H, d, J=9 Hz), 7.30-7.70 (5H, m), 7.82 (1H, d, J=9 Hz), 11.5 (1H, br s).

(3) 6-Methoxy-2-(4-trifluoromethylphenyl)-2H-1,2,4-benzothiadiazine-3(4H)-one 1,1-dioxide mp: 202°-204° C.

IR (Nujol): 1700, 1610, 1590, 1460, 1380, 1320, 1180 cm$^{-1}$.

NMR (DMSO-d$_6$, δ): 3.85 (3H, s), 6.50 (1H, d, J=2 Hz), 6.85 (1H, dd, J=2 Hz and 9 Hz), 7.62 (2H, d, J=7 Hz), 7.72 (2H, d, J=7 Hz), 7.80 (1H, d, J=9 Hz).

(4) 2-(3,4-Dichlorophenyl)-6-methoxy-2H-1,2,4-benzothiadiazine-3(4H0-one 1,1-dioxide mp: 239°-240° C.

IR (Nujol): 1720, 1600, 1470, 1360, 1190 cm$^{-1}$.

NMR (DMSO-d$_6$, δ): 3.45 (3H, s), 6.70-7.00 (2H, m), 7.45 (1H, d, J=8 Hz), 7.70-7.95 (3H, m), 11.50 (1H, br s).

(5) 2-(4-Fluorophenyl)-6-methoxy-2H-1,2,4-benzothiadiazine-3(4H)-one 1,1-dioxide mp: 224°-225° C.

IR (Nujol): 3250, 3150, 1690, 1600, 1360, 1290, 1180, 1170, 1150 cm$^{-1}$.

NMR (DMSO-d$_6$, δ): 3.85 (3H, s), 6.80 (1H, s), 6.92 (1H, d, J=10 Hz), 7.30-7.60 (4H, m), 7.85 (1H, d,J=10H).

(6) 6-Isopropoxy-2(4-methoxyphenyl)-2H-1,2,4-benzothiadiazine-3(4H)-one 1,1-dioxide mp: 208°-210° C.

IR (Nujol): 3200, 1700, 1620, 1590, 1460 cm$^{-1}$.

NMR (DMSO-d$_6$, δ): 1.32 (6H, d, J=2 Hz), 6.90 (1H, dd, J=2 Hz and 9 Hz), 7.05 (2H, d, J=7 Hz), 7.30 (2H, d, J=7 Hz), 7.80 (1H, d, J=9 Hz), 11.4 (1H, br s).

(7) 6-Chloro-2-(4-chlorophenyl)-2H-1,2,4-benzothiadiazine-3(4H)-one 1,1-dioxide mp: 235°–237° C.

IR (Nujol): 1720, 1710, 1600, 1580, 1460, 1310, 1170, 1160, 1100 cm$^{-1}$.

NMR (DMSO-d$_6$, δ): 7.20–7.75 (6H, m), 7.98 (1H, d, J=9 Hz), 11.8 (1H, brs) 2-(2-Chlorophenyl)-6-methoxy-2H-1,2,4-benzothiadiazine-3(4H)-one 1,1-dioxide mp: 234°–235° C.

IR (Nujol): 3400, 1720, 1620, 1600, 1590, 1460, 1320, 1290, 1140 cm$^{-1}$.

NMR (DMSO-d$_6$, δ): 3.87 (3H, s), 6.87 (1H, s), 9.24 (1H, dd, J=2 Hz and 9 Hz), 7.50–7.72 (4H, m), 7.84 (1H, d, J=9 Hz), 11.6 (1H, br s).

(9) 2-(3-Chlorophenyl)-6-methoxy-2H-1,2,4-benzothiadiazine-3(4H)-one 1,1-dioxide mp: 204°–205° C.

IR (Nujol): 1700, 1590, 1470, 1370, 1350, 1200, 1170, 1140 cm$^{-1}$.

NMR (DMSO-d$_6$, δ): 3.90 (3H, s), 6.80 (1H, d, J=2 Hz), 6.92 (1H, dd, J=2 Hz and 9 Hz), 7.30–7.75 (3H, m), 7.85 (1H, d, J=9 Hz).

(10) 2-(4-Chlorophenyl)-6-isopropoxy-2H-1,2,4-benzothiadiazine-3 (4H)-one 1,1-dioxide mp: 132°–133° C.

IR (Nujol): 1700, 1460, 1370, 1340 cm$^{-1}$.

NMR (DMSO-d$_6$, δ): 1.32 (6H, d, J=6 Hz), 4.70 (1H, m), 6.78 (1H, d, J=2 Hz), 6.90 (1H, dd, J=2 Hz and 9 Hz), 7.42 (2H, d, J=7 Hz), 7.60 (2H, d, J=7 Hz), 7.90 (1H, d, J=9 Hz).

(11) 2-(4-Chlorobenzyl)-6-methoxy-2H-1,2,4-benzothiadiazine-3(4H)-one 1,1-dioxide mp: 199°–200° C.

IR (Nujol): 3200, 3060, 1695, 1610, 1590, 1335, 1320 cm$^{-1}$.

NMR (DMSO-d$_6$, δ): 3.84 (3H, s), 4.95 (2H, s), 6.77 (1H, d, J=2.0 Hz), 6.90 (1H, dd, J=2.0 and 9.0 Hz), 7.35 and 7.40 (4H, ABq, J=8.7 Hz), 7.80 (1H, d, J=9.0 Hz), 11.37 (1H, br).

(12) 2-Cyclohexyl-6-methoxy-2H-1,2,4-benzothiadiazine-3(4H)-one 1,1-dioxide mp: 190°–191° C.

IR (Nujol): 3200, 3070, 1690, 1600, 1185, 1170 cm$^{-1}$.

NMR (DMSO-d$_6$, δ): 1.0–1.5 (3H, m), 1.5–1.95 (5H, m), 2.1–2.4 (2H, m), 3.82 (3H, s), 4.2–4.45 (1H, m), 6.73 (1H, s), 6.85 (1H, dd, J=2.2 and 8.8 Hz), 7.72 (1H, d, J=8.8 Hz), 11.17 (1H, br).

(13) 6-Isopropoxy-2-(2-pyridyl)-2H-1,2,4-benzothiadiazine-3(4H)-one 1,1-dioxide mp: 183°–184° C.

IR (Nujol): 3450, 1745, 1615, 1340 cm$^{-1}$.

NMR (DMSO-d$_6$, δ): 1.32 (6H, d, J=6 Hz), 4.6–4.8 (1H, m), 6.81 (1H, d, J=2.2 Hz), 6.90 (1H, J=2.2 Hz and 8.8 Hz), 7.45–7.6 (2H, m), 7.76 (1H, d, J=8.8 Hz), 7.95–8.06 (1H, m), 8.55–8.65 (1H, m), 11.48 (1H, br s).

(14) 6-Methoxy-2-pentyl-2H-1,2,4-benzothiadiazine-3(4H)-one 1,1-dioxide mp: 100°–104° C.

IR (Nujol): 1690, 1610, 1600, 1470, 1350, 1330 cm$^{-1}$.

NMR (DMSO-d$_6$, δ): 0.85 (3H, t, J=6 Hz), 1.15–1.40 (4H, m), 1.50–1.70 (2H, m), 3.73 (3H, t, J=7 Hz), 3.83 (3H, s), 6.73 (1H, d, J=2 Hz), 6.87 (1H, dd, J=2 Hz and 9 Hz), 7.76 (1H, d, J=9 Hz).

(15) 6-Acetylamino-2-(4-chlorophenyl)-2H-1,2,4-benzothiadiazine-3(4H)-one 1,1-dioxide mp: >250° C.

IR (Nujol): 3360, 1725, 1600, 1325 cm$^{-1}$.

NMR (DMSO-d$_6$, δ) 2.11 (3H, s), 7.4–7.5 (3H, m), 7.55–7.67 (2H, m), 7.80–7.90 (2H, m), 10.51 (1H, s), 11.60 (1H, s).

(16) 6-Methoxy-2-(4-methoxycarbonylphenyl)-2H-1,2,4-benzothiadiazine-3(4H)-one 1,1-dioxide mp: 231°–233° C.

IR (Nujol) 3260, 1720, 1695, 1600, 1335, 1320 cm$^{-1}$.

NMR (DMSO-d$_6$, δ): 3.88 (3H, s), 3.91 (3H, s), 6.84 (1H, d, J=2 Hz), 6.95 (1H, dd, J=2 Hz and 9 Hz), 7.60 and 8.10 (4H, ABq, J=8.5 Hz), 7.85 (1H, d, J=9 Hz), 11.58 (1H, br s).

(17) 6-Cyclohexylmethoxy-2-(2-pyridyl)-2H-1,2,4-benzothiadiazine-3(4H)-one 1,1-dioxide mp: 206°–208° C.

IR (Nujol): 3150, 1745, 1610. 1595, 1340, 1325, 1310, 1180 cm$^{-1}$.

NMR (DMSO-d$_6$, δ): 0.9–1.4 (5H, m), 1.55–1.9 (6H, m), 3.99 (2H, d, J=6 Hz), 6.82 (1H, d, J=2.1 Hz), 6.92 (1H, dd, J=2.1 Hz and 8.8 Hz) 7.45–7.6 (2H, m), 7.77 (1H, d, J=8.8 Hz), 7.95–8.08 (1H, m), 8.55–8.65 (1H, m), 11.49 (1H, br s).

(18) 2-(4-Methoxycarbonylmethylphenyl)-6-methoxy-2H-1,2,4-benzothiadiazine-3(4H)-one 1,1-dioxide mp: 214°–215° C.

IR (Nujol): 3200, 1720, 1700, 1340 cm$^{-1}$.

NMR (DMSO-d$_6$, δ): 3.65 (3H, s), 3.79 (2H, s), 3.86 (3H, s) 6.80–6.85 (1H, m), 6.43 (1H, dd, J=2.0 and 9.0 Hz), 7.35 and 7.45 (4H, ABq, J=8.3 Hz), 7.85 (1H, d, J=9.0 Hz), 11.5 (1H, br).

(19) 2-(3-Ethoxycarbonylpropyl)-6-methoxy-2H-1,2,4-benzothiadiazine-3(4H)-one 1,1-dioxide mp: 118°–120° C.

IR (Nujol): 3250, 1730, 1700, 1450, 1380, 1320 cm$^{-1}$.

NMR (DMSO-d$_6$, δ): 1.15 (3H, t, J=7 Hz), 1.88 (2H, m), 2.34 (2H, t, J=7 Hz), 3.35 (1H, br s), 3.60–3.80 (2H, m), 6.88 (1H, dd, J=2 Hz and 9 Hz), 7.77 (1H, d, J=9 Hz).

(20) 2-(4-Chlorophenyl)-6-methyl-2H-1,2,4-benzothiadiazine-3(4H)-one 1,1-dioxide mp: 245°–248° C.

IR (Nujol): 1690, 1610, 1590, 1490, 1350, 1190, 1150, 1090 cm$^{-1}$.

NMR (DMSO-d$_6$, δ): 2.41 (3H, s), 3.35 (1H, br s), 7.13 (1H, s), 7.18 (1H, d, J=8 Hz), 7.46 (2H, d, J=8 Hz), 7.60 (2H, d, J=8 Hz), 7.79 (1H, d, J=8 Hz).

(21) 2-[2-(4,6-Dimethylpyridyl)]-6-isopropoxy-2H-1,2,4-benzothiadiazine-3(4H)-one 1,1-dioxide mp: 188°–190° C.

IR (Nujol): 3600, 1740, 1600, 1330, 1180 cm$^{-1}$.

NMR (DMSO-d$_6$, δ): 1.33 (6H, d, J=8 Hz), 2.35 (3H, s), 2.45 (3H, s), 4.72 (1H, m), 6.80 (1H, d, J=2 Hz), 6.90 (1H, dd, J=2 Hz and 9 Hz), 7.10 (1H, s), 7.25 (1H, s), 7.75 (1H, d, J=9 Hz).

(22) 2-(4-Chlorophenyl)-6-trifluoromethyl-2H-1,2,4benzothiadiazine-3(4H)-one 1,1-dioxide mp: 234°–235° C.

IR (Nujol): 1720, 1600, 1490, 1360, 1340, 1190, 1140, 1090 cm$^{-1}$.

NMR (DMSO-d$_6$, δ): 7.40–7.80 (6H, m), 8.17 (1H, d, J=9 Hz).

(23) 6-Isopropoxy-2-(2-pyrimidinyl)-2H-1,2,4-benzothiadiazine-3(4H)-one 1,1-dioxide mp: 168°–170° C.

IR (Nujol): 3600, 1740, 1600, 1570, 1350, 1320, 1180 cm$^{-1}$.

NMR (DMSO-d$_6$, δ): 1.30 (6H, d, J=6 Hz), 4.72 (1H, m), 6.80 (1H, d, J=2 Hz), 6.92 (1H, dd, J=2 Hz and 9 Hz), 7.70 (1H, t, J=4 Hz), 7.80 (1H, d, J=9 Hz), 9.00 (2H, d, J=4 Hz), 11.65 (1H, br s).

(24) 6-Methoxy-2-(4-phenoxyphenyl)-2H-1,2,4-benzothiadiazine-3(4H)-one 1,1-dioxide
mp: 247°–248° C.
IR (Nujol): 3210, 3110, 3060, 1700, 1595, 1340, 1245 cm$^{-1}$.

NMR (DMSO-d$_6$, δ): 3.86 (3H, s), 6.81 (1H, d, J=2 Hz), 6.92 (1H, dd, J=2 Hz and 9 Hz), 7.00–7.55 (9H, m), 7.82 (1H, d, J=9 Hz), 11.47 (1H, br).

(25) 2-(4-Isopropylphenyl)-6-methoxy-2H-1,2,4-benzothiadiazine-3(4H)-one 1,1-dioxide
mp: 213°–214° C.
IR (Nujol): 3200, 2960, 1695, 1610, 1590, 1195 cm$^{-1}$.

NMR (DMSO-d$_6$, δ): 1.25 (6H, d, J=7 Hz), 3.00 (1H, m), 3.86 (3H, s), 6.81 (1H, d, J=2 Hz), 6.92 (1H, dd, J=2 Hz and 9 Hz), 7.30 and 7.40 (4H, ABq, J=8.5 Hz), 7.81 (1H, d, J=9 Hz), 11.45 (1H, br).

(26) 2-[(3-Chloro-4-methyl)phenyl]-6-methoxy-2H-1,2,4-benzothiadiazine-3(4H)-one 1,1-dioxide
mp: 222°–223° C.
IR (Nujol): 3220, 1710, 1600, 1180 cm$^{-1}$.

NMR (DMSO-d$_6$, δ): 2.40 (3H, s), 3.87 (3H, s), 6.80 (1H, d, J=2 Hz), 7.32 (1H, dd, J=2 Hz and 8.5 Hz), 7.5 (1H, d, J=2 Hz), 7.52 (1H, d, J=8.5 Hz), 7.83 (1H, d, J=9 Hz), 9.93 (1H, dd, J=2 Hz and 9 Hz), 11.5 (1H, br s).

(27) 6-Methoxy-2-(4-methylthiophenyl)-2H-1,2,4-benzothiadiazine-3(4H)-one 1,1-dioxide
mp: 218°–219° C.
IR (Nujol): 1685, 1590, 1210, 1190, 1180 cm$^{-1}$.

NMR (DMSO-d$_6$, δ): 2.51 (3H, s), 3.86 (3H, s), 6.81 (1H, d, J=2 Hz), 6.92 (1H, dd, J=2 Hz and 9 Hz), 7.31 (2H, d, J=8 Hz), 7.39 (2H, d, J=8 Hz), 7.82 (1H, d, J=9 Hz).

(28) 2-(4-Dimethylaminophenyl)-6-methoxy-2H-1,2,4-benzothiadiazine-3(4H)-one 1,1-dioxide
mp: >250° C.
IR (Nujol): 1680, 1600, 1520, 1350, 1210, 1170 cm$^{-1}$.

NMR (DMSO-d$_6$, δ): 2.96 (6H, s), 3.85 (3H, s), 6.76 (2H, d, J=9 Hz), 7.13 (2H, d, J=9 Hz), 6.79 (1H, d, J=2 Hz), 6.90 (1H, dd, J=2 Hz and 9 Hz), 7.79 (1H, d, J=9 Hz).

EXAMPLE 6

In a similar manner to that of Example 2, there were obtained the following compounds.

(1) 6-Methoxy-4-methyl-2-(P-tolyl)-2H-1,2,4-benzothiadiazine-3(4H)-one 1,1-dioxide
mp: 170°–173° C.
IR (Nujol): 1690, 1460, 1440, 1330, 1310, 1180, 1130 cm$^{-1}$.

NMR (DMSO-d$_6$, δ): 3.50 (3H, s), 3.95 (3H, s), 6.95–7.10 (2H, m), 7.20–7.40 (4H, m), 7.95 (1H, d, J=9 Hz).

(2) 6-methoxy-4-methyl-2-phenyl-2H-1,2,4-benzothiadiazine-3(4H)-one 1,1-dioxide
mp: 203°–206° C.
IR (Nujol): 1710, 1700, 1600, 1450, 1330, 1300, 1220, 1180 cm$^{-1}$.

NMR (DMSO-d$_6$, δ): 3.50 (3H, s), 3.95 (3H, s), 7.00 (1H, d, J=9 Hz), 7.05 (1H, s), 7.35–7.65 (5H, m), 7.88 (1H, d, J=9 Hz).

(3) 6-Methoxy-4-methyl-2-(4trifluoromethylphenyl)-2H-1,2,4-benzothiadiazine-3(4H)-one 1,1-dioxide
mp: 165°–168° C.
IR (Nujol): 1700, 1610, 1580, 1460, 1340, 1170, 1140 cm$^{-1}$.

NMR (DMSO-d$_6$, δ): 3.52 (3H, s), 3.95 (3H, s), 7.02 (1H, dd, J=2 Hz and 9 Hz), 7.10 (1H, d, J=2 Hz), 7.65 (2H, d, J=7 Hz), 7.92 (1H, d, J=9 Hz), 7.98 (2H, d, J=7 Hz).

(4) 2-(3,4-Dichlorophenyl)-6-methoxy-4-methyl-2H-1,2,4-benzothiadiazine-3(4H)-one 1,1-dioxide
mp: 150°–151° C.
IR (Nujol): 1710, 1600, 1460, 1340, 1320, cm$^{-1}$.
NMR (DMSO-$_6$, δ): 3.50 (3H, s), 3.95 (3H, s), 7.02 (1H, d, J=9 Hz), 7.06 (1H, s), 7.45 (1H, d, J=8 Hz), 7.70–8.00 (3H, m).

(5) 2-(4-Fluorophenyl)-6-methoxy-4-methyl-2H-1,2,4-benzothiadiazine-3 (4H)-one 1,1-dioxide
mp: 203°–204° C.
IR (Nujol): 1700, 1590, 1440 cm$^{-1}$.

NMR (DMSO-d$_6$, δ): 3.52 (3H, s), 3.95 (3H, s), 7.02 (1H, d, J=9 Hz), 7.10 (1H, s), 7.30–7.60 (4H, m), 7.90 (1H, d, J=9 Hz).

(6) 6-Isopropoxy-2-(4-methoxyphenyl)-4-methyl-2H-1,2,4-benzothiadiazine-3(4H)-one 1,1-dioxide
mp: 182°–183° C.
IR (Nujol): 1690, 1600, 1460, 1370, 1340 cm$^{-1}$.

NMR (DMSO-d$_6$, δ): 1.34 (6H, d, J=6 Hz), 3.50 (3H, s), 3.82 (3H, s), 4.89 (1H, m), 7.00–7.08 (4H, m), 7.25–7.32 (2H, m), 7.84 (1H, d, J=9 Hz).

(7) 2-(4-Chlorophenyl)-4-methyl-2H-1,2,4-benzothiadiazine-3(4H)-one 1,1-dioxide
mp: 178°–180° C.
IR (Nujol): 1690, 1600, 1500, 1470, 1450, 1350, 1270, 1180, 1140 cm$^{-1}$.

NMR (DMSO-d$_6$, δ): 3.53 (3H, s), 7.40–8.00 (8H, m).

(8) 6-Chloro-2-(4-chlorophenyl)-4-methyl-2H-1,2,4-benzothiadiazine-3(4H)-one 1,1-dioxide
mp: 154°–157° C.
IR (Nujol): 1700, 1590, 1560, 1460, 1340, 1310, 1180 cm$^{-1}$.

NMR (DMSO-d$_6$, δ): 3.51 (3H, s), 7.43 (2H, d, J=8 Hz), 7.52 (1H, dd, J=1 Hz and 8 Hz), 7.57 (2H, d, J=8 Hz), 7.78 (1H, d, J=1 Hz), 8.00 (1H, d, J=8 Hz).

(9) 2-(2-Chlorophenyl)-6-methoxy-4-methyl-2H-1,2,4-benzothiadiazine-3(4H)-one 1,1-dioxide
mp: 155°–156° C.
IR (Nujol): 1710, 1600, 1460, 1330, 1300, 1180, 1140 cm$^{-1}$.

NMR (DMSO-d$_6$, δ): 3.54 (3H, s), 3.95 (3H, s), 7.03 (1H, dd, J=2 Hz and 9 Hz), 7.11 (1H, d, J=2 Hz), 7.50–7.70 (4H, m), 7.90 (1H, d, J=9 Hz).

(10) 2-(3-Chlorophenyl)-6-methoxy-4-methyl-2H-1,2,4-benzothiadiazine-3(4H)-one 1,1-dioxide
mp: 153°–154° C.
IR (Nujol): 1710, 1600, 1590, 1460, 1340, 1320, 1180, 1130, 1060, 1030 cm$^{-1}$.

NMR (DMSO-d$_6$, δ): 3.51 (3H, s), 3.94 (3H, s), 7.02 (1H, dd, J=2 Hz and 9 Hz), 7.07 (1H, d, J=2 Hz), 7.34–7.65 (4H, m), 7.90 (1H, d, J=9 Hz).

(11) 6-Isopropoxy-4-methyl-2-(p-tolyl)-2H-1,2,4-benzothiadiazine-3(4H)-one 1,1-dioxide
mp: 163°–165° C.
IR (Nujol): 1690, 1600, 1580, 1340, 1320, 1130, 1110 cm$^{-1}$.

NMR (DMSO-d$_6$, δ): 1.33 (3H, s), 1.36 (3H, s), 2.38 (3H, s), 3.49 (3H, s), 4.90 (1H, m), 6.90–7.10 (2H, m), 7.20–7.34 (4H, m), 7.84 (1H, d, J=8 Hz).

(12) 6-Isopropoxy-4-methyl-2-phenyl-2H-1,2,4-benzothiadiazine-3(4H)-one 1,1-dioxide
mp: 134°–135° C.
IR (Nujol): 1690, 1600, 1580, 1450, 1340, 1190 cm$^{-1}$.
NMR (CDCl$_3$, δ): 1.42 (6H, d, J=6 Hz), 3.55 (3H, s), 4.70 (1H, m), 6.70–7.90 (2H, m), 7.35–7.60 (5H, m), 7.82 (1H, d, J=9 Hz).

(13) 2-(3,4-Dichlorophenyl)-6-isopropoxy-4-methyl-2H-1,2,4-benzothiadiazine-3(4H)-one 1,1-dioxide
mp: 109°–110° C.
IR (Nujol): 1710, 1570, 1460, 1350, 1320 cm$^{-1}$.
NMR (DMSO-d$_6$, δ): 1.34 (6H, d, J=5 Hz), 3.49 (3H, s), 4.90 (1H, m), 7.01 (1H, d, J=8 Hz), 7.03 (1H, s), 7.45 (1H, d, J=9 Hz), 7.74–7.89 (3H, m).

(14) 2-(4-Fluorophenyl)-6-isopropoxy-4-methyl-2H-1,2,4-benzothiadiazine-3(4H)-one 1,1-dioxide
mp: 139°–140° C.
IR (Nujol): 1700, 1600, 1570, 1460, 1380, 1330, 1210 cm$^{-1}$.
NMR (DMSO-d$_6$, δ): 1.33 (6H, d, J=6 Hz), 3.50 (3H, s), 4.90 (1H, m), 6.98–7.02 (2H, m), 7.30–7.48 (4H, m), 7.85 (1H, d, J=9 Hz).

(15) 2-(4-Chlorophenyl)-6-ethoxy-4-methyl-2H-1,2,4-benzothiadiazine-3(4H)-one 1,1-dioxide
mp: 150°–151° C.
IR (Nujol): 1680, 1600, 1580, 1460, 1350, 1320, 1220, 1190, 1130 cm$^{-1}$.
NMR (DMSO-d$_6$, δ): 1.39 (3H, t, J=7 Hz), 3.50 (3H, s), 4.23 (2H, q, J=7 Hz), 7.00 (1H, dd, J=2 Hz and 9 Hz), 7.05 (1H, d, J=2 Hz), 7.40–7.63 (4H, m), 7.87 (1H, d, J=9 Hz).

(16) 6-Benzyloxy-2-(4-chlorophenyl)-4-methyl-2H-1,2,4-benzothiadiazine-3(4H)-one 1,1-dioxide
mp: 174°–175° C.
IR (Nujol): 1690, 1600, 1590, 1460, 1320, 1310, 1180 cm$^{-1}$.
NMR (DMSO-d$_6$, δ): 3.34 (3H, s), 5.32 (2H, s), 7.07 (1H, dd, J=(Hz, 2 Hz), 7.20 (1H, d, J=2 Hz), 7.30–7.63 (9H, m), 7.90 (1H, d, J=9 Hz).

(17) 2-(4-Chlorophenyl)-6-cyclopropylmethoxy-4-methyl-2H-1,2,4-benzothiadiazine-3(4H)-one 1,1-dioxide
mp: 145°–146° C.
IR (Nujol): 1690, 1600, 1580, 1540, 1330 cm$^{-1}$.
NMR (DMSO-d$_6$, δ): 0.30–0.45 (4H, m), 1.30 (1H, m), 3.45 (3H, s), 4.01 (2H, d, J=7 Hz), 6.90–7.10 (2H, m), 7.35–7.70 (4H, m), 7.85 (1H, d, J=9 Hz).

(18) 2-(2-Chloropheny))-6-isopropoxy-4-methyl-2H-1,2,4-benzothiadiazine-3(4H)-one 1,1-dioxide
mp: 150°–152° C.
IR (Nujol): 1700, 1600, 1580, 1450, 1360, 1320, 1200 cm$^{-1}$.
NMR (DMSO-d$_6$, δ): 1.34 (6H, d, J=6 Hz), 3.52 (3H, s), 4.90 (1H, m), 6.95–7.10 (2H, m), 7.50–7.70 (4H, m), 7.86 (1H, d, J=9 Hz).

(19) 2 (3-Chlorophenyl)-6-isopropoxy-4-methyl-2H-1,2,4-benzothiadiazine-3(4H)-one 1,1-dioxide
mp: 126°–127° C.
IR (Nujol): 1700, 1600, 1590, 1380, 1330, 1310, 1180 cm$^{-1}$.
NMR (DMSO-d$_6$, δ): 1.34 (6H, d, J=6 Hz), 3.49 (3H, s), 4.90 (1H, m), 6.98–7.03 (2H, m), 7.37–7.65 (4H, m), 7.86 (1H, d, J=9 Hz).

(20) 2-(4-Chlorophenyl)-4-methyl-6-propoxy-2H-1,2,4-benzothiadiazine-3(4H)-one 1,1-dioxide
mp: 142°–143° C.
IR (Nujol): 1700, 1690, 1610, 1580, 1340, 1320 cm$^{-1}$.
NMR (DMSO-d$_6$, δ): 1.02 (3H, t, J=7 Hz), 1.80 (2H, q, J=7 Hz), 3.50 (3H, s), 4.10 (2H, t, J=7 Hz), 6.95–7.10 (2H, m), 7.40–7.70 (4H, m), 7.90 (1H, d, J=9 Hz).

(21) (6-Butoxy-2-(4-chlorophenyl)-4-methyl-2H-1,2,4-benzothiadiazine-3(4H)-one 1,1-dioxide
mp: 102°–103° C.
IR (Nujol): 1700, 1600, 1340, 1320, 1180, 1130 cm$^{-1}$.
NMR (DMSO-d$_6$, δ): 0.96 (3H, t, J=7 Hz), 1.35–1.90 (4H, m), 3.50 (3H, s), 4.18 (2H, t, J=7 Hz), 6.95–7.10 (2H, m), 7.35–7.70 (4H, m), 8.90 (1H, d, J=9 Hz).

(22) 2-(4-Chlorophenyl)-6-isopropoxy-4-methyl-2H-1,2,4-benzothiadiazine-3(4H)-one 1,1-dioxide
mp: 157°–159° C.
IR (Nujol): 1700, 1605, 1460, 1330, 1320, 1300 cm$^{-1}$.
NMR (DMSO-d$_6$, δ): 1.32 (3H, s), 1.35 (3H, s), 3.50 (3H, s), 4.89 (1H, m), 7.00 (1H, d, J=9 Hz), 7.02 (1H, s), 7.35–7.60 (4H, m), 7.85 (1H, d, J=9 Hz).

(23) 2-(4-Trifluoromethylphenyl)-4-methyl-6-isopropoxy-2H-1,2,4-benzothiadiazine-3(4H)-one 1,1-dioxide
mp: 158°–160° C.
IR (nujol): 1690, 1600, 1460, 1370, 1320, 1130 cm$^{-1}$.
NMR (DMSO-d$_6$, δ): 1.34 (6H, d, J=6 Hz), 3.50 (3H, s), 4.90 (1H, m), 7.00–7.10 (2H, m), 7.64 (2H, d, J=7 Hz), 7.80–8.00 (3H, m).

(24) 2-(4-Chlorophenyl)-4-methyl-6-(2-methylpropoxy)--2H-1,2,4-benzothiadiazine-3(4H)-one 1,1-dioxide
mp: 108°–110° C.
IR (Nujol): 1690, 1600, 1580, 1460, 1340, 1320, 1190 cm$^{-1}$.
NMR (DMSO-d$_6$, δ): 1.02 (6H, d, J=7 Hz), 2.08 (1H, m), 3.51 (3H, s), 3.95 (2H, d, J=8 Hz), 6.99–7.06 (2H, m), 7.39–7.63 (4H, m), 7.87 (1H, d, J=9 Hz).

(25) 2-(4-Chlorophenyl)-4-methyl-6-cyclohexylmethoxy-2H-1,2,4-benzothiadiazine-3(4H)-one 1,1-dioxide
mp: 127°–129° C.
IR (Nujol): 1690, 1600, 1590, 1460, 1320, 1310, 1180, 1130 cm$^{-1}$.
NMR (DMSO-d$_6$, δ): 1.04–1.40 (5H, m), 1.50–1.90 (6H, m), 3.50 (3H, s), 3.98 (2H, d, J=6 Hz), 6.98–7.05 (2H, m), 7.38–7.63 (4H, m), 7.86 (1H, d, J=9 Hz).

(26) 2-(4-Chlorobenzyl)-6-methoxy-4-methyl-2H-1,2,4-benzothiadiazine-3(4H)-one 1,1-dioxide
mp: 132°–133° C.
IR (Nujol): 1675, 1600, 1350, 1330, 1195 cm$^{-1}$.
NMR (DMSO-d$_6$, δ): 3.47 (3H, s), 3.92 (3H, s), 4.96 (2H, s), 6.98 (1H, d, J=9.0 Hz), 7.00 (1H, s), 7.35 and 7.40 (4H, ABq, J=8.7 Hz), 7.87 (1H, d, J=9.0 Hz).

(27) 2-(4-Chlorophenyl)-6-carboxymethoxy-4-methyl-2H-1,2,4-benzothiadiazine-3(4H)-one 1,1-dioxide
mp: 228°–230° C.
IR (Nujol): 1730, 1690, 1600, 1460, 1340, 1320 cm$^{-1}$.
NMR (DMSO-d$_6$, δ): 3.34 (1H, brs), 3.50 (3H, s), 4.95 (2H, s), 6.99 (1H, dd, J=9 Hz and 2 Hz), 7.11 (1H, d, J=2 Hz), 7.35–7.65 (4H, m), 7.89 (1H, d, J=9 Hz).

(28) 2-(4-Chlorophenyl)-6-[1-(ethoxycarbonyl)]-ethoxy-4-methyl-2H-1,2,4-benzothiadiazine-3(4H)-one 1,1-dioxide ( R,S mixture )
mp: 111°–112° C.
IR (Nujol): 1750, 1690, 1605, 1340, 1210, 1140 cm$^{-1}$.
NMR (CDCl$_3$, δ): 1.29 (3H, t, J=7.1 Hz), 1.69 (3H, d, J=6.7 Hz), 3.52 (3H, s), 4.26 (2H, q, J=7.1 Hz), 4.88 (1H, q, J=6.7 Hz), 6.73 (1H, dd, J=8.7 Hz and 2.0 Hz), 6.84 (1H, d, J=2.0 Hz), 7.35 and 7.46 (4H, ABq, J=8.6 Hz), 7.83 (1H, d, J=8.7 Hz).

(29) 2-(4-Chlorophenyl)-6-(1-carboxyehtoxy)-4-methyl-2H-1,2,4-benzothiadiazine-3(4H)-one 1,1-dioxide mp: 179.5°–180.5° C. (R,S mixture).

IR (Nujol): 3250, 1760, 1665, 1600, 1350 cm$^{-1}$.

NMR (CDCl$_3$, δ): 1.74 (3H, d, J=6.7 Hz), 3.52 (3H, s), 4.94 (1H, q, J=6.7 Hz), 5.54 (1H, brs), 6.76 (1H, dd, J=1.9 Hz and 8.7 Hz), 7.40 (4H, ABq, J=8.6 Hz), 7.85 (1H, d, J=8.7 Hz).

(30) 2-(4-Chlorophenyl)-6-(1-ethoxycarbonyl-1-methyl ethoxy)-4-methyl-2H-1,2,4-benzothiadiazine(3(4H)-one 1,1dioxide mp: 184°–185° C.

IR (Nujol): 1720, 1700, 1580, 1370, 1340 cm$^{-1}$.

NMR (CDCl$_3$, δ): 1.30 (3H, t, J=7 Hz), 1.73 (6H, s), 3.53 (3H, s), 4.28 (2H, q, J=7 Hz), 6.68 (1H, dd, J=9 Hz and 2 Hz), 6.80 (1H, d, J=2 Hz), 7.37 (2H, d, J=9 Hz), 7.50 (2H, d, J=9 Hz), 7.81 (1H, d, J=9 Hz).

(31) 2-(4-Chlorophenyl)-6-(3-ethoxycarbonylpropoxy)-4-methyl-2H-1,2,4-benzothiadiazine-3(4H)-one 1,1-dioxide mp: 90°–92° C.

IR (Nujol): 1730, 1700, 1600, 1580, 1470, 1330, 1320 cm$^{-1}$.

NMR (CDCl$_3$, δ): 1.28 (3H, t, J=7 Hz), 2.17 (2H, m), 2.54 (2H, t, J=7 Hz), 3.54 (3H, s), 4.15 (2H, t, J=7 Hz), 4.17 (2H, q, J=7 Hz), 6.70–6.90 (2H, m), 7.30–7.55 (4H, m), 7.84 (1H, d, J=9 Hz).

(32) 2-(4-Chlorophenyl)-6-(1-ethoxycarbonylpropoxy)-4-methyl-2H-1,2,4-benzothiadiazine-3(4H)-one 1,1-dioxide mp: 105°–108° C.

IR (Nujol): 1750, 1690, 1600, 1580, 1210 cm$^{-1}$.

NMR (CDCl$_3$, δ): 1.11 (3H, t, J=7 Hz), 1.29 (3H, t, J=7 Hz), 2.06 (2H, m), 3.50 (3H, s), 4.26 (2H, q, J=7 Hz), 4.69 (1H, t, J=6 Hz), 6.74 (1H, dd, J=9 Hz and 6 Hz), 6.84 (1H, d, J=2 Hz), 7.30–7.50 (4H, m), 7.83 (1H, d, J=9 Hz).

(33) 2-(4-Chlorophenyl)-6-(1-ethoxycarbonylcyclobutyloxy)-4-methyl-2H-1,2,4-benzothiadiazine-3(4H)-one 1,1dioxide mp: 140°–142° C.

IR (Nujol): 1730, 1690, 1610, 1590, 1360 cm$^{-1}$.

NMR (CDCl$_3$, δ): 1.69 (3H, t, J=7 Hz), 1.85–2.90 (6H, m), 3.46 (3H, s), 4.20 (2H, q, J=7 Hz), 6.57 (1H, dd, J=9 Hz and 2 Hz), 6.92 (1H, d, J=2 Hz), 7.41 (2H, d, J=8 Hz), 7.60 (2H, d, J=8 Hz), 7.87 (1H, d, J=9 Hz).

(34) 2-(4-Chlorophenyl)-6-(1-carboxy-1-methylethoxy)-4-methyl-2H-1,2,4-benzothiadiazine-3(4H)-one 1,1-dioxide mp: 208°–210° C.

IR (Njuol): 3250, 1750, 1670, 1600, 1350, 1330 cm$^{-1}$.

NMR (CDCl$_3$, δ): 1.75 (6H, s), 3.51 (3H, s), 6.74 (1H, dd, J=9 Hz and 2 Hz), 6.83 (1H, d, J=2 Hz), 7.34 (2H, d, J=9 Hz), 7:46 (2H, d, J=9 Hz, 7.82 (1H, d, J=9 Hz).

(35) 2-(4-Chlorophenyl)-6-(3-carboxypropoxy)-4-methyl-2H-1,2,4-benzothiadiazine-3(4H)-one 1,1-dioxide mp: 170°–171° C.

IR (Nujol): 1700, 1600, 1580, 1330, 1310 cm$^{-1}$.

NMR (CDCl$_3$, δ): 2.19 (2H, m), 2.62 (2H, t, J=7 Hz), 3.54 (3H, s), 4.17 (2H, t, J=6 Hz), 6.70–6.90 (2H, m), 7.35 (2H, d, J=9 Hz), 7.47 (2H, d, J=9 Hz), 7.84 (1H, d, J=9 Hz).

(36) 2-(4-Chlorophenyl)-6-(1-carboxypropoxy)-4-methyl-2H-1,2,4-benzothiadiazine-3(4H)-one 1,1-dioxide mp: 179°–181° C.

IR (Nujol): 3250, 1760, 1680, 1600, 1590, 1380, 1200 cm$^{-1}$.

NMR (CDCl$_3$, δ): 1.15 (3H, t, J=7 Hz), 2.11 (2H, m), 3.53 (3H, s), 4.78 (1H, t, J=6 Hz), 6.76 (1H, dd, J=9 Hz and 2 Hz), 6.86 (1H, d, J=2 Hz), 7.30-7.50 (4H, m), 7.85 (1H, d, J=9 Hz).

(37) 2-(4-Chlorophenyl)-6-(1-carboxycyclobutyloxy)-4-methyl-2H-1,2,4-benzothiadiazine-3(4H)-one 1,1-dioxide mp: 148°–151° C.

IR (Nujol): 1700, 1600, 1380, 1320, 1180 cm$^{-1}$.

NMR (CDCl$_3$, δ):2.00–2.30 (2H, m), 2.50–2.75 (2H, m), 2.78–2.95 (2H,m), 3.51 (3H, s), 6.53 (1H, dd, J=9 Hz and 2 Hz), 6.73 (1H, d, J=2 Hz), 7.34 (2H, d, J=9 Hz), 7.46 (2H, d, J=9 Hz), 7.80 (1H, d, J=9 Hz).

(38) 4-Isopropyl-2-(4-Chlorophenyl)-6-methoxy-2H-1,2,4-benzothiadiazine-3(4H)-one 1,1-dioxide mp: 166°–168° C.

IR (Nujol): 1690, 1600, 1570, 1460, 1340, 1300 cm$^{-1}$.

NMR (DMSO-d$_6$, δ): 1.54 (6H, d, J=6 Hz), 3.94 (3H, s), 4.61 (1H, m), 6.90–7.10 (2H, m), 7.30–7.70 (4H, m), 7.85 (1H, d, J=9 Hz)

(39) 2-(4-Chlorophenyl)-6-isopropoxy-4-isopropyl-2H-1,2,4-benzothiadiazine-3(4H)-one 1,1-dioxide mp: 158°–160° C.

IR (Nujol): 1690, 1590, 1490, 1460, 1340, 1300 cm$^{-1}$.

NMR (DMSO-d$_6$, δ): 1.34 (6H, d, J=6 Hz), 1.52 (6H, d, J=6 Hz), 4.58 (1H, m), 4.88 (1H, m), 6.90–7.05 (2H, m), 7.30–7.65 (4H, m), 7.82 (1H, d, J=9 Hz).

(40) 2-(4-Chlorophenyl)-4-ethyl-6-methoxy-2H-1,2,4-benzothiadiazine-3(4H)-one 1,1-dioxide mp: 106°–107° C.

IR (Nujol): 1690, 1600, 1570, 1490, 1460, 1350, 1310 cm$^{-1}$.

NMR (DMSO-D$_6$, δ): 1.28 (3H, t, J=7 Hz), 3.95 (3H, s), 4.14 (2H, q, J=7 Hz), 7.03 (1H, d, J=9 Hz), 7.09 (1H, s), 7.42 (2H, d, J=9 Hz), 7.60 (2H, d, J=9 Hz), 7.90 (1H, d, J=9 Hz).

(41) 2-(4-Chlorophenyl)-4-ethyl-6-isopropoxy-2H-1,2,4-benzothiadiazine-3(4H)-one 1,1-dioxide mp: 167°–168° C.

IR (Nujol): 1700, 1600, 1580, 1460, 1340, 1310 cm$^{-1}$.

NMR (DMSO-d$_6$, δ): 1.26 (3H, t, J=7 Hz), 1.34 (6H, d, J=6 Hz), 4.13 (2H, q, J=7 Hz), 7.05–7.09 (2H, m), 7.42 (2H, d, J=9 Hz), 7.60 (2H, d, J=9 Hz), 7.87 (2H, d, J=9 Hz).

(42) (1R)-(+)-2-(4-Chlorophenyl)-6-[1-(ethoxycarbonyl)ethoxy]-4-methyl-2H-1,2,4-benzothiadiazine-3(4H)-one 1,1-dioxide mp: 86°–88° C.

[α]$_D$ +24.0° (C=1.0,EtOH).

IR (Nujol): 1740, 1690, 1680, 1600, 1590, 1500, 1210, 1185 cm$^{-1}$.

NMR (CDCl$_3$, δ): 1.30 (3H, t, J=7 Hz), 1.69 (3H, d, J=7 Hz), 3.53 (3H, s), 4.26 (2H, q, J=7 Hz), 4.87 (1H, q, J=7 Hz), 6.74 (1H, dd, J=2 Hz and 9 Hz), 6.83 (1H, d, J=9 Hz), 7.35 (2H, d, J=9 Hz), 7.46 (2H, d, J=9 Hz), 7.83 (1H, d, J=9 Hz).

(43) (1S)-(−)-2-(4-Chlorophenyl)-6-[1-(ethoxycarbonyl)ethoxy]-4-methyl-2H-1,2,4-benzothiadiazine-3(4H)-one 1,1-dioxide mp: 96°–98° C.

[α]$_D$ −24.7° (C=1.0, EtOH).

IR (Nujol): 1730, 1690, 1680, 1600, 1590, 1340, 1190 cm$^{-1}$.

NMR (CDCl$_3$, δ): 1.29 (3H, t, J=7 Hz), 1.69 (3H, d, J=7 Hz), 3.52 (3H, s), 4.26 (2H, q, J=7 Hz), 4.88 (1H, q, J=7 Hz), 6.74 (1H, d, J=9 Hz), 6.83 (1H, s), 7.35 (2H, d, J=9 Hz), 7.46 (2H, d, J=9 Hz), 7.83 (1H, d, J=9 Hz).

(44) (1R)-(+)-2-(4-Chlorophenyl)-6-(1-carboxyethoxy) 4-methyl-2H-1,2,4-benzothiadiazine-3(4H)-one 1,1-dioxide mp: 75°–85° C. $[\alpha]_D+16.4°$ (C=1.0, EtOH).

IR (Nujol): 3200, 1740, 1700, 1690, 1660, 1600, 1580, 1380, 1130 cm$^{-1}$.

NMR (CDCl$_3$, δ): 1.77 (3H, d, J=7 Hz), 3.55 (3H, s), 4.98 (1H, q, J=7 Hz), 6.79 (1H, dd, J=2 Hz and 9 Hz), 6.88 (1H, d, J=2 Hz), 7.37 (2H, d, J=9 Hz), 7.49 (2H, d, J=9 Hz), 7.88 (1H, d, J=9 Hz).

(45) (1S)-(−)-2-(4-Chlorophenyl)-6-(1-carboxyethoxy-)-4-methyl-2H-1,2,4-benzothiadiazine-3(4H)-one 1,1-dioxide mp: 85°–95° C.

$[\alpha]_D-17.0°$ (C=1.0, EtOH).

IR (Nujol): 3200, 1740, 1700, 1665, 1600, 1580, 1200, 1130 cm$^{-1}$.

NMR (CDCl$_3$, δ): 1.75 (3H, d, J=7 Hz), 3.52 (3H, s), 4.95 (1H, q, J=7 Hz), 6.50 (1H, bs), 6.75 (1H, dd, J=2 Hz and 9 Hz), 6.88 (1H, d, J=2 Hz), 7.32 (2H, d, J=9 Hz), 7.45 (2H, d, J=9 Hz), 7.85 (1H, d, J=9 Hz).

(46) 2-Cyclohexyl-6-methoxy-4-methyl-2H-1,2,4-benzothiadiazine-3(4H)-one 1,1-dioxide mp: 124.5°–126° C.

IR (Nujol): 1690, 1595, 1325, 1310, 1300, 1175 cm$^{-1}$.

NMR (DMSO-d$_6$, δ): 1.0–1.5 (3H, m), 1.55–1.9 (5H, m), 2.05–2.35 (2H, m), 3.45 (3H, s), 3.90 (3H, s), 4.15–4.4 (1H, m), 6.95 (1H, d, J=8.3 Hz), 6.97 (1H, s), 7.78 (1H, d, J=8.3 Hz).

(47) 6-Isopropoxy-4-methyl-2-(2-pyridyl)-2H-1,2,4-benzothiadiazine-3(4H)-one 1,1-dioxide mp: 173°–174° C.

IR (Nujol): 1700, 1600, 1590, 1340, 1215 cm$^{-1}$.

NMR (CDCl$_3$, δ): 1.40 (6H, d, J=6 Hz), 3.53 (3H, s), 4.6–4.8 (1H, m), 6.73–6.85 (2H, m), 7.35–7.55 (2H, m), 7.82 (1H, d, J=8.7 Hz), 7.8–7.95 (1H, m), 8.6–8.68 (1H, m).

(48) 6-Methoxy-4-methyl-2-pentyl-2H-1,2,4-benzothiadiazine-3(4H)-one 1,1-dioxide mp: 85°–88° C.

IR (Nujol): 1690, 1600, 1450, 1330, 1310, 1180 cm$^{-1}$.

NMR (DMSO-d$_6$, δ): 0.84 (3H, t, J=6 Hz), 1.10–1.40 (4H, m), 1.50–1.75 (2H, m), 3.47 (3H, s), 3.75 (2H, t, J=7 Hz), 3.91 (3H, s), 6.90–7.05 (2H, m), 7.82 (1H, d, J=9 Hz).

(49) 2-(4-Chlorophenyl)-4-methyl-6-(N-methylacetylamino)-2H-1,2,4-benzothiadiazine-3(4H)-one 1,1-dioxide mp: 168°–172° C.

IR (Nujol): 1690, 1655, 1590, 1340 cm$^{-1}$.

NMR (CDCl$_3$, δ): 2.09 (3H, s), 3.38 (3H, s), 3.57 (3H, s) 7.10–7.55 (6H, m), 7.95–8.05 (1H, m).

(50) 6-Methoxy-2-(4-methoxycarbonylphenyl)-4-methyl-2H-1,2,4-benzothiadiazine-3(4H)-one 1,1-dioxide mp: 153°–156° C.

IR (Nujol): 1725, 1690, 1590, 1320, 1280 cm$^{-1}$.

NMR (DMSO-d$_6$, δ): 3.52 (3H, s), 3.89 (3H, s), 3.95 (3H, s), 6.97–7.13 (2H, m), 7.55 and 8.10 (4H, ABq, J=8.3 Hz), 7.90 (1H, d, J=8.8 Hz).

(51) 6-Cyclohexylmethoxy-4-methyl-2-(2-pyridyl)-2H-1,2,4-benzothiadiazine-3(4H)-one 1,1-dioxide mp: 161.5°–162.5° C.

IR (Nujol): 1700, 1600, 1310 cm$^{-1}$.

NMR (CDCl$_3$, δ): 0.95–1.45 (5H, m), 1.65–2.0 (6H, m), 3.54 (3H, s), 3.86 (2H, d, J=6 Hz), 6.73–6.85 (2H, m), 7.35–7.55 (2H, m), 7.82 (1H, d, J=8.5 Hz), 7.81–7.95 (1H, m), 8.6–8.67 (1H, m).

(52) 2-(4-Methoxycarbonylmethylphenyl)-6-methoxy-4-methyl-2H-1,2,4-benzothiadiazine-3(4H)-one 1,1-dioxide mp: 173°–176° C.

IR (Nujol): 1735, 1690, 1600, 1335, 1320 cm$^{-1}$.

NMR (DMSO-d$_6$, δ): 3.52 (3H, s), 3.65 (3H, s), 3.79 (2H, s), 3.95 (3H, s), 6.96–7.10 (2H, m), 7.33 and 7.43 (4H, ABq, J=8.3 Hz), 7.88 (1H, d, J=8.7 Hz).

(53) 2-(3-Ethoxycarbonylpropyl)-6-methoxy-4-methyl-2H-1,2,4-benzothiadiazine-3(4H)-one 1,1-dioxide mp: 63°–65° C.

IR (Nujol): 1740, 1690, 1600, 1480, 1380, 1360, 1340, 1320, 1180 cm$^{-1}$.

NMR (CDCl$_3$, δ) 1.23 (3H, t, J=7 Hz), 2.06 (2H, m), 2.37 (2H, t, J=7 Hz), 3.49 (3H, s), 3.90 (3H, s), 3.96 (2H, t, J=7 Hz), 4.09 (2H, q, J=7 Hz), 6.69 (1H, d, J=2 Hz), 6.80 (1H, dd, J=2 Hz and 9 Hz), 7.79 (1H, d, J=9 Hz).

(54) 2-(4-Chlorophenyl)-4,6-dimethyl-2H-1,2,4benzothiadiazine-3(4H)-one 1,1-dioxide mp: 164°–166° C.

IR (Nujol): 1700, 1600, 1490, 1350, 1330, 1280, 1180, 1090 cm$^{-1}$.

NMR (DMSO-d$_6$, δ): 2.50 (3H, s), 3.51 (3H, s), 7.28 (1H, d, J=8 Hz), 7.41 (2H, d, J=9 Hz), 7.50 (1H, s), 7.60 (2H, d, J=9 Hz), 7.84 (1H, d, J=8 Hz).

(55) 2-[2-(4,6-Dimethylpyridyl)]-6-isopropoxy-4-methyl-2H-1,2,4-benzothiadiazine-3(4H)-one 1,1-dioxide mp: 202°–203° C.

IR (Nujol): 1700, 1600, 1580, 1350, 1320, 1180 cm$^{-1}$.

NMR (DMSO-d$_6$, δ): 1.37 (6H, d, J=6 Hz), 2.34 (3H, s), 2.48 (3H, s), 3.49 (3H, s), 4.89 (1H, m), 7.01 (1H, d, J=9 Hz), 7.04 (1H, s), 7.13 (1H, s), 7.24 (1H, s), 7.80 (1H, d, J=9 Hz).

(56) 2-(4-Chlorophenyl)-4-methyl-6-trifluoromethyl-2H-1,2,4-benzothiadiazine-3(4H)-one 1,1-dioxide mp: 148°–150° C.

IR (Nujol): 1700, 1380, 1360, 1270, 1190, 1140, 1080 cm$^{-1}$.

NMR (DMSO-d$_6$, δ): 3.60 (3H, s), 7.45 (2H, d, J=9 Hz), 7.62 (2H, d, J=9 Hz), 7.81 (1H, d, J=8 Hz), 7.96 (1H, s), 8.21 (1H, d, J=8 Hz).

(57) 6-Isopropoxy-4-methyl-2-(2-pyrimidinyl)-2H-1,2,4-benzothiadiazine-3(4H)-one 1,1-dioxide mp: 176°–178° C.

IR (Nujol): 1700, 1600, 1400, 1380, 1350, 1330, 1280, 1230 cm$^{-1}$.

NMR (DMSO-d$_6$, δ): 1.33 (6H, d, J=6 Hz), 3.53 (3H, s), 4.90 (1H, m), 7.00 (1H, dd, J=2 Hz and 9 Hz), 7.10 (1H, t, J=7 Hz), 7.67 (1H, t, J=4 Hz), 7.84 (1H, t, J=9 Hz), 8.97 (2H, d, J=4 Hz).

(58) 6-Methoxy-4-methyl-2-(4-phenoxyphenyl)-2H-1,2,4-benzothiadiazine-3(4H)-one 1,1-dioxide mp: 184°–18° C.

IR (Nujol): 1690, 1590, 1330, 1180 cm$^{-1}$. NMR (DMSO-d$_6$, δ): 3.52 (3H, s), 3.94 (3H, s), 6.95–7.55 (11H, m), 7.89 (1H, d, J=9 Hz).

(59) 2-(4-Isopropylphenyl)-6-methoxy-4-methyl-2H-1,2,4-benzothiadiazine-3(4H)-one 1,1-dioxide mp: 158°–159° C.

IR (Nujol): 1700, 1595, 1330, 1310, 1125 cm$^{-1}$.

NMR (DMSO-d$_3$, δ): 1.24 (6H, d, J=7 Hz), 2.98 (1H, m), 3.51 (3H, s), 3.94 (3H, s), 7.01 (1H, dd, J=2 Hz and 9 Hz), 7.06 (1H, d, J=2 Hz), 7.27 and 7.39 (4H, ABq, J=8 Hz), 7.87 (1H, d J=9 Hz).

(60) 2-[(3-Chloro-4-methyl)phenyl]-6-methoxy-4-methyl-2H-1,2,4-benzothiadiazine-3(4H)-one 1,1-dioxide mp: 208°-211° C.

IR (Nujol): 1695, 1595, 1315, 1180 cm$^{-1}$.

NMR (DMSO-d$_3$, δ): 2.40 (3H, s), 3.51 (3H, s), 3.94 (3H, s), 7.02 (1H, dd, J=2 Hz and 9 Hz), 7.07 (1H, d, J=2 Hz), 7.39 (1H, dd, J=2 Hz and 8 Hz), 7.46 (1H, d, J=2 Hz), 7.52 (1H, d, J=8 Hz), 7.89 (1H, d, J=9 Hz).

(61) 6-Methoxy-4-methyl-2-(4-methylthiophenyl)-2H-1,2,4-benzothiadiazine-3(4H)-one 1,1-dioxide mp: 154°-155° C.

IR (Nujol): 1690, 1610, 1580, 1490, 1310, 1185 1135 cm$^{-1}$.

NMR (CDCl$_3$, δ): 2.51 (3H, s), 3.54 (3H, s), 3.93 (3H, s), 6.76 (1H, d, J=2 Hz), 6.83 (1H, dd, J=2 Hz and 9 Hz), 7.32 (4H, s), 7.85 (1H, d, J=9 Hz).

(62) 2-(4-Dimethylaminophenyl)-6-methoxy-4-methyl-2H-1,2,4-benzothiadiazine-3(4H)-one 1,1-dioxide mp: 244°-245° C.

IR (Nujol): 1690, 1600, 1520, 1330, 1310, 1180, 1130 cm$^{-1}$.

NMR (DMSO-d$_3$, δ): 2.96 (6H, s), 3.50 (3H, s), 3.94 (3H, s), 6.75 (2H, d, J=9 Hz), 7.10 (2H, d, J=9 Hz), 7.02 (1H, dd, J=2 Hz and 9 Hz), 7.02 (1H, d, J=2 Hz), 7.85 (1H, d, J=9 Hz).

(63) 2-(4-Chlorobenzyl)-6-isopropoxy-4-methyl-2H-1,2,4-benzothiadiazine-3(4H)-one 1,1-dioxide IR (Neat): 2980, 1680, 1600, 1580, 1330, 1180, 1110 cm$^{-1}$.

NMR(CDCl$_3$, δ): 1.38 (6H, d, J=6.0 Hz), 3.45 (3H, s), 4.55–4.75 (1H, m), 5.00 (2H, s), 6.65 (1H, d, J=1.9 Hz), 6.77 (1H, dd, J=1.9 and 8.8 Hz), 7.27 and 7.40 (4H, AB J=8.4 Hz), 7.80 (1H, d, J=8.8 Hz).

(64) 2-Cyclohexyl-6-isopropoxy-4-methyl-2H-1,2,4-benzothiadiazine-3(4H)-one 1,1-dioxide mp: 111°-112° C.

IR (Nujol): 1685, 1605, 1330, 1180, 1110 cm$^{-1}$.

NMR (DMSO-d$_6$, δ): 1.0–1.45 (3H, m), 1.31 (6H, d, J=6.0 Hz), 1.5–1.9 (5H, m), 2.05–2.35 (2H, m), 3.43 (3H, s), 4.25–4.4 (1H, m), 4.84 (1H, m), 6.91 (1H, s), 6.78 (1H, d, J=9.0 Hz), 7.75 (1H, d, J=9.0 Hz).

(65) 6-Isopropoxy-4-methyl-2-pentyl-2H-1,2,4-benzothiadiazine-3(4H)-one 1,1-dioxide mp: 44°-46° C.

IR (Nujol) 1690, 1600, 1580, 1460, 1340, 1320, 1190 cm$^{-1}$.

NMR (DMSO-d$_6$, δ): 0.84 (3H, t, J=6 Hz), 1.05–1.40 (4H, m), 1.31 (6H, d, J=6 Hz), 1.50–1.75 (2H, m), 3.44 (3H, s), 3.74 (2H, t, J=7 Hz), 4.85 (1H, m), 6.90–7.05 (2H, m), 7.78 (1H, d, J=9 Hz).

(66) 6-Isopropoxy-2-(4-isopropoxycarbonylphenyl)-4-methyl-2H-1,2,4-benzothiadiazine-3(4H)-one 1,1-dioxide mp: 128°-129° C.

IR (Nujol): 1720, 1710, 1610, 1340, 1280 cm$^{-1}$.

NMR (CDCl$_3$, δ): 1.38 (6H, d, J=6.8 Hz), 1.43 (6H, d, J=6.5 Hz), 3.54 (3H, s), 4.63–4.8 (1H, m), 5.2–5.35 (1H, m), 6.76 (1H, d, J=2 Hz), 6.82 (1H, dd, J=2 and 8.7 Hz), 7.50 and 8.15 (4H, ABq, J=8.4 Hz), 7.83 (1H, d, J=8.7 Hz).

(67) 2-(4-Isopropoxycarbonylmethylphenyl)-6-isopropoxy-4-methyl-2H-1,2,4-benzothiadiazine-3(4H)-one 1,1-dioxide mp: 117°-120° C.

IR (Nujol): 1730, 1690, 1595, 1335, 1325 cm$^{-1}$.

NMR (CDCl$_3$, δ): 1.24 (6H, d, J=6.0 Hz), 1.41 (6H, d, J=6.0 Hz), 3.52 (3H, s), 3.63 (2H, s), 4.6–4.8 (1H, m), 4.9–5.1 (1H, m), 6.7–6.85 (2H, m), 7.3–7.5 (4H, m), 7.75–7.80 (1H, m).

(68) 4-Isopropoxy-2-(3-isopropoxycarbonylpropyl)-4-methyl-2H-1,2,4-benzothiadiazine-3(4H)-one 1,1-dioxide IR (CHCl$_3$, δ) 1720, 1700, 1600, 1580, 1340, 1270, 1120 cm$^{-1}$.

NMR (CDCl$_3$, δ): 1.12 (6H, d, J=6 Hz), 1.30 (6H, d, J=6 Hz), 1.99 (2H, m), 2.28 (2H, t, J=7 Hz), 3.41 (3H, s), 3.90 (2H, t, J=7 Hz), 4.60 (1H, m), 4.92 (1H, m), 6.60 (1H, d, J=2 Hz), 6 70 (1H, dd, J=2 Hz and 9 Hz), 7.70 (1H, d, J=9 Hz).

(69) 2-(4-Chlorophenyl)-5,7-dichloro-6-isopropoxy-4-methyl-2H-1,2,4-benzothiadiazine-3(4H)-one 1,1-dioxide mp: 185°-188° C.

IR (Nujol) 1710, 1470, 1380, 1360, 1190 cm$^{-1}$.

NMR (DMSO-d$_6$, δ): 1.38 (6H, d, J=6 Hz), 3.33 (3H, s), 4.75 (1H, m), 7.44 (2H, d, J=9 Hz), 7.61 (2H, d, J=9 Hz), 8.14 (1H, s).

(70) (1R)-(+)-6-[1-(Ethoxycarbonyl)ethoxy]-4-methyl-2-phenyl-2H-1,2,4-benzothiadiazine-3(4H)-one 1,1dioxide mp: 137.5°-139° C.

IR (Nujol): 1740, 1700, 1605, 1340, 1210, 1140 cm$^{-1}$.

NMR (CDCl$_3$, δ): 1.30 (3H, t, J=7 Hz), 1.69 (3H, d, J=7 Hz), 3.53 (3H, s), 4.26 (2H, q, J=7 Hz), 4.88 (1H, q, J=7 Hz), 6.73 (1H, dd, J=2 Hz and 9 Hz), 6.84 (1H, d, J=2 Hz), 7.35–7.55 (5H, m), 7.84 (1H, d, J=9 Hz).

(71) (1R)-(+)-6-[1-(Ethoxycarbonyl)ethoxy]-4-methyl-2-(4-phenoxyphenyl)-2H-1,2,4-benzothiadiazine-3(4H)-one 1,1-dioxide mp: 128°-130° C.

IR (Nujol): 1740, 1685, 1610, 1330, 1195, 1130 cm$^{-1}$.

NMR (CDCl$_3$, δ): 1.29 (3H, t, J=7 Hz), 1.69 (3H, d, J=7 Hz), 3.53 (3H, s), 4.26 (2H, q, J=7 Hz), 4.88 (1H, q, J=7 Hz), 6.75 (1H, dd, J=2 Hz and 9 Hz), 6.83 (1H, d, J=2 Hz), 7.0–7.45 (9H, m), 7.85 (1H, d, J=9 Hz).

(72) (1R)-(+)-6-[1-(Ethoxycarbonyl)ethoxy]-2-(4-isopropylphenyl)-4-methyl-2H-1,2,4-benzothiadiazine-3(4H)-one 1,1-dioxide mp: 154°-155° C.

IR (Nujol): 1740, 1695, 1600, 1340, 1310, 1200, 1130 cm$^{-1}$.

NMR (CDCl$_3$, δ): 1.27 (6H, d, J=7 Hz), 1.29 (3H, t, J=7 Hz), 1.69 (3H, d, J=7 Hz), 2.95 (1H, m), 3.52 (3H, s), 4.26 (2H, q, J=7Hs), 4.88 (1H, q, J=7 Hz), 6.73 (1H, dd, J=2 Hz and 9 Hz), 6.83 (1H, d, J=2 Hz), 7.32 (4H, s), 7.83 (1H, d, J=9 Hz).

(73) (1R)-(+)-2-[(3-Chloro-4-methyl)phenyl]-6-[1(ethoxycarbonyl)ethoxy]-4-methyl-2H-1,2,4-benzothiadiazine-3(4H)-one 1,1-dioxide mp: 149°-150° C.

IR (Nujol): 1740, 1685, 1600, 1335 cm$^{-1}$.

NMR (DMSO-d$_6$, δ): 1.21 (3H, t, J=7 Hz), 1.58 (3H, d, J=7 Hz), 2.40 (3H, s), 3.48 (3H, s), 4.18 (2H, q, J=7 Hz), 5.33 (1H, q, J=7 Hz), 6.95 (1H, dd, J=2 Hz and 9 Hz), 7.08 (1H, d, J=2 Hz), 7.30 (1H, dd, J=2 Hz and 8 Hz), 7.47 (1H, d, J=2 Hz), 7.51 (1H, d, J=8 Hz), 7.87 (1H, d, J=9 Hz).

(74) (1R)-(+)-2-Cyclohexyl-6-[1-(ethoxycarbonyl)ethoxy]-4-methyl-2H-1,2,4-benzothiadiazine-3(4H)-one 1,1-dioxide mp: 139°-141° C.

IR (Nujol): 1740, 1690, 1600, 1580, 1340, 1300, 1200, 1170 cm$^{-1}$.

NMR (CDCl$_3$, δ): 1.28 (3H, t, J=6 Hz), 1.16–1.45 (3H, m), 1.66 (3H, d, J=6 Hz), 1.80–1.92 (5H, m), 2.22–2.42 (2H, m), 3.44 (3H, s), 4.23 (2H, q, J=6 Hz), 4.29–4.49 (1H, m), 4.83 (1H, q, J=6 Hz), 6.65 (1H, dd, J=2 Hz and 8 Hz), 6.71 (1H, d, J=2 Hz), 7.74 (1H, d J=6 Hz).

(75) (1R)-(+)-6-[1-(Ethoxycarbonyl)ethoxy]-4-methyl-2-(4-methylphenyl)-2H-1,2,4-benzothiadiazine-3(4H)-one 1,1-dioxide mp: 134°–135° C.

IR (Nujol): 1740, 1680, 1600, 1580, 1340, 1320, 1200, 1130 cm$^{-1}$.

NMR (CDCl$_3$, δ): 1.3 (3H, t, J=6 Hz), 1.69 (3H, d, J=6 Hz), 2.40 (3H, s), 3.52 (3H, s), 4.25 (2H, q, J=6 Hz), 4.88 (1H, q, J=6 Hz), 6.70 (1H, dd, J=2 Hz and 8 Hz), 6.82 (1H, d, J=2 Hz), 7.28 (4H, s), 7.83 (1H, d, J=8 Hz).

(76) (1R)-(+)-6-[1-(Ethoxycarbonyl)ethoxy]-4-methyl-2-(2-pyridyl)-2H-1,2,4-benzothiadiazine-3(4H)-one 1,1-dioxide mp: 153°–154° C.

IR (Nujol): 1740, 1690, 1605, 1580, 1460, 1330, 1205, 1115 cm$^{-1}$. NMR (CDCl$_3$, δ) 1.29 (3H, t, J=7 Hz), 1.69 (3H, d, J=7 Hz), 3.52 (3H, s), 4.25 (2H, q, J=7 Hz), 4.86 (1H, q, J=7 Hz), 6.72 (1H, dd, J=2 Hz and 8 Hz), 6.84 (1H, d, J=2 Hz), 7.38–7.51 (2H, m), 7.82 (1H, d, J=8 Hz), 7.90 (1H, dd, J=2 Hz and 8 Hz), 8.62–8.66 (1H, m).

(77) (1R)-(+)-2-(3,4-Dichlorophenyl)-6-[1-(ethoxycarbonyl)ethoxy]-4-methyl-2H-1,2,4-benzothiadiazine-(4H)-one 1,1-dioxide mp: 108°–110° C.

IR (Nujol): 1720, 1685, 1600, 1190, 1135 cm$^{-1}$.

NMR (CDCl$_3$, δ): 1.30 (3H, t J=8 Hz), 1.69 (3H, d, J=7 Hz), 3.53 (3H, s), 4.29 (2H, q, J=8 Hz), 4.87 (1H, q, J=7 Hz), 6.74 (1H, dd, J=2 Hz and 9 Hz), 6.83 (1H, d, J=2 Hz), 7.28 (1H, dd, J=2 Hz and 9 Hz), 7.53 (1H, d, J=2 Hz), 7.55 (1H, d, J=9 Hz), 7.83 (1H, d, J=9 Hz).

(78) (1R)-(+)-2-(3-Chlorophenyl)-6-[1-(ethoxycarbonyl)ethoxy]-4-methyl-2H-1,2,4-benzothiadiazine-3(4H)-one 1,1-dioxide mp: 135°–137° C.

IR (Nujol): 1740, 1700, 1600, 1580, 1340, 1210 cm$^{-1}$.

NMR (CDCl$_3$, δ): 1.30 (3H, t, J=7 Hz), 1.70 (3H, d, J=7 Hz), 3.46 (3H, s), 4.27 (2H, q, J=7 Hz), 4.86 (1H, q, J=7 Hz), 6.81–7.37 (6H, m), 7.85 (1H, d, J=9 Hz).

(79) (1R)-(+)-2-(2-Chlorophenyl)-6-[1-(ethoxycarbonyl)ethoxy]-4-methyl-2H-1,2,4-benzothiadiazine-3(4H)-one 1,1-dioxide IR (CHCl3) 1745, 1700, 1605, 1580, 1350, 1320, 1140 cm$^{-1}$.

NMR (CDCl3,δ): 1.30 (3H, t, J=7 Hz), 1.69 (3H, d, J=7 Hz), 3.54 (3H, s), 4.27 (2H, q, J=7 Hz), 4.88 (1H, q, J=7 Hz), 6.70–7.72 (6H, m), 7.82 (1H, d, J=9 Hz).

(80) (1R)-(+)-6-[1-(Ethoxycarbonyl)ethoxy]-2-(4-fluorophenyl)-4-methyl-2H-1,2,4-benzothiadiazine-3(4H)-one 1,1-dioxide mp: 100°–102° C.

IR (Nujol): 1740, 1680, 1605, 1370, 1340 cm$^{-1}$. NMR (CDCl$_3$, δ): 1.30 (3H, t, J=7 Hz), 1.69 (3H, d, J=7 Hz), 3.52 (3H, s), 4.26 (2H, q, J=7 Hz), 4.88 (1H, q, J=7 Hz), 6.71–7.43 (6H, m), 7.83 (1H, d, J=9 Hz).

(81) (1R)-(+)-6-[1-(Ethoxycarbonyl)ethoxy]-4-methyl-2-(4-methylthiophenyl)-2H-1,2,4-benzothiadiazine-3(4H)-one 1,1-dioxide mp: 156°–157° C.

IR (Nujol): 1720, 1605, 1600, 1580, 1205, 1180, 1130 cm$^{-1}$.

NMR (CDCl$_3$, δ): 1.29 (3H, t, J=7 Hz), 1.69 (3H, d, J=7 Hz), 2.50 (3H, s), 3.52 (3H, s), 4.25 (2H, q, J=7 Hz), 4.87 (1H, q, J=7 Hz), 6.72 (1H, dd, J=2 Hz and 9 Hz), 6.82 (1H, d, J=2 Hz), 7.32 (4H, s), 7.83 (1H, d, J=9 Hz).

(82) (1R)-(+)-2-(4-Dimethylaminophenyl)-6-[1-(ethoxycarbonyl)ethoxy]-4-methyl-2H-1,2,4-benzothiadiazine-3(4H)-one 1,1-dioxide mp: 190°–192° C.

IR (Nujol): 1715, 1680, 1600, 1195, 1130 cm$^{-1}$.

NMR (CDCl$_3$, δ): 1.29 (3H, t, J=7 Hz), 1.67 (3H, d, J=7 Hz), 3.00 (6H, s), 3.51 (3H, s), 4.25 (2H, q, J=7 Hz), 4.87 (1H, q, J=7 Hz), 6.69–6.81 (4H, m), 7.24 (2H, d, J=8 Hz), 7.84 (1H, d, J=8 Hz).

(83) (1R)-(+)-6-(1-Carboxyethoxy)-4-methyl-2-phenyl-2H-1,2,4-benzothiadiazine-3(4H)-one 1,1-dioxide mp: 184°–185.5° C.

IR (Nujol): 3200, 1750, 1660, 1610, 1320, 1180 cm$^{-1}$.

NMR (CDCl$_3$, δ): 1.74 (3H, d, J=7 Hz), 3.53 (3H, s), 3.55–4.1 (1H, br), 4.95 (1H, q, J=7 Hz), 6.76 (1H, dd, J=2 Hz and 9 Hz), 6.85 (1H, d, J=2 Hz), 7.35–7.55 (5H, m), 7.86 (1H, d, J=9 Hz).

(84) (1R)-(+)-6-(1-Carboxyethoxy)-4-methyl-2-(4-phenoxyphenyl)-2H-1,2,4-benzothiadiazine-3(4H)-one 1,1-oxide mp: 106° C. (dec.).

IR (Nujol): 3600–2400, 1740, 1695, 1665, 1600, 1585, 1345, 1215 cm$^{-1}$.

NMR (CDCl$_3$, δ): 1.74 (3H, d, J=7 Hz), 3.53 (3H, s), 3.63 (1H, br), 4.95 (1H, q, J=7 Hz), 6.76 (1H, dd, J=2 Hz and 9 Hz), 6.85 (1H, d, J=2 Hz), 7.0–7.45 (9H, m), 7.86 (1H, d, J=9 Hz).

(85) (1R)-(+)-6-(1-Carboxyethoxy)-2-(4-isopropylphenyl)-4-methyl-2H-1,2,4-benzothiadiazine-3(4H)-one 1,1-dioxide mp: 74° C. (dec.).

IR (Nujol): 3600–2400, 1730, 1695, 1600, 1340, 1315 cm$^{-1}$.

NMR (CDCl$_3$, δ): 1.27 (6H, d, J=7 Hz), 1.74 (3H, d, J=7 Hz), 2.76 (1H, m), 3.43 (1H, br), 3.52 (3H, s), 4.95 (1H, q, J=7 Hz), 6.76 (1H, dd, J=2 Hz and 9 Hz), 6.85 (1H, d, J=2 Hz), 7.32 (4H, s), 7.85 (1H, d, J=9 Hz).

(86) (1R)-(+)-6-(1-Carboxyethoxy)-2-[(3-chloro-4-methyl)phenyl]-4-methyl-2H-1,2,4-benzothiadiazine-3(4H)-one 1,1-dioxide mp: 184°–186° C.

IR (Nujol): 3600–2500, 1720, 1700, 1595, 1330 cm$^{-1}$.

NMR (CDCl$_3$, δ): 1.75 (3H, d, J=7 Hz), 2.42 (3H, s), 3 25 (1H, br), 3.53 (3H, s), 4.94 (1H, q, J=7 Hz), 6.77 (1H, dd, J=2 Hz and 9 Hz), 6.85 (1H, d, J=2 Hz), 7.23 (1H, dd, J=2 Hz and 8 Hz), 7.34 (1H, d, J=8 Hz), 7.41 (1H, d, J=2 Hz), 7.85 (1H, d, J=9 Hz).

(87) (1R)-(+)-6-(1-Carboxyethoxy)-4-methyl-2-(4-trifluoromethylphenyl)-2H-1,2,4-benzothiadiazine-(3(4H)-one 1,1-dioxide mp: 162°–163° C.

IR (CHCl$_3$) 3600–3300, 1720, 1690, 1600, 1340, 1320, 1130 cm$^{-1}$.

NMR (CDCl$_3$, δ): 1.75 (3H, d, J=6 Hz), 3.54 (3H, s), 4.90–5.01 (1H, q, J=6 Hz), 6.77 (1H, dd, J=2 Hz and 8 Hz), 6.87 (1H, d, J=2 Hz), 7.54 (2H, d, J=8 Hz), 7.74 (2H, d, J=8 Hz), 7.86 (1H, d, J=8 Hz).

(88) (1R)-(+)-6-(1-Carboxyethoxy)-2-cyclohexyl-4-methyl-2H-1,2,4-benzothiadiazine-3(4H)-one 1,1dioxide mp: 76°–77° C.

IR (CHCl$_3$) 3600–2400, 1720, 1680, 1600, 1330, 1310, 1170 cm$^{-1}$.

NMR (CDCl₃, δ): 120–1.45 (3H, m), 1.70 (3H, d, J=6 Hz), 1 82–1.88 (5H, m), 2.20–2.38 (2H, m), 3.44 (3H, s), 4.35–4.47 (1H, m), 4.76 (1H, s), 4.89 (1H, q, J=6 Hz), 6.67–6.74 (2H, m), 7.75 (1H, d, J=8 Hz).

(89) (1R)-(+)-6-(1-Carboxyethoxy)-4-methyl-2-(4-(4methylphenyl)-2H-1,2,4-benzothiadiazine-3(4H)-one 1,1-dioxide mp: 182°–183° C.

IR (CHCl₃): 1700, 1600, 1320, 1130 cm⁻¹.

NMR (CDCl₃, δ): 1.74 (3H, d, J=6 Hz), 2.40 (3H, s), 3.17 (1H, br s), 3.52 (3H, s), 4.89–5.00 (1H, q, J=6 Hz), 6.75 (1H, dd, J=2 Hz and 8 Hz), 6.84 (1H, d, J=2 Hz), 7.29 (4H, s), 7.85 (1H, d, J=8 Hz).

(90) (1R)-(+)-6-(1-Carboxyethoxy)-4-methyl-2-(2-pyridyl)-2H-1,2,4-benzothiadiazine-3(4H)-one 1,1-dioxide mp: 142°–143° C.

IR (Nujol): 3700–2300, 1700, 1600, 1350, 1320, 1275, 1210, 1190 cm⁻¹.

NMR (CDCl₃, δ): 1.56 (3H, d, J=7 Hz), 3.47 (3H, s), 5.17 (1H, q, J=7 Hz), 6.92 (1H, dd, J=2 Hz and 9 Hz), 7.08 (1H, d, J=2 Hz), 7.45–7.60 (2H, m), 7.84 (1H, d, J=9 Hz), 8.00 (1H, m), 8.56–8.59 (1H, m).

(91) (1R)-(+)-6-(1-Carboxyethoxy)-2-(3,4-dichlorophenyl)-4-methyl-2H-1,2,4-benzothiadiazine-3(4H)-one 1,1dioxide mp: 105°–106° C.

IR (Nujol): 3250–2400, 1735, 1690, 1600, 1585, 1300, 1290, 1175 cm⁻¹.

NMR (DMSO-d₆, δ): 1.57 (3H, d, J=7 Hz), 3.48 (3H, s), 5.20 (1H, q, J=7 Hz), 6.93 (1H, dd, J=2 Hz and 9 Hz), 7.08 (1H, d, J=2 Hz), 7.46 (1H, dd, J=2 Hz and 9 Hz), 7.76–7.93 (3H, m).

(92) (1R)-(+)-6-(1-Carboxyethoxy)-2-(3-chlorophenyl)-4-methyl-2H-1,2,4-benzothiadiazine-3(4H)-one 1,1dioxide mp: 174°–176° C.

IR (Nujol): 1725, 1700, 1610, 1580, 1330, 1310, 1180 cm⁻¹.

NMR (CDCl₃, δ): 1.74 (3H, d, J=7 Hz), 2.72 (1H, br s), 3.53 (3H, s), 4.95 (1H, q, J=7 Hz), 6.74–7.51 (6H, m), 7.86 (1H, d, J=9 Hz).

(93) (1R)-(+)-6-(1-Carboxyethoxy)-2-(2-chlorophenyl)-4 -methyl-2H-1,2,4-benzothiadiazine-3(4H)-one 1,1dioxide mp: 110°–112° C.

IR (Nujol): 1740, 1700, 1600, 1580, 1375, 1190 cm⁻¹.

NMR (CDCl₃, δ): 1.75 (3H, d, J=7 Hz), 3.55 (3H, s), 4.95 (1H, q, J=7 Hz), 6.74–7.67 (6H, m), 7.85 (1H, d, J=9 Hz).

(94) (1R)-(+)-6-(1-Carboxyethoxy)-2-(4-fluorophenyl)-4-methyl-2H-1,2,4-benzothiadiazine-3(4H)-one 1,1dioxide mp: 130°–132° C.

IR (Nujol): 1740, 1700, 1600, 1500, 1380, 1210 cm⁻¹.

NMR (CDCl₃, δ): 1.74 (3H, d, J=7 Hz), 3.52 (3H, s), 4.94 (1H, q, J=7 Hz), 5.80 (1H, br s), 6.74–7.43 (6H, m), 7.85 (1H, d, J=9 Hz).

(95) (1R)-(+)-6-(1-Carboxyethoxy)-4-methyl-2-(4-methylthiophenyl)-2H-1,2,4-benzothiadiazine-3(4H)-one 1,1-dioxide mp: 143°–144° C.

IR (Nujol): 3350–2300, 1730, 1660, 1600, 1580, 1190, 1090 cm⁻¹.

NMR (CDCl₃, δ): 1.74 (3H, d, J=7 Hz), 2.50 (3H, s), 3.53 (3H, s), 4.95 (1H, q, J=7 Hz), 6.76 (1H, dd, J=2 Hz and 9 Hz), 6.85 (1H, d, J=2 Hz), 7.32 (4H, s), 7.85 (1H, d, J=9 Hz).

(96) (1R)-(+)-6-(1-Carboxyethoxy)-2-(4-dimethylamino-phenyl)-4-methyl-2H-1,2,4-benzothiadiazine-3(4H)-one 1,1-dioxide mp: 190° C. (dec.).

IR (KBr): 3400, 2750–2200, 1690, 1590, 1450, 1320, 1180, 1125 cm⁻¹.

NMR (DMSO-d₆, δ) 1.57 (3H, d, J=7 Hz), 2.97 (6H, s), 3.47 (3H, s), 5.22 (1H, q, J=7 Hz), 6.85 (2H, d, J=9 Hz), 7.15 (2H, d, J=9 Hz), 6.92 (1H, dd, J=2 Hz and 9 Hz), 7.05 (1H, d, J=2 Hz), 7.85 (1H, d, J=9 Hz).

(97) 6-[1-(Carboxy)cyclohexylmethoxy]-2-(4-chlorophenyl)-4-methyl-2H-1,2,4-benzothiadiazine-3(4H)-one 1,1dioxide mp: 145–150° C.

IR (Nujol): 3300, 1700, 1600, 1580, 1370, 1310, 1190, 1130 cm⁻¹.

NMR (CDCl₃, δ): 1.10–2.10 (11H, m), 3.40 (3H, s), 4.40 (1H, br s), 6.60 (1H, d, J=9 Hz), 6.85 (1H, s), 7.25 (2H, d, J=9 Hz), 7.42 (2H, d, J=9 Hz), 7.70 (1H, d, J=9 Hz).

(98) (1R)-(+)-6-[1-(Ethoxycarbonyl)ethoxy]-4-methyl-2-(4-trifluoromethylphenyl)-2H-1,2,4-benzothiadiazine-3(4H)-one 1,1-dioxide mp: 124°–125° C.

IR (Nujol): 1720, 1685, 1595, 1330, 1130, 1060 cm⁻¹.

NMR (CDCl₃, δ): 1.30 (3H, t, J=6 Hz), 1.70 (3H, d, J=6 Hz), 3.54 (3H, s), 4.26 (2H, q, J=6 Hz), 4.88 (1H, q, J=6 Hz), 6.75 (1H, dd, J=2 Hz and 8 Hz), 6.85 (1H, d, J=2 Hz), 7.55 (2H, d, J=8 Hz), 7.75 (2H, d, J=8 Hz), 7.84 (1H, d, J=8 Hz)

(99) 6-Cyclohexylmethoxy-2-(4-cyclohexylmethoxycarbonylphenyl)-4-methyl-2H-1,2,4-benzothiadiazine-3(4H)-one 1,1-dioxide mp: 119°–121° C.

IR (Nujol): 1720, 1690, 1600, 1320 cm⁻¹.

NMR (DMSO-d₆, δ): 0.95–140 (10H, m), 1.55–1.95 (12H, m), 3.52 (3H, s), 4.00 (2H, d, J=5.8 Hz), 4.15 (2H, d, J=5.8 Hz), 6.97–7.10 (2H, m), 7.55 and 8.10 (4H, ABq, J=8.3 Hz), 7.87 (1H, d, J=8.7 Hz).

(100) 2-(4-Chlorophenyl)-4-methyl-6-(2-phthalimidoethoxy)-2H-1,2,4-benzothiadiazine-3(4H)-one 1,1-dioxide mp: 175°–180° C.

IR (Nujol): 1770, 1710, 1605, 1585 cm⁻¹.

NMR (DMSO-d₆, δ): 3.50 (3H, s), 4.0–4.1 (2H, m), 4.4–4.5 (2H, m), 6.95–7.05 (2H, m), 7.35–7.45 (2H, m), 7.55–7.56 (3H, m), 7.8–8.0 (4H, m).

(101) 6-[trans-4-(tert-Butoxccarbonylaminomethyl)-cyclohexylmethoxy]-2-(4-chlorophenyl)-4-methyl-2H-1,2,4-benzothiadiazine-3(4H)-one 1,1-dioxide mp: 133°–136° C.

IR (Nujol): 3400, 1690, 1600, 1590, 1520, 1450, 1360, 1340, 1180 cm⁻¹.

NMR (DMSO-d₆, δ): 0.75–1.20 (4H, m), 1.40 (9H, s), 1.40–2.00 (6H, m), 2.73 (2H, t, J=6 Hz), 3.50 (3H, s), 3.98 (2H, d, J=7 Hz), 7.00 (1H, d, J=9 Hz), 7.08 (1H s), 7.40 (2H, d, J=9 Hz), 7.60 (2H, d, J=9 Hz), 7.88 (1H, d, J=9 Hz).

(102) 2-(4-Chlorophenyl)-6-[1-(ethoxycarbonyl)cyclohexylmethoxy]-4-methyl-2H-1,2,4-benzothiadiazine-3(4H)-one 1,1-dioxide mp: 128°–131° C.

IR (Nujol): 1730, 1690, 1600, 1590, 1380, 1180 cm⁻¹.

NMR (CDCl₃, δ): 1.30 (3H, t, J=8 Hz), 1.10–2.10 (11H, m), 3.52 (3H, s), 4.25 (2H, q, J=8 Hz), 4.50 (1H, d, J=5 Hz), 6.75 (1H, dd, J=2 Hz and 9 Hz), 6.82 (1H, d, J=2 Hz), 7.35 (2H, d, J=9 Hz), 7.45 (2H, d, J=9 Hz), 7.85 (1H, d, J=9 Hz).

(103) 2-(4-Chlorophenyl)-4-methyl-6-[2-(tetrahydro-2Hpyranyl)methoxy]-2H-1,2,4-benzothiadiazine-3(4H)-one 1,1-dioxide mp: >250° C.

IR (Nujol): 1700, 1600, 1580, 1490, 1340, 1320, 1190 cm$^{-1}$.

NMR (DMSO-d$_6$, δ): 1.20–1.90 (6H, m), 3.40–3.90 (3H, m), 3.50 (3H, s), 4.10 (2H, d, J=6 Hz), 7.00 (1H, dd, J=2 Hz and 9 Hz), 7.10 (1H, d, J=2 Hz), 7.40 (2H, d, J=9 Hz), 7.60 (2H, d, J=9 Hz), 7.86 (1H, d, J=9 Hz).

(104) 2-(4-Carboxymethylphenyl)-6-isopropoxy-4-methyl-2H-1,2,4-benzothiadiazine-3(4H)-one 1,1-dioxide mp: 232°–233° C.

IR (Nujol): 3600–2500, 1700, 1685, 1600 cm$^{-1}$.

NMR (DMSO-d$_6$, δ): 1.34 (6H, d, J=6.0 Hz), 3.49 (3H, s), 3.66 (2H, s), 4.8–5.0 (1H, m), 6.95–7.01 (2H, m), 7.30 and 7.40 (4H, ABq, J=8.0 Hz), 7.84 (1H, d, J=9.0 Hz)

(105) 2-(4-Carboxyphenyl)-6-isopropoxy-4-methyl-2H-1,2,4-benzothiadiazine-3(4H)-one 1,1-dioxide mp: 247.5°–248.5° C.

IR (Nujol): 3200–2400, 1690, 1605 cm$^{-1}$.

NMR (DMSO-d$_6$, δ): 1.34 (6H, d, J=6.0 Hz), 3.50 (3H, s), 4.80–5.0 (1H, m), 6.95–7.07 (2H, m), 7.51 and 8.09 (4H, ABq, J=8.3 Hz), 7.86 (1H, d, J=8.4 Hz), 13.3 (1H, br s).

(106) 2-(3-Carboxypropyl)-6-isopropoxy-4-methyl-2H-1,2,4-benzothiadiazine-3(4H)-one 1,1-dioxide mp: 150°–152° C.

IR (Nujol): 1710, 1690, 1600, 1580, 1470, 1380, 1100 cm$^{-1}$.

NMR (CDCl$_3$, δ): 1.38 (6H, d, J=6 Hz), 2.05 (2H, m), 2.43 (2H, t, J=7 Hz), 3.46 (3H, s), 3.98 (2H, t, J=7 Hz), 4.67 (1H, m), 6.67 (1H, d, J=2 Hz), 6.76 (1H, dd, J=2 Hz and 9 Hz), 7.76 (1H, d, J=9 Hz).

(107) 2-(4-Carboxyphenyl)-6-cyclohexylmethoxy-4-methyl-2H-1,2,4-benzothiadiazine-3(4H)-one 1,1-dioxide mp: 240.5°–241° C.

IR (Nujol): 3300–2400, 1690, 1600, 1330 cm$^{-1}$.

NMR (DMSO-d$_6$, δ): 1.40–1.95 (5H, m), 1.55–1.95 (6H, m), 3.52 (3H, s), 4.00 (1H, d, J=5.8 Hz), 6.95–7.10 (2H, m), 7.50 and 8.05 (4H, ABq, J=8.3 Hz), 7.86 (1H, d, J=8.7 Hz), 13.3 (1H, br s).

(108) Hydrochloride salt of 6-[trans-4-(Aminomethyl)cyclohexylmethoxy]-2-(4-chlorophenyl)-4-methyl-2H-1,2,4-benzothiadiazine-3(4H)-one 1,1-dioxide mp: >250° C.

IR (Nujol): 3400, 1700, 1610, 1600, 1380, 1330, 1310, 1280, 1130 cm$^{-1}$.

NMR (DMSO-d6 0 (4H, m), 1.40–2.10 (6H, m), 2.70 (2H, m), 3.50 (3H, s), 4.02 (2H, d, J=7 Hz), 7.03 (1H, dd, J=2 Hz and 9 Hz), 7.10 (1H, d, J=2 Hz), 7.40 (2H, d, J=9 Hz), 7.60 (2H, d, J=9 Hz), 7.90 (1H, d, J=9 Hz), 8.00 (1H, br s).

(109) 7Chloro-6-isopropoxy-4-methyl-2-(2-pyridyl)-2H-(1,2,4-benzothiadiazine-3(4H)-one 1,1-dioxide mp: 193°–194° C.

IR (Nujol): 1685, 1590, 1345 cm$^{-1}$.

NMR (CDCl$_3$, δ): 1.46 (6H, d, J=6 Hz), 3.55 (3H, s), 4.6–4.85 (1H, m), 6.75 (1H, s), 7.35–7.55 (2H, m), 7.90 (1H, s), 7.85–7.95 (1H, m), 8.6–8.7 (1H, m).

(110) 7-Bromo-6-isopropoxy-4-methyl-2-(2-pyridyl)-2H-1,2,4-benzothiadiazine-3(4H)-one 1,1-dioxide mp: 194.5°–195.5° C.

IR (Nujol): 1690, 1590, 1345 cm$^{-1}$.

NMR (CDCl$_3$, δ): 1.47 (6H, d, J=6 Hz), 3.55 (3H, s), 4.6–4.85 (1H, m), 6.71 (1H, s), 7.35–7.55 (2H, m), 7.85–7.95 (1H, m), 8.04 (1H, s), 8.60–8.70 (1H, m).

(111) 2-(4-Chlorophenyl)-5,7-dichloro-6-hydroxy-4-methyl-2H-1,2,4-benzothiadiazine-3(4H)-one 1,1dioxide mp: 197°–198° C.

IR (Nujol): 1720, 1700, 1500, 1360, 1180 cm$^{-1}$.

NMR (DMSO-d$_6$, δ): 3.55 (3H, s), 7.4 (2H, d, J=9 Hz), 7.60 (2H, d, J=9 Hz), 8.00 (1H, s).

EXAMPLE 7

In a similar manner to that of Example 3, there were obtained the following compounds.

(1) 6-Hydroxy-4-methyl-2-(P-tolyl)-2H-1,2,4-benzothiadiazine-3 (4H)-one 1,1-dioxide mp: 163°–165° C.

IR (Nujol): 3400, 1670, 1610, 1590, 1480, 1340, 1320, 1220, 1190 cm$^{-1}$.

NMR (DMSO-d$_6$, δ): 2.35 (3H, s), 3.40 (3H, s), 6.80 (1H, d, J=9 Hz), 6.90 (1H, s), 7.10–7.40 (4H, m), 7.75 (1H, d, J=9 Hz).

(2) 6-Hydroxy-4-methyl-2-phenyl-2H-1,2,4-benzothiadiazine-3 (4H)-one 1,1-dioxide mp: 235°–237° C.

IR (Nujol): 1680, 1610, 1590, 1470, 1330, 1210, 1190 cm$^{-1}$.

NMR (DMSO-d$_6$, δ): 3.45 (3H, s), 6.80 (1H, d, J=9 Hz), 6.90 (1H, s), 7.30–7.60 (5H, m), 7.78 (1H, d, J-9 Hz).

(3) 6-Hydroxy-4-methyl-2-(4-trifluoromethylphenyl)-2H-1,2,4-benzothiadiazine-3(4H)-one 1,1-dioxide mp: 230°–233° C.

IR (Nujol): 3300, 1660, 1610, 1590, 1460, 1350, 1320, 1190, 1110 cm$^{-1}$.

NMR (DMSO-d$_6$, δ): 3.42 (3H, s), 6.80 (2H, d, J=9 Hz), 6.90 (1H, s), 7 60 (2H, d, J=7 Hz), 7.77 (1H, d, J=9 Hz), 7.92 (2H, d, J=7 Hz).

(4) 2-(3,4-Dichlorophenyl)-6-hydroxy-4-methyl-2H-1,2,4-benzothiadiazine-3(4H)-one 1,1-dioxide mp: >250° C.

IR (Nujol): 3350, 1660, 1610, 1590, 1460, 1350, 1340 cm$^{-1}$.

NMR (DMSO-d$_6$, δ): 3.45 (3H, s), 6.82 (1H, d, J=8 Hz), 6.86 (1H, s), 7.45 (1H, dd, J=2 Hz and 9 Hz), 7.65–7.90 (3H, m), 11.0 (1H, s).

(5) 2-(4-Fluorophenyl)-6-hydroxy-4-methyl-2H-1,2,4-benzothiadiazine-3(4H)-one 1,1-dioxide mp: 228°–230° C.

IR (Nujol): 3400, 1650, 1610, 1580, 1460, 1350, 1210 cm$^{-1}$.

NMR (DMSO-d$_6$, δ): 3.40 (3H, s), 6.80 (1H, d, J=9 Hz), 6.85 (1H, s), 7.30–7.60 (4H, m), 7.75 (1H, d, J=9 Hz), 11.0 (1H, br s).

(6) 2-(2-Chlorophenyl)-6-hydroxy-4-methyl-2H-1,2,4 benzothiadiazine-3(4H)-one 1,1-dioxide mp: 195°–196° C.

IR (Nujol): 3400, 1670, 1620, 1590, 1470, 1460, 1330 cm$^{-1}$.

NMR (DMSO-d$_6$, δ): 3.48 (3H, s), 6.83 (1H, d, J=9 Hz), 6.93 (1H, s), 7.40–7.75 (4H, m), 7.77 (1H, d, J=9 Hz), 1.0 (1H, br s).

(7) 2-(3-Chlorophenyl)-6-hydroxy-4-methyl-2H-1,2,4-benzothiadiazine-3(4H)-one 1,1-dioxide mp: 242°–243° C.

IR (Nujol): 3500, 1680, 1660, 1610, 1590, 1460, 1370, 1320 cm$^{-1}$.

NMR (DMSO-d$_6$, δ): 3.45 (3H, s), 6.83 (1H, dd, J=2 Hz and 9 Hz), 6.89 (1H, d, J=2 Hz), 7.30–7.65 (4H, m), 7.77 (1H, d, J=9 Hz).

(8) 2-(4-Chlorophenyl)-6-hydroxy-4-isopropyl-2H-1,2,4-benzothiadiazine-3(4H)-one 1,1-dioxide
mp: 212°–213° C.
IR (Nujol): 3350, 1660, 1610, 1460, 1350, 1320 cm$^{-1}$.
NMR (DMSO-d$_6$, δ): 1.52 (6H, d, J=6 Hz), 4 52 (1H, m), 6.81 (1H, d, J=9 Hz), 6.96 (1H, s), 7.25–7.70 (4H, m), 7.72 (1H, d, J=9 Hz).

(9) 2-(4-Chlorophenyl)-4-ethyl-6-hydroxy-2H-1,2,4-benzothiadiazine-3(4H)-one 1,1-dioxide
mp: 253°–255° C.
IR (Nujol): 3300, 1640, 1610, 1580, 1460, 1350, 1330 cm$^{-1}$.
NMR (DMSO-d$_6$, δ): 1.28 (3H, t, J=7 Hz), 4.05 (2H, q, J=7 Hz), 6.82 (1H, dd, J=2 Hz and 9 Hz), 6.90 (1H, d, J=2 Hz), 7.42 (2H, d, J=9 Hz), 7.60 (2H, d, J=9 Hz), 7.78 (1H, d, J=9 Hz).

(10) 2-(4-Chlorobenzyl)-6-hydroxy-4-methyl-2H-1,2,4-benzothiadiazine-3(4H)-one 1,1-dioxide
mp: 130°–132° C.
IR (Nujol): 3250, 1645, 1610, 1580, 1335, 1180 cm$^{-1}$.
NMR (DMSO-d$_6$, δ): 3.41 (3H, s), 4.94 (2H, s), 6.80 (1H, d, J=9.0 Hz), 6.82 (1H, s), 7.35 and 7.39 (4H, ABq, J=8.6 Hz), 7.75 (1H, d, J=9.0 Hz), 10.93 (1H, br s).

(11) 2-Cyclohexyl-6-hydroxy-4-methyl-2H-1,2,4- benzothiadiazine-3(4H)-one 1,1-dioxide
mp: 189°–190° C.
IR (Nujol): 3300, 1665, 1610, 1585, 1320, 1200, 1180 cm$^{-1}$.
NMR (DMSO-d$_6$, δ): 1.0–1.5 (3H, m), 1.5–1.9 (5H, m), 2.05–2.35 (2H, m), 3.38 (3H, s), 4.2–4.4 (1H, m), 6.76 (1H, d, J=8.2 Hz), 6.78 (1H, s), 7.66 (1H, d, J=8.2 Hz), 10.84 (1H, br s).

(12) 6-Hydroxy-4-methyl-2-pentyl-2H-1,2,4-benzothiadiazine-3(4H)-one 1,1-dioxide
mp 108°–110° C.
IR (Nujol): 3300, 1640, 1600, 1580, 1460, 1340, 1180 cm$^{-1}$.
NMR (DMSO-d$_6$, δ): 0.84 (3H, t, J=6 Hz), 1.10–1.40 (4H, m), 1.50–1.70 (2H, m), 3.40 (3H, s), 3.74 (2H, t, J=7 Hz), 6.70–6.90 (2H, m), 7.70 (1H, d, J=9 Hz), 10. (1H, br s).

(13) 2-(4-Carboxyphenyl)-6-hydroxy-4-methyl-2H-1,2,4- benzothiadiazine-3(4H)-one 1,1-dioxide
mp: >250° C.
IR (Nujol): 3600–2500, 3350, 1705, 1610 cm$^{-1}$.
NMR (DMSO-d$_6$, δ): 3.46 (3H, s), 6.80–6.95 (2H, m), 7.50 and 8.05 (4H, ABq, J=8.4 Hz), 7.80 (1H, d, J=8.7 Hz), 10.99 (1H, s).

(14) 2-(4-Carboxymethylphenyl)-6-hydroxy-4-methyl-2H-1,2,4-benzothiadiazine-3(4H)-one 1,1-dioxide
mp: >250° C.
IR (Nujol): 3210, 1715, 1665, 1620, 1585, 1340 cm$^{-1}$.
NMR (DMSO-d$_6$, δ): 3.45 (3H, s), 3.66 (2H, s), 6.75–6.90 (2H, m), 7.30 and 7.40 (4H, ABq, J=8.3 Hz), 7.75 (1H, d, J=8.6 Hz), 10.96 (1H, s).

(15) 2-(3-Carboxypropyl)-6-hydroxy-4-methyl-2H-1,2,4- benzothiadiazine-3(4H)-one 1,1-dioxide
mp: 145°–148° C.
IR (Nujol): 3300, 1690, 1600, 1590, 1470, 1380, 1340, 1120 cm$^{-1}$.
NMR (DMSO-d$_6$, δ): 1.80 (2H, m), 2.24 (2H, t, J=7 Hz), 3.40 (3H, s), 3.80 (2H, t, J=7 Hz), 6.78 (1H, d, J=9 Hz), 6.80 (1H, s), 7.71 (1H, d, J=9 Hz), 10.8 (1H, br s).

(16) 6-Hydroxy-4-methyl-2-(4-phenoxyphenyl)-2H-1,2,4-benzothiadiazine-3(4H)-one 1,1-dioxide.
mp: 239°–240° C.
IR (Nujol): 3260, 1645, 1610, 1585, 1345, 1210 cm$^{-1}$.
NMR (CDCl$_3$, δ): 3.51 (3H, s), 6.75–6.85 (2H, m), 7.0–7.45 (9H, m), 7.67–7.78 (1H, m).

(17) 6-Hydroxy-2-(4-isopropylphenyl)-4-methyl-2H-1,2,4-benzothiadiazine-3(4H)-one 1,1-dioxide
mp: >250° C.
IR (Nujol): 3410, 3370, 1670, 1610, 1585, 1325 cm$^{-1}$.
NMR (CDCl$_3$, δ): 1.23 (6H, d, J=7 Hz), 2.93 (1H, m), 3.31 (1H, br s), 3.47 (3H, s), 6.70 (1H, d, J=2 Hz), 6.72 (1H, dd, J=2 Hz and 9 Hz), 7.28 (4H, s), 7.70 (1H, d, J=9 Hz).

(18) 2-[(3-Chloro-4-methyl)phenyl]-6-hydroxy-4-methyl-2H-1,2,4-benzothiadiazine-3(4H)-one 1,1-dioxide
mp: >250° C.
IR (Nujol): 3400, 1670, 1610, 1590, 1325 cm$^{-1}$.
NMR (DMSO-d$_6$, δ): 2.39 (3H, s), 3.45 (3H, s), 6.82 (1H, dd, J=2 Hz and 9 Hz), 6.88 (1H, d, J=2 Hz), 7.28 (1H, dd, J=2 Hz and 8 Hz), 7.44 (1H, d, J=2 Hz), 7.51 (1H, d, J=8 Hz), 7.76 (1H, d, J=9 Hz).

(19) 6-Hydroxy-4-methyl-2-(4-methylthiophenyl)-2H-1,2,4-benzothiadiazine-3(4H)-one 1,1-dioxide
mp: 248°–249° C.
IR (Nujol): 3250, 1670, 1610, 1580, 1330, 1180 cm$^{-1}$.
NMR (DMSO-d$_6$, δ): 2.52 (3H, s), 3.45 (3H, s), 6.81 (1H, dd, J=2 Hz and 9 Hz), 6.87 (1H, d, J=2 Hz), 7.27 (2H, d, J=9 Hz), 7.37 (2H, d, J=9 Hz), 7.86 (1H, d, J=9 Hz).

(20) 2-(4-Dimethylaminophenyl)-6-hydroxy-4-methyl-2H-1,2,4-benzothiadiazine-3(4H)-one 1,1-dioxide
mp: 190°–191° C.
IR (Nujol): 3350, 1660, 1600, 1580, 1520, 1480, 1320, 1180, 1140 cm$^{-1}$.
NMR (DMSO-d$_6$, δ): 2.95 (6H, s), 3.44 (3H, s), 6.73–6.85 (4H, m), 7.10 (2H, d, J=9 Hz), 7.73 (1H, d, J=8 Hz), 10.90 (1H, s).

EXAMPLE 8

In a similar manner to that of Example 4, there were obtained the following compounds.

(1) 6-isopropoxy-4-methyl-2-(P-tolyl)-2H-1,2,4-benzothiadiazine-3(4H)-one 1,1-dioxide
mp: 163°–165° C.
IR (Nujol): 1690, 1600, 1580, 1340, 1320, 1130, 1110 cm$^{-1}$.
NMR (DMSO-d$_6$, δ): 1.33 (3H, s), 1.36 (3H, s), 2.38 (3H, s), 3.49 (3H, s), 4.90 (1H, m), 6.90–7.10 (2H, m), 7.20–7.34 (4H, m), 7.84 (1H, d, J=8 Hz).

(2) 6-Isopropoxy-4-methyl-2-phenyl-2H-1,2,4-benzothiadiazine-3(4H)-one 1,1-dioxide
mp: 134°–135° C.
IR (Nujol): 1690, 1600, 1580, 1450, 1340, 1190 cm$^{-1}$.
NMR (CDCl$_3$, δ): 1.42 (6H, d, J=6 Hz). 3.55 (3H, s), 4.70 (1H, m), 6.70–7.90 (2H, m), 7.35–7.60 (5H, m), 7.82 (1H, d, J=9 Hz).

(3) 2-(3,4-Dichlorophenyl)-6-isopropoxy-4-methyl-2H-1,2,4-benzothiadiazine-3(4H)-one 1,1-dioxide
mp: 109°–110° C.
IR (Nujol): 1710, 1570, 1460, 1350, 1320 cm$^{-1}$.
NMR (DMSO-d$_6$, δ): 1.34 (6H, d, J=5 Hz), 3.49 (3H, s), 4.90 (1H, m), 7.01 (1H, d, J=8 Hz), 7.03 (1H, s), 7.45 (1H, d, J=9 Hz), 7.74–7.89 (3H, m).

(4) 2-(4-Fluorophenyl)-6-isopropoxy-4-methyl-2H-1,2,4-benzothiadiazine-3(4H)-one 1,1-dioxide
mp: 139°–140° C.
IR (Nujol): 1700, 1600, 1570, 1460, 1380, 1330, 1210 cm$^{-1}$.

NMR (DMSO-d$_6$, δ): 1.33 (6H, d, J=6 Hz), 3.50 (3H, s), 4.90 (1H, m), 6.98–7.02 (2H, m), 7.30–7.48 (4H, m), 7.85 (1H, d, J=9 Hz)

(5) 2-(4-Chlorophenyl)-6-ethoxy-4-methyl-2H-1,2,4-benzothiadiazine-3(4H)-one 1,1-dioxide
mp: 150°–151° C.
IR (Nujol): 1680, 1600, 1580, 1460, 1350, 1320, 1220, 1190, 1130 cm$^{-1}$.
NMR (DMSO-d$_6$, δ): 1.39 (3H, t, J=7 Hz), 3.50 (3H, s), 4.23 (2H, q, J=7 Hz), 7.00 (1H, dd, J=2 Hz and 9 Hz), 7.05 (1H, d, J=2 Hz), 7.40–7.63 (4H, m), 7.87 (1H, d, J=9 Hz).

(6) 6-Benzyloxy-2-(4-chlorophenyl)-4-methyl-2H-1,2,4-benzothiadiazine-3(4H)-one 1,1-dioxide
mp: 174°–175° C.
IR (Nujol): 1690, 1600, 1590, 1460, 1320, 1180 cm$^{-1}$.
NMR (DSMO-d$_6$, δ): 3.34 (3H, s), 5.32 (2H, s), 7.07 (1H, dd, j=9 Hz and 2 Hz), 7.20 (1H, d, J=2 Hz), 7.30–7.63 (9H, m), 7.90 (1H, d, J=9 Hz).

(7) 2-(4-Chlorophenyl)-6-cyclopropylmethoxy-4-methyl-2H-1,2,4-benzothiadiazine-3(4H)-one 1,1-dioxide
mp: 145°–146° C.
IR (Nujol): 1690, 1600, 1580, 1540, 1330 cm$^{-1}$.
NMR (DMSO-d$_6$, δ): 0.30–0.45 (4H, m), 1.30 (1H, m), 3.45 (3H, s), 4.01 (2H, d, J=7 Hz), 6.90–7.10 (2H, m), 7.35–7.70 (4H, m), 7.85 (1H, d, J=9 Hz).

(8) 2-(2-Chlorophenyl)-6-isopropoxy-4-methyl-2H-1,2,4-benzothiadiazine-3(4H)-one 1,1-dioxide
mp: 150°–152° C.
IR (Nujol): 1700, 1600, 1580, 1450, 1360, 1320, 1200 cm$^{-1}$.
NMR (DMSO-d$_6$, δ): 1.34 (6H, d, J=6 Hz), 3 52 (3H, s), 4.90 (1H, m), 6.95–7.10 (2H, m), 7.50–7.70 (4H, m), 7.86 (1H, d, J=9 Hz).

(9) 2-(3-Chlorophenyl)-6-isopropoxy-4-methyl-2H-1,2,4-benzothiadiazine-3(4H)-one 1,1-dioxide
mp: 126°–127° C.
IR (Nujol): 1700, 1600, 1590, 1380, 1330, 1310, 1800 cm$^{-1}$.
NMR (DMSO-d$_6$, δ): 1.34 (6H, d, J=6 Hz), 3.49 (3H, s), 4.90 (1H, m), 6.98–7.03 (2H, m), 7.37–7.65 (4H, m), 7.86 (1H, d, J=9 Hz).

(10) 2-(4-Chlorophenyl)-4-methyl-6-propoxy-2H-1,2,4-benzothiadiazine-3(4H)-one 1,1-dioxide
mp: 142°–143° C.
IR (Nujol): 1700, 1690, 1610, 1580, 1340, 1320 cm$^{-1}$.
NMR (DMSO-d$_6$, δ): 1.02 (3H, t, J=7 Hz), 1.80 (2H, q, J=7 Hz), 3.50 (3H, s), 4.10 (2H, t, J=7 Hz), 6.95–7.10 (2H, m), 7.40–7.70 (4H, m), 7.90 H, d, J=9 Hz).

(11) 6-Butoxy-2-(4-chlorophenyl)-4-methyl-2H-1,2,4-benzothiadiazine-3(4H)-one 1,1-dioxide
mp: 102°–103° C.
IR (Nujol): 1700, 1600, 1340, 1320, 1180, 1130 cm$^{-1}$.
NMR (DMSO-d$_6$, δ): 0.96 (3H, t, J=7 Hz), 1.35–1.90 (4H, m), 3.50 (3H, s), 4.18 (2H, t, J=7 Hz), 6.95–7.10 (2H, m), 7.35–7.70 (4H, m), 8.90 (1H, d, J=9 Hz).

(12) 6-Methoxy-4-methyl-2-(P-tolyl)-2H-1,2,4-benzothiadiazine-3(4H0-one 1,1-dioxide
mp: 170°–173° C.
IR (Nujol): 1690, 1460, 1440, 1330, 1310, 1180, 1130 cm$^{-1}$.
NMR (DMSO-d$_6$, δ): 3.50 (3H, s), 3.95 (3H, s), 6.95–7.10 (2H, m), 7.20–7.40 (4H, m), 7.95 (1H, d, J=9 Hz).

(13) 6-Methoxy-4-methyl-2-phenyl-2H-1,2,4-benzothiadiazine-3(4H)-one 1,1-dioxide
mp: 203°–206° C.
IR (Nujol): 1710, 1700, 1600, 1450, 1330, 1300, 1220, 1180, cm$^{-1}$.
NMR (DMSO-d$_6$, δ): 3.50 (3H, s), 3.95 (3H, s), 7.00 (1H, d, J=9 Hz), 7.05 (1H, s), 7.25–7.65 (5H, m), 7.88 (1H, d, J=9 Hz).

(14) 6-Methoxy-4-methyl-2-(4-trifluoromethylphenyl)-2H-1,2,4-benzothiadiazine-3(4H)-one 1,1-dioxide
mp: 165°–168° C.
IR (Nujol): 1700, 1610, 1580, 1460, 1340, 1170, 1140 cm$^{-1}$.
NMR (DMSO-d$_6$, δ): 3.52 (3H, s), 3.95 (3H, s), 7.02 (1H, dd, J=2 Hz and 9 Hz), 7.10 (1H, d, J=2 Hz), 7 65 (2H, d, J=7 Hz), 7.92 (1H, d, J=9 Hz), 7.98 (2H, d, J=7 Hz).

(15) 2-(3,4-Dichlorophenyl)-6-methoxy-4-methyl-2H-1,2,4-benzothiadiazine-3(4H)-one 1,1-dioxide
mp: 150°–151° C.
IR (Nujol): 1710, 1600, 1470, 1340, 1320 cm$^{-1}$.
NMR (DMSOd-6, ? ): 3.50 (3H, s), 3.95 (3H, s), 7.02 (1H, d, J=9 Hz), 7.06 (1H, s), 7.45 (1H, d, J=8 Hz), 7.70–8.00 (3H, m).

(16) 2-(4-Fluorophenyl)-6-methoxy-4-methyl-2H-1,2,4-benzothiadiazine-3(4H)-one 1,1-dioxide
mp: 203°–204° C.
IR (Nujol): 1700, 1590, 1440 cm$^{-1}$.
NMR (DMSO-d$_6$, δ): 3.52 (3H, s), 3.95 (3H, s), 7.02 (1H, d, J=9 Hz), 7.10 (1H, s), 7.30–7.60 (4H, m), 7.90 (1H, d, J=9 Hz).

(17) 6-Isopropoxy-2-(4-methoxyphenyl)-4-methyl-2H-1,2,4-benzothiadiazine-3(4H)-one 1,1-dioxide
mp: 182°–183° C.
IR (Nujol): 1690, 1600, 1460, 1370, 1340 cm$^{-1}$.
NMR (DMSO-d$_6$, δ): 1.34 (6H, d, J=6 Hz), 3.50 (3H, s), 3.82 (3H, s), 4.89 (1H, m), 7.00–7.08 (4H, m), 7.25–7.32 (2H, m), 7.84 (1H, d, J=9 Hz).

(18) 2-(2-Chlorophenyl)-6-methoxy-4-methyl-2H-1,2,4-benzothiadiazine-3(4H)-on®1,1-dioxide
mp: 155°–156° C.
IR (Nujol): 1710, 1600, 1460, 1330, 1300, 1180, 1140 cm$^{-1}$.
NMR (DMSO-d$_6$, δ): 3.54 (3H, s), 3.95 (3H, s), 7.03 (1H, dd, J=2 Hz and 9 Hz), 7.11 (1H, d, J=2 Hz), 7.50–7.70 (4H, m), 7.90 (1H, d, J=9 Hz).

(19) 2-(3-Chlorophenyl)-6-methoxy-4-methyl-2H-1,2,4-benzothiadiazine-3(4H)-one 1,1-dioxide
mp: 153°–154° C.
IR (Nujol): 1710, 1600, 1590, 1460, 1340, 1320, 1180, 1130, 1060, 1030 cm$^{-1}$.
NMR (DMSO-d$_6$, δ): 3.51 (3H, s), 3.94 (3H, s), 7.02 (1H, dd, J=2 Hz and 9 Hz), 7 07 (1H, d, J=2 Hz), 7.34–7.65 (4H, m), 7.90 (1H, d, J=9 Hz).

(20) 2-(4-Choorophenyl)-6-methoxy-4-methyl-2H-1,2,4-benzothiadiazine-3(4H)-one 1,1-dioxide
mp: 167°–168° C.
IR (Nujol): 1710, 1600, 1330, 1180, 1130 cm$^{-1}$.
NMR (DMSO-d$_6$, δ): 3.42 (3H, s), 3.95 (3H, s), 6.95–7.10 (2H, m), 7.38–7.65 (2H, m), 8.90 (1H, d, J=9 Hz).

(21) 2-(4-Chlorophenyl)-6-isopropyoxy-4-methyl-2H-1,2,4-benzothiadiazine-3(4H)-one 1,1-dioxide
IR (Neat): 2980, 1680, 1600, 1580, 1330, 1180, 1110 cm$^{-1}$.
NMR (CDCl$_3$, δ): 1.38 (6H, d, J=6.0 Hz), 3.45 (3H, s), 4.55–4.75 (1H, m), 5.00 (2H, s), 6.65 (1H, d, J=1.9 Hz), 6.77 (1H, dd, J=1.9 and 8.8 Hz), 7.27 and 7.40 (4H, ABq, J=8.4 Hz), 7.80 (1H, d, J=8.8 Hz).

(22) 4-Isopropyl-2-(4-Chlorophenyl)-6-methoxy-2H-1,2,4-benzothiadiazine-3(4H)-one 1,1-dioxide
mp: 166°-168° C.
IR (Nujol): 1690, 1600, 1570, 1460, 1340, 1300 cm$^{-1}$
NMR (DMSO-d$_6$, δ): 1.54 (6H, d, J=6 Hz), 3.94 (3H, s), 4.61 (1H, m), 6.90-7.10 (2H, m), 7.30-7.70 (4H, m), 7.85 (1H, d, J=9 Hz).

(23) 2-(4-Chlorophenyl)-6-isopropoxy-4-isopropyl-2H-1,2,4-benzothiadiazine-3(4H)-one 1,1-dioxide
mp: 158°-160° C.
IR (Nujol): 1690, 1590, 1490, 1460, 1340, 1300 cm$^{-1}$
NMR (DMSO-d$_6$, δ): 1.34 (6H, d, J=6 Hz), 1.52 (6H, d, J=6 Hz), 4.58 (1H, m) 4.88 (1H, m), 6.90-7.05 (2H, m), 7.30-7.65 (4H, m), 7.82 (1H, d, J=9 Hz).

(24) 2-(4-Chlorophenyl)-4-ethyl-6-methoxy-2H-1,2,4-benzothiadiazine-3(4H)-one 1,1-dioxide.
mp: 106°-107° C.
IR (Nujol): 1690, 1600, 1570, 1490, 1460, 1350, 1310 cm$^{-1}$.
NMR (DMSO-D$_6$, δ): 1.28 (3H, t, J=7 Hz), 3.95 (3H, s), 4.14 (2H, q, J=7 Hz), 7.03 (1H, d, J=9 Hz), 7.09 (1H, s), 7.42 (2H, d, J=9 Hz), 7.60 (2H, d, J=9 Hz), 7.90 (1H, d, J=9 Hz).

(25) 2-(4-Chlorophenyl)-4-ethyl-6-isopropoxy-2H-1,2,4- benzothiadiazine-3(4H)-one 1,1-dioxide
mp: 167°-168° C.
IR (Nujol): 1700, 1600, 1580, 1460, 1340, 1310, cm$^{-1}$.
NMR (DMSO-d$_6$, δ): 1.26 (3H, t, J=7 Hz), 1.34 (6H, d, J=6 Hz), 4.13 (2H, q, J=7 Hz), 7.05-7.09 (2H, m), 7.42 (2H, d, J=9 Hz), 7.60 (2H, d, J=9 Hz), 7.87 (2H, d, J=9 Hz).

(26) 2-Cyclohexyl-6-isopropoxy-4-methyl-2H-1,2,4-benzothiadiazine-3(4H)-one 1,1-dioxide
mp: 111°-112° C.
IR (Nujol): 1685, 1605, 1330, 1180, 1110 cm$^{-1}$.
NMR (DMSO-d$_6$, δ): 1.0-1.45 (3H, m), 1.31 (6H, d, J=6.0 Hz), 1.5-1.9 (5H, m), 2.05-2.35 (2H, m), 3.43 (3H, s), 4.25-4.4 (1H, m), 4.84 (1H, m), 6.91 (1H, s), 6.78 (1H, d, J=9.0 Hz), 7.75 (1H, d, J=9.0 Hz).

(27) 6-Isopropoxy-4-methyl-2-pentyl-2H-1,2,4-benzothiadiazine-3(4H)-one 1,1-dioxide.
mp: 44°-46° C.
IR (Nujol): 1690, 1600, 1580, 1460, 1340, 1320, 1190 cm$^{-1}$.
NMR (DMSO-d$_6$, δ): 0.84 (3H, t, J=6 Hz), 1.05-1.40 (4H, m), 1.31 (6H, d, J=6 Hz), 1.50-1.75 (2H, m), 3.44 (3H, s), 3.74 (2H, t, J=7 Hz), 4.85 (1H, m), 6.90-7.05 (2H, m), 7.78 (1H, d, J=9 Hz).

(28) 6-Isopropoxy-2-(4-isopropoxycarbonylphenyl)-4-methyl-2H-1,2,4-benzothiadiazine-3(4H)-one 1,1-dioxide.
mp: 128-129° C.
IR (Nujol): 1720, 1710, 1610, 1340, 1280 cm$^{-1}$.
NMR (CDCl$_3$, δ): 1.38 (6H, d, J=6.8 Hz), 1.43 (6H, d, J=6.5 Hz), 3.54 (3H, s), 4.63-4.8 (1H, m), 5.2-5.35 (1H, m), 6.76 (1H, d, J=2 Hz), 6.82 (1H, dd, J=2 Hz and 8.7 Hz), 7.50 and 8.15 (4H, ABq, J=8.4 Hz), 7.83 (1H, d, J=8.7 Hz).

(29) 2-(4-Isopropoxycarbonylmethylphenyl)-6-isopropoxy-4-methyl-2H-1,2,4-benzothiadiazine-3(4H)-one 1,1-dioxide
mp: 117°-120° C.
IR (Nujol): 1730, 1690, 1595, 1335, 1325 cm$^{-1}$.
NMR (CDCl$_3$, δ): 1.24 (6H, d, J=6.0 Hz), 1.41 (6H, d, J=6.0 Hz), 3.52 (3H, s), 3.63 (2H, s), 4.6-4.8 (1H, m), 4.9-5.1 (1H, m), 6.7-6.85 (2H, m), 7.3-7.5 (4H, m), 7.75-7.80 (1H, m).

(30) 6-Isopropoxy-2-(3-isopropoxycarbonylpropyl)-4-methyl-2H-1,2,4-benzothiadiazine-3(4H)-one 1,1-dioxide
IR (CHCl$_3$): 1720, 1700, 1600, 1580, 1340, 1270, 1120 cm$^{-1}$.
NMR (CDCl$_3$, δ): 1.12 (6H, d, J=6 Hz), 1.30 (6H, d, J=6 Hz), 1.99 (2H, m), 2.28 (2H, t, J=7 Hz), 3.41 (3H, s), 3.90 (2H, t, J=7 Hz), 4.60 (1H, m), 4.92 (1H, m), 6.60 (1H, d, J=2 Hz), 6.70 (1H, dd, J=2 Hz and 9 Hz), 7.70 (1H, d, J=9 Hz).

(31) 2-(4-Chlorophenyl)-5,7-dichloro-6-isopropoxy-4-methyl-2H-1,2,4-benzothiadiazine-3(4H)-one 1,1-dioxide
mp: 185°-188° C.
IR (Nujol): 1710, 1470, 1380, 1360, 1190 cm$^{-1}$.
NMR (DMSO-d$_6$, δ): 1.38 (6H, d, J=6 Hz), 3.33 (3H, s), 4.75 (1H, m), 7.44 (2H, d, J=9 Hz), 7.61 (2H, d, J=9 Hz), 8.14 (1H, s).

(32) 2-(4-Chlorobenzyl)-6-methoxy-4-methyl-2H-1,2,4-benzothiadiazine-3(4H)-one 1,1-dioxide
mp: 132°-133° C.
IR (Nujol): 1675, 1600, 1350, 1330, 1195 cm$^{-1}$.
NMR (DMSO-d$_6$, δ): 3.47 (3H, s), 3.92 (3H, s), 4.96 (2H, s), 6.98 (1H, d, J=9.0 Hz), 7.00 (1H, s), 7.35 and 7.40 (4H, ABq, J=8.7 Hz), 7.87 (1H, d, J=9.0 Hz).

(33) 2-Cyclohexyl-6-methoxy-4-methyl-2H-1,2,4-benzothiadiazine-3(4H)-one 1,1-dioxide
mp: 124.5°-126° C.
IR (Nujol): 1690, 1595, 1325, 1310, 1300, 1175 cm$^{-1}$.
NMR (DMSO-d$_6$, δ): 1.0-1.5 (3H, m), 1.55-1.9 (5H, m), 2.05-2.35 (2H, m), 3.45 (3H, s), 3.90 (3H, s), 4.15-4.4 (1H, m), 6.95 (1H, d, J=8.3 Hz), 6.97 (1H, s), 7.78 (1H, d, J=8.3 Hz).

(34) 6-Isopropoxy-4-methyl-2-(2-pyridyl)-2H-1,2,4-benzothiadiazine-3(4H)-one 1,1-dioxide
mp: 173°-174° C.
IR (Nujol): 1700, 1600 1590, 1340, 1215 cm$^{-1}$.
NMR (CDCl$_3$, δ): 1.40 (6H, d, J=6 Hz), 3.53 (3H, s), 4.6-4.8 (1H, m), 6.73-6.85 (2H, m), 7.35-7.55 (2H, m), 7.82 (1H, d, J=8.7 Hz), 7.8-7.95 (1H, m), 8.6-8.68 (1H, m).

(35) 6-Methoxy-4-methyl-2-pentyl-2H-1,2,4-benzothiadiazine-3(4H)-one 1,1-dioxide
mp: 85°-88° C.
IR (Nujol): 1690, 1600, 1450, 1330, 1310, 1180 cm$^{-1}$.
NMR (DMSO-d$_6$, δ): 0.84 (3H, t, J=6 Hz), 1.10-1.40 (4H, m), 1.50-1.75 (2H, m), 3.47 (3H, s), 3.75 (2H, t, J=7 Hz), 3.91 (3H, s), 6.90-7.05 (2H, m), 7.82 (1H, d, J=9 Hz).

(36) 6-Methoxy-2-(4-methoxycarbonylphenyl)-4-methyl-2H-1,2,4-benzothiadiazine-3(4H)-one 1,1-dioxide
mp: 153°-156° C.
IR (Nujol): 1725, 1690, 1590, 1320, 1280 cm$^{-1}$.
NMR (DMSO-d$_6$, δ): 3.52 (3H, s), 3.89 (3H, s), 3.95 (3H, s), 6.97-7.13 (2H, m), 7.55 and 8.10 (4H, ABq, J=8.3 Hz), 7.90 (1H, d, J=8.8 Hz).

(37) 6-Cyclohexylmethoxy-4-methyl-2-(2-pyridyl)-2H-1,2,4-benzothiadiazine-3(4H)-one 1,1-dioxide
mp: 161.5°-162.5° C.
IR (Nujol): 1700, 1600, 1310 cm$^{-1}$.
NMR (CDCl$_3$, δ): 0.95-1.45 (5H, m), 1.65-2.0 (6H, m), 3.54 (3H, s), 3.86 (2H, d, J=6 Hz), 6.73-6.85 (2H, m) 7.35-7.55 (2H, m) 7.82 (1H, d, J=8.5 Hz), 7.81-7.95 (1H, m), 8.6-8.67 (1H, m).
( 38) 2-(4-Methoxycarbonylmethylphenyl)-6-methoxy-4-methyl-2H-1,2,4-benzothiadiazine-3(4H)-one 1,1-dioxide mp: 173°–176° C.

IR (Nujol): 1735, 1690, 1600, 1335, 1320 cm$^{-1}$.

NMR (DMSO-d$_6$, δ): 3.52 (3H, s), 3.65 (3H, s), 3.79 (2H, s), 3.95 (3H, s), 6.96–7.10 (2H, m), 7.33 and 7.43 (4H, ABq, J=8.3 Hz), 7.88 (1H, d, J=8.7 Hz).

(39) 2-(3-Ethoxycarbonylpropyl)-6-methoxy-4-methyl-2H-1,2,4-benzothiadiazine-3(4H)-one 1,1-dioxide mp: 63°–65° C.

IR (Nujol): 1740, 1690, 1600, 1480, 1380, 1360, 1340, 1320, 1180 cm$^{-1}$.

NMR (CDCl$_3$, δ): 1.23 (3H, t, J=7 Hz), 2.06 (2H, m), 2.37 (2H, t, J=7 Hz), 3.49 (3H, s), 3.90 (3H, s), 3.96 (2H, t, J=7 Hz), 4.09 (2H, q, J=7 Hz), 6.69 (1H, d, J=2 Hz), 6.80 (1H, dd, J=2 Hz and 9 Hz), 7.79 (1H, d, J=9 Hz).

(40) 2-[2-(4,6-Dimethylpyridyl)]-6-isopropoxy-4-methyl-2H-1,2,4-benzothiadiazine-3(4H)-one 1,1-dioxide mp: 202°–203° C.

IR (Nujol): 700, 1600, 1580, 1350, 1320, 1180 cm$^{-1}$.

NMR (DMSO-d$_6$, δ): 1.37 (6H, d, J=6 Hz), 2.34 (3H, s), 2.48 (3H, s), 3.49 (3H, s), 4.89 (1H, m), 7.01 (1H, d, J=9 Hz), 7.04 (1H, s), 7.13 (1H, s), 7.25 (1H, s), 7.80 (1H, d, J=9 Hz).

(41) 6-Isopropoxy-4-methyl-2-(2-pyrimidinyl)-2H-1,2,4-benzothiadiazine-3(4H)-one 1,1-dioxide mp: 176°–178° C.

IR (Nujol): 1700, 1600, 1400, 1380, 1350, 1330, 1280, 1230 cm$^{-1}$.

NMR (DMSO-d$_6$, δ): 1.33 (6H, d, J=6 Hz), 3.53 (3H, s), 4.90 (1H, m), 7.00 (1H, dd, J=2 Hz and 9 Hz), 7.10 (1H, d, J=2 Hz), 7.67 (1H, t, J=4 Hz), 7.84 (1H, t, J=9 Hz), 8.97 (2H, d, J=4Hz).

(42) 6-Methoxy-4-methyl-2-(4-phenoxyphenyl)-2H-1,2,4-benzothiadiazine-3(4H)-one 1,1-dioxide mp: 184°–186° C.

IR (Nujol): 1690, 1590, 1330, 1180 cm$^{-1}$.

NMR (DMSO-d$_6$, δ): 3.52 (3H, s), 3.94 (3H, s), 6.95–7.55 (11H, m), 7.89 (1H, d, J=9 Hz).

(43) 2-(4-Isopropylphenyl)-6-methoxy-4-methyl-2H-1,2,4-benzothiadiazine-3(4H)-one 1,1-dioxide mp: 158°–159° C.

IR (Nujol): 1700, 1595, 1330, 1310, 1125 cm$^{-1}$.

NMR (DMSO-d$_6$, δ): 1.24 (6H, d, J=7 Hz), 2.98 (1H, m), 3.51 (3H, s), 3.94 (3H, s), 7.01 (1H, dd, J=2 Hz and 9 Hz), 7.06 (1H, d, J=2 Hz), 7.27 and 7.39 (4H, ABq, J=8 Hz), 7.87 (1H, d, J=9 Hz).

(44) 2-[(3-Chloro-4-methyl)phenyl]-6-methoxy-4-methyl-2H-1,2,4-benzothiadiazine-3(4H)-one 1,1-dioxide mp: 208°–211° C.

IR (Nujol): 1695, 1595, 1315, 1180 cm$^{-1}$.

NMR (DMSO-d$_6$, δ): 2.40 (3H, s), 3.51 (3H, s), 3.94 (3H, s), 7.02 (1H, dd, J=2 Hz and 9 Hz), 7.07 (1H, d, J=2 Hz), 7.39 (1H, dd, J=2 Hz and 8 Hz), 7.46 (1H, d, J=2 Hz), 7.52 (1H, d, J=8 Hz), 7.89 (1H, d, J=9 Hz).

(45) 6-Methoxy-4-methyl-2-(4-methylthiophenyl)-2H-1,2,4-benzothiadiazine-3(4H)-one 1,1-dioxide mp: 154°–155° C.

IR (Nujol): 1690, 1610, 1580, 1490, 1310, 1185, 1135 cm$^{-1}$.

NMR (CDCl$_3$, δ): 2.51 (3H, s), 3.54 (3H, s), 3.93 (3H, s), 6.76 (1H, d, J=2 Hz), 6.83 (1H, dd, J=2 Hz and 9 Hz), 7.32 (4H, s), 7.85 (1H, d, J=9 Hz).

(46) 2-(4-Dimethylaminophenyl)-6-methoxy-4-methyl-2H-1,2,4-benzothiadiazine-3(4H)-one 1,1-dioxide mp: 244°–245° C.

IR (Nujol): 1690, 1600, 1520, 1330, 1310, 1180, 1130 cm$^{-1}$.

NMR (DMSO-d$_6$, δ): 2.96 (6H, s), 3.50 (3H, s), 3.94 (3H, s), 6.75 (2H, d, J=9 Hz), 7.10 (2H, d, J=9 Hz), 7.02 (1H, dd, J=2 Hz and 9 Hz), 7.02 (1H, d, J=2 Hz), 7.85 (1H, d, J=9 Hz).

(47) 2-(4-Caboxymethylphenyl)-6-isopropoxy-4-methyl-2H-1,2,4-benzothiadiazine-3(4H)-one 1,1-dioxide mp 232°–233° C.

IR (Nujol) 3600–2500, 1700, 1685, 1600 cm$^{-1}$.

NMR (DMSO-d$_6$, δ): 1.34 (6H, d, J=6.0 Hz), 3.49 (3H, s), 3.66 (2H, s), 4.8–5.0 (1H, m), 6.95–7.01 (2H, m), 7.30 and 7.40 (4H, ABq, J=8.0 Hz), 7.84 (1H, d, J=9.0 Hz).

(48) 2-(4-Carboxyphenyl)-6-isopropoxy-4-methyl-2H-1,2,4-benzothiadiazine-3(4H)-one 1,1-dioxide mp: 247.5°–248.5° C.

IR (Nujol): 3200–2400, 1690, 1605 cm$^{-1}$.

NMR (DMSO-d$_6$, δ): 1.34 (6H, d, J=6.0 Hz), 3.50 (3H, s), 4.80–5.0 (1H, m), 6.95–7.07 (2H, m), 7.51 and 8.09 (4H, ABq, J=8.3 Hz), 7.86 (1H, d, J=8.4 Hz), 13.3 (1H, br s).

(49) 2-(3-Carboxypropyl)-6-isopropoxy-4-methyl-2H-1,2,4-benzothiadiazine-3(4H)-one 1,1-dioxide mp: 150°–152° C.

IR (Nujol): 1710, 1690, 1600, 1580, 1470, 1380, 1100 cm$^{-1}$.

NMR (CDCl$_3$, δ): 1.38 (6H, d, J=6 Hz), 2.05 (2H, m), 2.43 (2H, t, J=7 Hz), 3.46 (3H, s), 3.98 (2H, t, J=7 Hz), 4.67 (1H, m), 6.67 (1H, d, J=2 Hz), 6.76 (1H, dd, J=2 Hz and 9 Hz), 7.76 (1H, d, J=9 Hz).

(50) 2-(4-Carboxyphenyl)-6-cyclohexylmethoxy-4-methyl-2H-1,2,4-benzothiadiazine-3(4H)-one 1,1-dioxide mp: 240.5°–241° C.

IR (Nujol): 3300–2400, 1690, 1600, 1330 cm$^{-1}$.

NMR (DMSO-d$_6$, δ): 1.40–1.95 (5H, m), 1.55–1.95 (6H, m), 3.52 (3H, s), 4.00 (1H, d, J=5.8 Hz), 6.95–7.10 (2H, m), 7.50 and 8.05 (4H, ABq, J=8.3 Hz), 7.86 (1H, d, J=8.7 Hz), 13.3 (1H, br s).

(51) 7-Chloro-6-isopropoxy-4-methyl-2-(2-pyridyl)-2H-1,2,4-benzothiadiazine-3(4H)-one 1,1-dioxide (115 mg) as colorless needles mp: 193°–194° C.

IR (Nujol): 1685, 1590, 1345 cm$^{-1}$.

NMR (CDCl$_3$, δ): 1.46 (6H, d, J=6 Hz), 3.55 (3H, s), 4.6–4.85 (1H, m), 6.75 (1H, s), 7.35–7.55 (2H, m), 7.90 (1H, s), 7.85–7.95 (1H, m), 8.6–8.7 (1H, m).

EXAMPLE 9

A suspension of 6-hydroxy-4-methyl-2-(4-trifluoromethylphenyl)-2H-1,2,4-benzothiadiazine-3(4H)-one 1,1-dioxide (124 mg), potassium carbonate (55 mg) and 2-iodopropane (68 mg) in N,N-dimethyl formamide (1 ml) was stirred for 2 hours at 60° C. The mixture was poured into ice water. The separated solid was collected by filtration, dried, and recrystallized from ethanol to yield 2-(4-trifluoromethylphenyl)-4-methyl-6-isopropoxy-2H-1,2,4-benzothiadiazine-3(4H)-one 1,1-dioxide (78 mg).

mp: 158°–160° C.

IR (Nujol): 1690, 1600, 1460, 1370, 1320, 1130 cm$^{-1}$.

NMR (DMSO-d$_6$, δ): 1.34 (6H, d, J=6 Hz), 3.50 (3H, s), 4.90 (1H, m), 7.00–7.10 (2H, m), 7.64 (2H, d, J=7 Hz), 7.80–8.00 (3H, m).

EXAMPLE 10

A suspension of 2-(4-chlorophenyl)-6-hydroxy-4-methyl-2H-1,2,4-benzothiadiazine-3(4H)-one 1,1-dioxide (250 mg), potassium carbonate (122 mg) and 1-iodoisobutane (163 mg) in N,Ndimethyl formamide (1 ml) was stirred for 2 hours at 60° C. The mixture was poured into ice water. The separated solid was collected by filtration, dried, and recrystallized from ethanol to yield 2-(4-chlorophenyl)-4-methyl-6-(2-methylpropoxy)-2H-1,2,4-benzothiadiazine-3(4H)-one 1,1-dioxide (169 mg).

mp: 108°–110° C.

IR (Nujol): 1690, 1600, 1580, 1460, 1340, 1320, 1190 cm$^{-1}$.

NMR (DMSO-d$_6$, δ): 1.02 (6H, d, J=7 Hz), 2.08 (1H, m), 3.51 (3H, s), 3.95 (2H, d, J=8 Hz), 6.99–7.06 (2H, m), 7.39–7.63 (4H, m), 7.87 (1H, d, J=9 Hz).

EXAMPLE 11

A suspension of 2-(4-chlorophenyl)-6-hydroxy-4-methyl-2H-1,2,4-benzothiadiazine-3(4H)-one 1,1-dioxide (250 mg), potassium carbonate (122 mg) and bromomethylyclohexane (159 mg) in N,N-dimethyl formamide (1 ml) was stirred for 2 hours at 60° C. The mixture was poured into ice water. The separator solid was collected by filtration, dried, and recrystallized from ethanol to yield 2-(4-chlorophenyl)-4-methyl-6-cyclohexylmethoxy-2H-1,2,4-benzothiadiazine-3(4H)-one 1,1-dioxide (230 mg).

mp: 127°–129° C.

IR (Nujol): 1690, 1600, 1590, 1460, 1320, 1310, 1180, 1130 cm$^{-1}$.

NMR (DMSO-d$_6$, δ): 1.04–1.40 (5H, m), 1.50–1.90 (6H, m), 3.50 (3H, s), 3.98 (2H, d, J=6 Hz), 6.98–7.05 (2H, m), 7.38–7.63 (4H, m), 7.86 (1H, d, J=9 Hz).

EXAMPLE 12

A mixture of 2-(4-chlorophenyl)-6-hydroxy-4-methyl-2H-1,2,4-benzothiadiazine-3(4H)-one 1,1-dioxide (500 mg), ethyl bromoacetate (0.2 ml), and potassium carbonate (245 mg) in N,N-dimethyl formamide (1 ml) was stirred at 80° C. for 3 hours. The mixture was cooled and poured into ice-water. The separated solid was filtered and dissolved in a mixture of ethanol (15 ml) and tetrahydrofuran (15 ml). To the solution containing 2-(4-chlorophenyl)-6-ethoxycarbonylmethoxy-4-methyl-2H-1,2,4-benzothiadiazine-3(4H)-one 1,1-dioxide was added aqueous 1N-sodium hydroxide solution (2.2 ml) in one portion at ambient temperature. The solution was stirred for one hour at ambient temperature and concentrated in vacuo. The residue was extracted with methylene chloride. The organic layer washed with brine, dried, and evaporated to give the crude product, which was crystallized from methanol to yield 2-(4-chlorophenyl)-6-carboxymethoxy-4-methyl-2H-1,2,4-benzothiadiazine-3(4H)-one 1,1-dioxide (213 mg).

mp: 228°–230° C.

IR (Nujol): 1730, 1690, 1600, 1460, 1340, 1320 cm$^{-1}$.

NMR (DMSO-d$_6$, δ): 3.34 (1H, brs), 3.50 (3H, s), 4.95 (2H, s), 6.99 (1H, dd, J=9 Hz and 2 Hz), 7.11 (1H, d, J=2 Hz), 7.35–7.65 (4H, m), 7.89 (1H, d, J=9 Hz).

EXAMPLE 13

A mixture of 2-(4-chlorophenyl)-6-hydroxy-4-methyl-2H-1,2,4-benzothiadiazine-3(4H)-one 1,1-dioxide (678 mg), ethyl 2-bromopropionate (362 mg), and potassium carbonate (207 mg) in dry N,N-dimethyl formamide (2 ml) was stirred overnight at ambient temperature. The mixture was poured into water and extracted twice with ethyl acetate. The organic layers were washed with water, dried, and evaporated under reduced pressure. The residue was crystallized from n-hexane to yield 2-(4-chlorophenyl)-6-[1-(ethoxycarbonyl)ethoxy]-4-methyl-2H-1,2,4-benzothiadiazine-3(4H)-one 1,1-dioxide (816 mg). (R,S mixture)

mp: 111°–112° C.

IR (Nujol): 1750, 1690, 1605, 1340, 1210, 1140 cm$^{-1}$.

NMR (CDCl$_3$, δ): 1.29 (3H, t, J=7.1 Hz), 1.69 (3H, d, J=6.7 Hz), 3.52 (3H, s), 4.26 (2H, q, J=7.1 Hz), 4.88 (1H, q, J=6.7 Hz), 6.73 (1H, dd, J=8.7 Hz and 2.0 Hz), 6.84 (1H, d, J=2.0 Hz), 7.35 and 7.46 (4H, ABq, J=8.6 Hz), 7.83 (1H, d, J=8.7 Hz).

EXAMPLE 14

To a suspension of 2-(4-chlorophenyl)-6-[1-(ethoxycarbonyl)ethoxy]-4-methyl-2H-1,2,4-benzothiadiazine-3(4H)-one 1,1-dioxide (400 mg) in a mixture of ethanol (5 ml) and water (5 ml) was added aqueous 1N-sodium hydroxide solution (1.1) ml in one portion. The mixture was refluxed for half hour and concentrated in vacuo. The residue was dissolved in water and washed with ethyl ether. The aqueous layer was acidified with hydrochlonic acid. The separated oil was extracted with ethyl acetate. The organic layer was washed with brine, dried, and evaporated to dryness. The residue was crystallized from a mixture of n-hexane and ethyl acetate to yield 2-(4-chlorophenyl)-6-(1-carboxyethoxy)-4-methyl-2H-1,2,4-benzothiadiazine-3(4H)-one 1,1-dioxide (240 mg).

mp: 179.5°–180.5° C. (R,S mixture).

IR (Nujol): 3250, 1760, 1665, 1600, 1350 cm$^{-1}$.

NMR (CDCl$_3$, δ): 1.74 (3H, d, J=6.7 Hz), 3.52 (3H, s), 4.94 (1H, q, J=6.7 Hz), 5.54 (1H, brs), 6.76 (1H, dd, J=1.9 Hz and 8.7 Hz), 7.40 (4H, ABq, J=8.6 Hz), 7.85 (1H, d, J=8.7 Hz).

EXAMPLE 15

In a similar manner to that of Example 13, there were obtained the following compounds.

(1) 2-(4-Chlorophenyl)-6-(1-ethoxycarbonyl-1-methyl-ethoxy)-4-methyl-2H-1,2,4-benzothiadiazine-3(4H)-one 1,1-dioxide mp: 184°–185° C.

IR (Nujol): 1720, 1700, 1580, 1370, 1340, cm$^{-1}$.

NMR (CDCl$_3$, δ): 1.30 (3H, t, J=7 Hz), 1.73 (6H, s), 3.53 (3H, s), 4.28 (2H, q, J=7 Hz), 6.68 (1H, dd, J=9 Hz and 2 Hz), 6.80 (1H, d, J=2 Hz), 7.37 (2H, d, J=9 Hz), 7.50 (2H, d, J=9 Hz), 7.81 (1H, d, J=9 Hz).

(2) 2-(4-Chlorophenyl)-6-(3-ethoxycarbonylpropoxy)-4-methyl-2H-1,2,4-benzothiadiazine-3(4H)-one 1,1 dioxide mp: 90°–92° C.

IR (Nujol): 1730, 1700, 1600, 1580, 1470, 1330, 1320 cm$^{-1}$.

NMR (CDCl$_3$, δ): 1.28 (3H, t, J=7 Hz), 2.17 (2H, m), 2.54 (2H, t, J=7 Hz), 3.54 (3H, s), 4.15(2H, t, J=7 Hz), 4.17 (2H, q, J=7 Hz), 6.70–6.90 (2H, m), 7.30–7.55 (4H, m), 7.84 (1H, d, J=9 Hz).

(3) 2-(4-Chlorophenyl)-6-(1-ethoxycarbonylpropoxy)-4-methyl-2H-1,2,4-benzothiadiazine-3(4H)-one 1,1-dioxide.

mp: 105°–108° C.

IR (Nujol): 1750, 1690, 1600, 1580, 1210 cm$^{-1}$.

NMR (CDCl$_3$, δ): 1.11 (3H, t, J=7 Hz), 1.29 (3H, t, J=7 Hz), 2.06 (2H, m), 3.50 (3H, s), 4.26 (2H, q, J=7 Hz), 4.69 (1H, t, J=6 Hz), 6.74 (1H, dd, J=9 Hz and 6 Hz), 6.84 (1H, d, J=2 Hz), 7.30-7.50 (4H, m), 7.83 (1H, d, J=9 Hz).

(4) 2-(4-Chlorophenyl)-6-(1-ethoxycarbonylcyclobutyloxy)-4-methyl-2H-1,2,4-benzothiadiazine-3(4H)-one 1,1-dioxide mp: 140°-142° C.

IR (Nujol): 1730, 1690, 1610, 1590, 1360 cm$^{-1}$.

NMR (CDCl$_3$, δ): 1.69 (3H, t, J=7 Hz), 1.85-2.90 (6H, m), 3.46 (3H, s), 4.20 (2H, q, J=7 Hz), 6.57 (1H, dd, J=9 Hz and 2 Hz), 6.92 (1H, d, J=2 Hz), 7.41 (2H, d, J=8 Hz), 7.60 (2H, d, J=8 Hz), 7.87 (1H, d, J=9 Hz).

(5) 2-(4-Chlorophenyl)-6-(1-carboxyethoxy)-4-methyl-2H-1,2,4-benzothiadiazine-3(4H)-one 1,1-dioxide mp: 179.5°-180.5° C. (R,S mixture).

IR (Nujol): 3250, 1760, 1665, 1600, 1350 cm$^{-1}$.

NMR (CDCl$_3$, δ): 1.74 (3H, d, J=6.7 Hz), 3.52 (3H, s), 4.94 (1H, q, J=6.7 Hz), 5.54 (1H, brs), 6.76 (1H, dd, J=1.9 Hz and 8.7 Hz), 7.40 (4H, ABq, J=8.6 Hz), 7.85 (1H, d, J=8.7 Hz).

(6) 2-(4-Chlorophenyl)-6-(1-carboxy-1-methylethoxy)-4-methyl-2H-1,2,4-benzothiadiazine-3(4H)-one 1,1-dioxide mp: 208°-210° C.

IR (Nujol): 3250, 1750, 1670, 1600, 1350, 1330 cm$^{-1}$.

NMR (CDCl$_3$, δ): 1.75 (6H, s), 3.51 (3H, s), 6.74 (1H, dd, J=9 Hz and 2 Hz), 6.83 (1H, d, J=2 Hz), 7.34 (2H, d, J=9 Hz), 7.46 (2H, d, J=9 Hz), 7.82 (1H, d, J=9 Hz).

(7) 2-(4-Chlorophenyl)-6-(3-carboxypropoxy)-4-methyl-2H-1,2,4-benzothiadiazine-3(4H)-one 1,1-dioxide mp: 170°-171° C.

IR (Nujol): 1700, 1600, 1580, 1330, 1310 cm$^{-1}$. NMR (CDCl$_3$, δ): 2.19 (2H, m), 2.62 (2H, t, J=7 Hz), 3.54 (3H, s), 4.17 (2H, t, J=6 Hz), 6.70-6.90 (2H, m), 7.35 (2H, d, J=9 Hz), 7.47 (2H, d, J=9 Hz), 7.84 (1H, d, J=9 Hz).

(8) 2-(4-Chlorophenyl)-6-(1-carboxypropoxy)-4-methyl-2H-1,2,4-benzothiadiazine-3(4H)-one 1,1-dioxide mp: 179°-181° C.

IR (Nujol): 3250, 1760, 1680, 1600, 1590, 1380, 1200 cm$^{-1}$.

NMR (CDCl$_3$, δ): 1.15 (3H, t, J=7 Hz), 2.11 (2H, m), 3.53 (3H, s), 4.78 (1H, t, J=6 Hz), 6.76 (1H, dd, J=9 Hz and 2 Hz), 6.86 (1H, d, J=2 Hz), 7.30-7.50 (4H, m), 7.85 (1H, d, J=9 Hz).

(9) 2-(4-Chlorophenyl)-6-(1-carboxycyclobutyloxy)-4-methyl-2H-1,2,4-benzothiadiazine-3(4H)-one 1,1-dioxide mp: 148°-151° C.

IR (Nujol): 1700, 1600, 1380, 1320, 1180 cm$^{-1}$.

NMR (CDCl$_3$, δ): 2.00-2.30 (2H, m), 2.50-2.75 (2H, m), 2.78-2.95 (2H, m), 3.51 (3H, s), 6.53 (1H, dd, J=9 Hz and 2 Hz), 6.73 (1H, d, J=2 Hz), 7.34 (2H, d, J=9 Hz), 7.46 (2H, d, J=9 Hz), 7.80 (1H, d, J=9 Hz).

(10) (1R)-(+)-2-(4-Chlorophenyl)-6-[1-(ethoxycarbonyl)ethoxy-]-4-methyl-2H-1,2,4-benzothiadiazine-3(4H)-one 1,1-dioxide mp: 86°-88° C.

[α]$_D$+24.0° (C=1.0,EtOH).

IR (Nujol): 1740, 1690, 1680, 1600, 1590, 1500, 1210, 1185 cm$^{-1}$.

NMR (CDCl$_3$, δ): 1.30 (3H, t, J=7 Hz), 1.69 (3H, d, J=7 Hz), 3.53 (3H, s), 4.26 (2H, q, J=7 Hz), 4.87 (1H, q, J=7 Hz), 6.74 (1H, dd, J=2 Hz and 9 Hz), 6.83 (1H, d, J=9 Hz), 7.35 (2H, d, J=9 Hz), 7.46 (2H, d, J=9 Hz), 7.83 (1H, d, J=9 Hz)

(11) (1S)-(−)-2-(4-Chlorophenyl)-6-[1-(ethoxycarbonyl)ethoxy]-4-methyl-2H-1,2,4-benzothiadiazine-3(4H)-one 1,1-dioxide mp: 96°-98° C.

[α]$_D$−24.7° (C=1.0, EtOH).

IR (Nujol): 1730, 1690, 1680, 1600, 1590, 1340, 1190 cm$^{-1}$.

NMR (CDCl$_3$, δ): 1.29 (3H, t, J=7 Hz), 1.69 (3H, d, J=7 Hz), 3.52 (3H, s), 4.26 (2H, q, J=7 Hz), 4.88 (1H, q, J=7 Hz), 6.74 (1H, d, J=9 Hz), 6.83 (1H, s), 7.35 (2H, d, J=9 Hz), 7.46 (2H, d, J=9 Hz), 7.83 (1H, d, J=9 Hz).

(12) (1R)-(+)-2-(4-Chlorophenyl)-6-(1-carboxyethoxy)-4-methyl-2H-1,2,4-benzothiadiazine-3(4H)-one 1,1-dioxide mp: 75°-85 ° C.

[α]$_D$+16.4° (C=1.0, EtOH).

IR (Nujol): 3200, 1740, 1700, 1690, 1660, 1600, 1580, 1380, 1130 cm$^{-1}$.

NMR (CDCl$_3$, δ): 1.77 (3H, d, J=7 Hz), 3.55 (3H, s), 4.98 (1H, q, J=7 Hz), 6.79 (1H, dd, J=2 Hz and 9 Hz), 6.88 (1H, d, J=2 Hz), 7.37 (2H, d, J=9 Hz), 7.49 (2H, d, J=9 Hz), 7.88 (1H, d, J=9 Hz).

(13) (1S)-(−)-2-(4-Chlorophenyl)-6-(1-carboxyethoxy)-4-methyl-2H-1,2,4-benzothiadiazine-3(4H)-one 1,1-dioxide mp: 85°-95 ° C.

[α]$_D$−17.0° (C=1.0, EtOH)

IR (Nujol): 3200, 1740, 1700, 1665, 1600, 1580, 1200, 1130, cm$^{-1}$.

NMR (CDCl$_3$, δ): 1.75 (3H, d, J=7 Hz), 3.52 (3H, s), 4.95 (1H, q, J=7 Hz), 6.50 (1H, bs), 6.75 (1H, dd, J=2 Hz and 9 Hz), 6.88 (1H, d, J=2 Hz), 7.32 (2H, d, J=9 Hz), 7.45 (2H, d, J=9 Hz), 7.85 (1H, d, J=9 Hz).

(14) (1R)-(+)-6-[1-(Ethoxycarbonyl)ethoxy]-4-methyl-2-phenyl-2H-1,2,4-benzothiadiazine-3(4H)-one 1,1-dioxide mp: 137.5°-139° C.

IR (Nujol): 1740, 1700, 1605, 1340, 1210, 1140 cm$^{-1}$.

NMR (CDCl$_3$, δ): 1.30 (3H, t, J=7 Hz), 1.69 (3H, d, J=7 Hz), 3.53 (3H, s), 4.26 (2H, q, J=7 Hz), 4.88 (1H, q, J=7 Hz), 6.73 (1H, dd, J=2 Hz and 9 Hz), 6.84 (1H, d, J=2 Hz), 7.35-7.55 (5H, m), 7.84 (1H, d, J=9 Hz).

(15) (1R)-(+)-6-[1-(Ethoxycarbonyl)ethoxy]-4-methyl-2-(4-phenoxyphenyl)-2H-1,2,4-benzothiadiazine-3(4H)-one 1,1-dioxide mp: 128°-130° C.

IR (Nujol): 1740, 1685, 1610, 1330, 1195, 1130 cm$^{-1}$.

NMR (CDCl$_3$, δ): 1.29 (3H, t, J=7 Hz), 1.69 (3H, d, J=7 Hz), 3.53 (3H, s), 4.26 (2H, q, J=7 Hz), 4.88 (1H, q, J=7 Hz), 6.75 (1H, dd, J=2 Hz and 9 Hz), 6.83 (1H, d, J=2 Hz), 7.0-7.45 (9H, m), 7.85 (1H, d, J=9 Hz).

(16) (1R)-(+)-6-[1-(Ethoxycarbonyl)ethoxy]-2-(4-isopropylphenyl)-4-methyl-2H-1,2,4-benzothiadiazine-3(4H)-one 1,1-dioxide mp: 154°-155° C.

IR (Nujol): 1740, 1695, 1600, 1340, 1310, 1200, 1130 cm$^{-1}$.

NMR (CDCl$_3$, δ): 1.27 (6H, d, J=7 Hz), 1.29 (3H, t, J=7 Hz), 1.69 (3H, d, J=7 Hz), 2.95 (1H, m), 3.52 (3H, s), 4.26 (2H, q, J=7 Hz), 4.88 (1H, q, J=7 Hz), 6.73 (1H, dd, J=2 Hz and 9 Hz), 6.83 (1H, d, J=2 Hz), 7.32 (4H, s), 7.83 (1H, d, J=9 Hz). (17) (1R)-(+)-2-[(3-Chloro-4- methyl)phenyl]-6-[1-(ethoxycarbonyl)ethoxy]-4-methyl-2H-1,2,4-benzothiadiazine-3(4H)-one 1,1-dioxide mp: 149°–150° C.

IR (Nujol): 1740, 1685, 1600, 1335 cm$^{-1}$.

NMR (DMSO-d$_6$, δ): 1.21 (3H, t, J=7 Hz), 1.58 (3H, d, J=7 Hz), 2.40 (3H, s), 3.48 (3H, s), 4.18 (2H, q, J=7 Hz), 5.33 (1H, q, J=7 Hz), 6.95 (1H, dd, J=2 Hz and 9 Hz), 7.08 (1H, d, J=2 Hz), 7.30 (1H, dd, J=2 Hz and 8 Hz), 7.47 (1H, d, J=2 Hz), 7.51 (1H, d, J=8 Hz), 7.87 (1H, d, J=9 Hz).

(18) (1R)-(+)-2-Cyclohexyl-6-[1-(ethoxycarbonyl)ethoxy]-4-methyl-2H-1,2,4-benzothiadiazine-3(4H)-one 1,1-dioxide mp: 139°–141° C.

IR (Nujol): 1740, 1690, 1600, 1580, 1340, 1300, 1200, 1170 cm$^{-1}$.

NMR (CDCl$_3$, δ): 1.28 (3H, t, J=6 Hz), 1.16–1.45 (3H, m), 1.66 (3H, d, J=6 Hz), 1.80–1.92 (5H, m), 2.22–2.42 (2H, m), 3.44 (3H, s), 4.23 (2H, q, J=6 Hz), 4.29–4.49 (1H, m), 4.83 (1H, q, J=6 Hz), 6.65 (1H, dd, J=2 Hz and 8 Hz), 6.71 (1H, d, J=2 Hz), 7.74 (1H, d, J=6 Hz).

(19) (1R)-(+)-6-[1-(Ethoxycarbonyl)ethoxy]-4-methyl-2-(4-methylphenyl)-2H-1,2,4-benzothiadiazine-(3(4H)-one 1,1-dioxide mp: 134°–135° C.

IR (Nujol): 1740, 1680, 1600, 1580, 1340, 1320, 1200, 1130 cm$^{-1}$.

NMR (CDCl$_3$, δ): 1.30 (3H, t, J=6 Hz), 1.69 (3H, d, J=6 Hz), 2.40 (3H, s), 3.52 (3H, s), 4.25 (2H, q, J=6 Hz), 4.88 (1H, q, J=6 Hz), 6.70 (1H, dd, J=2 Hz and 8 Hz), 6.82 (1H, d, J=2 Hz), 7.28 (4H, s), 7.83 (1H, d, J=8 Hz).

(20) (1R)-(+)-6-[1-(Ethoxycarbonyl)ethoxy]-4-methyl-2-(2-pyridyl)-2H-1,2,4-benzothiadiazine-3(4H)-one 1,1-dioxide mp: 153°–154° C.

IR (Nujol): 1740, 1690, 1605, 1580, 1460, 1330, 1205, 1115 cm$^{-1}$.

NMR (CDCl$_3$, δ): 1.29 (3H, t, J=7 Hz), 1.69 (3H, d, J=7 Hz), 3.53 (3H, s), 4.25 (2H, q, J=7 Hz), 4.86 (1H, q, J=7 Hz), 6.72 (1H, dd, J=2 Hz and 8 Hz), 6.84 (1H, d, J=2 Hz), 7.38–7.51 (2H, m), 7.82 (1H, d, J=8 Hz), 7.90 (1H, dd, J=2 Hz and 8 Hz), 8.62–8.66 (1H, m).

(21) (1R)-(+)-2-(3,4-Dichlorophenyl)-6-[1-(ethoxycarbonyl)ethoxy]-4-methyl-2H-1,2,4-benzothiadiazine-3(4H)-one 1,1-dioxide mp: 108°–110° C.

IR (Nujol): 1720, 1685, 1600, 1190, 1135 cm$^{-1}$.

NMR (CDCl$_3$, δ): 1.30 (3H, t, J=8 Hz), 1.69 (3H, d, J=7 Hz), 3.53 (3H, s), 4.29 (2H, q, J=8 Hz), 4.87 (1H, q, J=7 Hz), 6.74 (1H, dd, J=2 Hz and 9 Hz), 6.83 (1H, d, J=2 Hz), 7.28 (1H, dd, J=2 Hz and 9 Hz), 7.53 (1H, d, J=2 Hz), 7.55 (1H, d, J=9 Hz), 7.83 (1H, d, J=9 Hz).

(22) (1R)-(+)-2-(3-Chlorophenyl)-6-[1-(ethoxycarbonyl)ethoxy]-4-methyl-2H-1,2,4-benzothiadiazine-3(4H)-one 1,1-dioxide mp: 135°–137° C.

IR (Nujol): 1740, 1700, 1600, 1580, 1340, 1210 cm$^{-1}$.

NMR (CDCl$_3$, δ): 1.30 (3H, t, J=7 Hz), 1.70 (3H, d, J=7 Hz), 3.46 (3H, s), 4.27 (2H, q, J=7 Hz), 4.86 (1H, q, J=7 Hz), 6.81–7.37 (6H, m), 7.85 (1H, d, J=9 Hz).

(23) (1R)-(+)-2-(2-Chlorophenyl)-6-[1-(ethoxycarbonyl)ethoxy]-4-methyl-2H-1,2,4-benzothiadiazine-3(4H)-one 1,1-dioxide IR (CHCl$_3$): 1745, 1700, 1605, 1580, 1350, 1320, 1140 cm$^{-1}$.

NMR (CDCl$_3$, δ): 1.30 (3H, t, J=7 Hz), 1.69 (3H, d, J=7 Hz), 3.54 (3H, s), 4.27 (2H, q, J=7 Hz), 4.88 (1H, q, J=7 Hz), 6.70–7.72 (6H, m), 7.82 (1H, d, J=9 Hz).

(24) (1R)-(+)-6-[1-(Ethoxycarbonyl)ethoxy]-2-(4-fluorophenyl)-4-methyl-2H-1,2,4-benzothiadiazine(3(4H)-one 1,1-dioxide mp: 100°–102° C.

IR (Nujol): 1740, 1680, 1605, 1370, 1340 cm$^{-1}$.

NMR (CDCl$_3$, δ): 1.30 (3H, t, J=7 Hz), 1.69 (3H, d, J=7 Hz), 3.52 (3H, s), 4.26 (2H, q, J=7 Hz), 4.88 (1H, q, J=7 Hz), 6.71–7.43 (6H, m), 7.83 (1H, d, J=9 Hz).

(25) (1R)-(+)-6-[1-(Ethoxycarbonyl)ethoxy]-4-methyl-2-(4-methylthiophenyl)-2H-1,2,4-benzothiadiazine-(3(4H)-one 1,1-dioxide.

mp: 156°–157° C.

IR (Nujol): 1720, 1605, 1600, 1580, 1205, 1180 1130 cm$^{-1}$.

NMR (CDCl$_3$, δ): 1.29 (3H, t, J=7 Hz), 1.69 (3H, d, J=7 Hz), 2.50 (3H, s), 3.52 (3H, s), 4.25 (2H, q, J=7 Hz), 4.87 (1H, q, J=7 Hz), 6.72 (1H, dd, J=2 Hz and 9 Hz), 6.82 (1H, d, J=2 Hz), 7.32 (4H, s), 7.83 (1H, d, J=9 Hz).

(26) (1R)-(+)-2-(4-Dimethylaminophenyl)-6-[1-(ethoxycarbonyl)ethoxy]-4-methyl-2H-1,2,4-benzothiadiazine-3(4H)-one 1,1-dioxide mp: 190°–192° C.

IR (Nujol): 1715, 1680, 1600, 1195, 1130 cm$^{-1}$.

NMR (CDCl$_3$, δ): 1.29 (3H, t, J=7 Hz), 1.67 (3H, d, J=7 Hz), 3.00 (6H, s), 3.51 (3H, s), 4.25 (2H, q, J=7 Hz), 4.87 (1H, q, J=7 Hz), 6.69–6.81 (4H, m), 7.24 (2H, d, J=8 Hz), 7.84 (1H, d, J=8 Hz).

(27) (1R)-(+)-6-(1-Carboxyethoxy)-4-methyl-2-phenyl-2H-1,2,4-benzothiadiazine-3(4H)-one 1,1-dioxide mp: 184°–185.5° C.

IR (Nujol): 3200, 1750, 1660, 1610, 1320, 1180 cm$^{-1}$.

NMR (CDCl$_3$, δ): 1.74 (3H, d, J=7 Hz), 3.53 (3H, s), 3.55–4.1 (1H, br), 4.95 (1H, q, J=7 Hz), 6.76 (1H, dd, J=2 Hz and 9 Hz), 6.85 (1H, d, J=2 Hz), 7.35–7.55 (5H, m), 7.86 (1H, d, J=9 Hz).

(28) (1R)-(+)-6-(1-Carboxyethoxy)-4-methyl-2-(4-phenoxyphenyl)-2H-1,2,4-benzothiadiazine-3(4H)-one 1,1-dioxide mp 106° C. (dec.).

IR (Nujol): 3600–2400, 1740, 1695, 1665, 1600, 1585, 1345, 1215 cm$^{-1}$.

NMR (CDCl$_3$, δ): 1.74 (3H, d, J=7 Hz), 3.53 (3H, s), 3.63 (1H, br), 4.95 (1H, q, J=7 Hz), 6.76 (1H, dd, J=2 Hz and 9 Hz), 6.85 (1H, d, J=2 Hz), 7.0–7.45 (9H, m), 7.86 (1H, d, J=9 Hz).

(29) (1R)-(+)-6-(1-Carboxyethoxy)-2-(4-isopropylphenyl)-4-methyl-2H-1,2,4-benzothiadiazine-3(4H)-one 1,1-dioxide mp: 74° C.(dec.).

IR (Nujol): 3600–2400, 1730, 1695, 1600, 1340, 1315 cm$^{-1}$.

NMR (CDCl$_3$, δ): 1.27 (6H, d, J=7 Hz), 1.74 (3H, d, J=7 Hz), 2.76 (1H, m), 3.43 (1H, br), 3.52 (3H, s), 4.95 (1H, q, J=7 Hz), 6.76 (1H, dd, J=2 Hz and 9 Hz), 6.85 (1H, d, J=2 Hz), 7.32 (4H, s), 7.85 (1H, d, J=9 Hz).

(30) (1R)-(+)-6-(1-Carboxyethoxy)-2-[(3-chloro-4-methyl)phenyl]-4-methyl-2H-1,2,4-benzothiadiazine-3(4H)-one 1,1-dioxide mp: 184°–186° C.

IR (Nujol): 3600–2500, 1720, 1700, 1595, 1330 cm$^{-1}$.

NMR (CDCl$_3$, δ): 1.75 (3H, d, J=7 Hz), 2.42 (3H, s), 3.25 (1H, br), 3.53 (3H, s), 4.94 (1H, q, J=7 Hz), 6.77

(1H, dd, J=2 Hz and 9 Hz), 6.85 (1H, d, J=2 Hz), 7.23 (1H, dd, J=2 Hz and 8 Hz), 7.34 (1H, d, J=8 Hz), 7.41 (1H, d, J=2 Hz), 7.85 (1H, d, J=9 Hz).

(31) (1R)-(+)-6-(1-Carboxyethoxy)-4-methyl-2-(4-trifluoromethylphenyl)-2H-1,2,4-benzothiadiazine-1(4H)-one 1,1-dioxide mp: 162°–163° C.

IR (CHCl$_3$): 3600–3300, 1720, 1690, 1600, 1340, 1320, 1130 cm$^{-1}$.

NMR (CDCl$_3$, δ): 1.75 (3H, d, J=6 Hz), 3.54 (3H, s), 4.90–5.01 (1H, q, J=6 Hz), 6.77 (1H, dd, J=2 Hz and 8 Hz), 6.87 (1H, d, J=2 Hz), 7.54 (2H, d, J=8 Hz), 7.74 (2.H, d, J=8 Hz), 7.86 (1H, d, J=8 Hz).

(32) (1R)-(+)-6-(1-Carboxyethoxy)-2-cyclohexyl-4-methyl-2H-1,2,4-benzothiadiazine-3(4H)-one 1,1-dioxide mp: 76°–77° C.

IR (CHCl$_3$): 3600–2400, 1720, 1680, 1600, 1330, 1310, 1170 cm$^{-1}$.

NMR (CDCl$_3$, δ): 1.20–1.45 (3H, m), 1.70 (3H, d, J=6 Hz), 1.82–1.88 (5H, m), 2.20–2.38 (2H, m), 3.44 (3H, s), 4.35–4.47 (1H, m), 4.76 (1H, s), 4.89 (1H, q, J=6 Hz), 6.67–6.74 (2H, m), 7.75 (1H, d, J=8 Hz).

(33) (1R)-(+)-6-(1-Carboxyethoxy)-4-methyl-2-(4-methylphenyl)-2H-1,2,4-benzothiadiazine-3(4H)-one 1,1dioxide mp 182°–183° C.

IR (CHCl$_3$): 1700, 1600, 1320, 1130 cm$^{-1}$.

NMR (CDCl$_3$, δ): 1.74 (3H, d, J=6 Hz), 2.40 (3H, s), 3.17 (1H, br s), 3.52 (3H, s), 4.89–5.00 (1H, q, J=6 Hz), 6.75 (1H, dd, J=2 Hz and 8 Hz), 6.84 (1H, d, J=2 Hz), 7.29 (4H, s), 7.85 (1H, d, J=8 Hz).

(34) (1R)-(+)-6-(1-Carboxyethoxy)-4-methyl-2-(2-pyridyl)-2H-1,2,4-benzothiadiazine-3(4H)-one 1,1-dioxide mp: 142°–143° C.

IR (Nujol): 3700–2300, 1700, 1600, 1350, 1320, 1275, 1210, 1190 cm$^{-1}$.

NMR (CDCl$_3$, δ): 1.56 (3H, d, J=7 Hz), 3.47 (3H, s), 5.17 (1H, q, J=7 Hz), 6.92 (1H, dd, J=2 Hz and 9 Hz), 7.08 (1H, d, J=2 Hz), 7.45–7.60 (2H, m), 7.84 (1H, d, J=9 Hz), 8.00 (1H, m), 8.56–8.59 (1H, m).

(35) (1R)-(+)-6-(1-Carboxyethoxy)-2-(3,4-dichlorophenyl)-4-methyl-2H-1,2,4-benzothiadiazine-3(4H)-one 1,1-dioxide mp: 105°–106° C.

IR (Nujol): 3250–2400, 1735, 1690, 1600, 1585, 1300, 1290, 1175 cm$^{-1}$.

NMR (DMSO-d$_6$, δ): 1.57 (3H, d, J=7 Hz), 3.48 (3H, s), 5.20 (1H, q, J=7 Hz), 6.93 (1H, dd, J=2 Hz and 9 Hz), 7.08 (1H, d, J=2 Hz), 7.46 (1H, dd, J=2 Hz and 9 Hz), 7.76–7.93 (3H, m).

(36) (1R)-(+)-6-(1-Carboxyethoxy)-2-(3-chlorophenyl)-4-methyl-2H-1,2,4-benzothiadiazine-3(4H)-one 1,1-dioxide mp: 174°–176° C.

IR (Nujol): 1725, 1700, 1610, 1580, 1330, 1310, 1180 cm$^{-1}$.

NMR (CDCl$_3$, δ): 1.74 (3H, d, J=7 Hz), 2.72 (1H, br s), 3.53 (3H, s), 4.95 (1H, q, J=7 Hz), 6.74–7.51 (6H, m), 7.86 (1H, d, J=9 Hz).

(37) (1R)-(+)-6-(1-Carboxyethoxy)-2-(2-chlorophenyl)-4-methyl-2H-1,2,4-benzothiadiazine-3(4H)-one 1,1-dioxide mp: 110°–112° C.

IR (Nujol): 1740, 1700, 1600, 1580, 1375, 1190 cm$^{-1}$.

NMR (CDCl$_3$, δ): 1.75 (3H, d, J=7 Hz), 3.55 (3H, s), 4.95 (1H, q, J=7 Hz), 6.74–7.67 (6H, m), 7.85 (1H, d, J=9 Hz).

(38) (1R)-(+)-6-(1-Carboxyethoxy)-2-(4-fluorophenyl)-4-methyl-2H-1,2,4-benzothiadiazine-3(4H)-one 1,1-dioxide mp: 130°–132° C.

IR (Nujol): 1740, 1700, 1600, 1500, 1380, 1210 cm$^{-1}$.

NMR (CDCl$_3$, δ): 1.74 (3H, d, J=7 Hz), 3.52 (3H, s), 4.94 (1H, q, J=7 Hz), 5.80 (1H, br s), 6.74–7.43 (6H, m), 7.85 (1H, d, J=9 Hz).

(39) (1R)-(+)-6-(1-Carboxyethoxy)-4-methyl-2-(4-methylthiophenyl)-2H-1,2,4-benzothiadiazine-3(4H)-one 1,1-dioxide mp: 143°–144° C.

IR (Nujol): 3350–2300, 1730, 1660, 1600, 1580, 1190, 1090 cm$^{-1}$.

NMR (CDCl$_3$, δ): 1.74 (3H, d, J=7 Hz), 2.50 (3H, s), 3.53 (3H, s), 4.95 (1H, q, J=7 Hz), 6.76 (1H, dd, J=2 Hz and 9 Hz), 6.85 (1H, d, J=2 Hz), 7.32 (4H, s), 7.85 (1H, d, J=9 Hz).

(40) (1R)-(+)-6-(1-Carboxyethoxy)-2-(4-dimethylaminophenyl)-4-methyl-2H-1,2,4-benzothiadiazine-3(4H)-one 1,1-dioxide mp: 190° C. (dec.).

IR (KBr): 3400, 2750–2200, 1690, 1590, 1450, 1320, 1180, 1125 cm$^{-1}$.

NMR (DMSO-d$_6$, δ): 1.57 (3H, d, J=7 Hz), 2.97 (6H, s), 3.47 (3H, s), 5.22 (1H, q, J=7 Hz), 6.85 0 (2H, d, J=9 Hz), 7.15 (2H, d, J=9 Hz), 6.92 (1H, dd, J=2 Hz and 9 Hz), 7.05 (1H, d, J=2 Hz), 7.85 (1H, d, J=9 Hz).

(41) 6-[1-(Carboxy)cyclohexylmethoxy]-2-(4-chlorophenyl)-4-methyl-2H-1,2,4-benzothiadiazine-3(4H)-one 1,1-dioxide.

mp: 145°–150° C.

IR (Nujol): 3300, 1700, 1600, 1580, 1370, 1310, 1190, 1130 cm$^{-1}$.

NMR (CDCl$_3$, δ): 1.10–2.10 (11H, m), 3.40 (3H, s), 4.40 (1H, br s), 6.60 (1H, d, J=9 Hz), 6.85 (1H, s), 7.25 (2H, d, J=9 Hz), 7.43 (2H, d, J=9 Hz), 7.70 (1H, d, J=9 Hz).

EXAMPLE 16

In a similar manner to that of

EXAMPLE 14, there were obtained the following compounds.

(1) 2-(4-Chlorophenyl)-6-(1-carboxy-1-methylethoxy)-4-methyl-2H-1,2,4-benzothiadiazine-3(4H)-one 1,1-dioxide mp 208°–210° C.

IR (Nujol): 3250, 1750, 1670, 1600, 1350, 1330 cm$^{-1}$.

NMR (CDCl$_3$, δ): 1.75 (6H, s), 3.51 (3H, s), 6.74 (1H, dd, J=9 Hz and 2 Hz), 6.83 (1H, d, J=2 Hz), 7.34 (2H, d, J=9 Hz), 7.46 (2H, d, J=9 Hz), 7.82 (1H, d, J=9 Hz).

(2) 2-(4-Chlorophenyl)-6-(3-carboxypropoxy)-4-methyl-2H-1,2,4-benzothiadiazine-3(4H)-one 1,1-dioxide mp: 170°–171° C.

IR (Nujol): 1700, 1600, 1580, 1330, 1310 cm$^{-1}$.

NMR (CDCl$_3$, δ): 2.19 (2H, m), 2.62 (2H, t, J=7 Hz), 3.54 (3H, s), 4.17 (2H, t, J=6 Hz), 6.70–6.90 (2H, m), 7.35 (2H, d, J=9 Hz), 7.47 (2H, d, J=9 Hz), 7.84 (1H, d, J=9 Hz).

(3) 2-(4-Chlorophenyl)-6-(1-carboxypropoxy)-4-methyl-2H-1,2,4-benzothiadiazine 3(4H)-one 1,1-dioxide mp: 179°–181° C.

IR (Nujol): 3250, 1760, 1680, 1600, 1590, 1380, 1200 cm$^{-1}$.

NMR (CDCl$_3$, δ): 1.15 (3H, t, J=7 Hz), 2.11 (2H, m), 3.53 (3H, s), 4.78 (1H, t, J=6 Hz), 6.76 (1H, dd, J=9 Hz and 2 Hz), 6.86 (1H, d, J=2 Hz), 7.30–7.50 (4H, m), 7.85 (1H, d, J=9 Hz).

(4) 2-(4-Chlorophenyl)-6-(1-carboxycyclobutyloxy)-methyl-2H-1,2,4-benzothiadiazine-3(4H)-one 1,1-dioxide mp: 148°–151° C.

IR (Nujol): 1700, 1600, 1380, 1320, 1180 cm$^{-1}$.

NMR (CDCl$_3$, δ): 2.00–2.30 (2H, m), 2.50–2.75 (2H, m), 2.78–2.95 (2H, m), 3.51 (3H, s), 6.53 (1H, dd, J=9hz and 2 Hz), 6.73 (1H, d, J=2 Hz), 7.34 (2H, d, J=9 Hz), 7.46 (2H, d, J=9 Hz), 7.80 (1H, d, J=9 Hz).

(5) (1R)-(+)-2-(4-Chlorophenyl)-6-(1-carboxyethoxy)-4-methyl-2H-1,2,4-benzothiadiazine-3(4H)-one 1,1-dioxide mp: 75°–85° C. [α]$_D$+16.4° (C=1.0, EtOH)

IR (Nujol): 3200, 1740, 1700, 1690, 1660, 1600, 1580, 1380, 1130 cm$^{-1}$.

NMR (CDCl$_3$, δ): 1.77 (3H, d, J=7 Hz), 3.55 (3H, s), 4.98 (1H, q, J=7 Hz), 6.79 (1H, dd, J=2 Hz and 9 Hz), 6.88 (1H, d, J=2 Hz), 7.37 (2H, d, J=9 Hz), 7.49 (2H, d, J=9 Hz), 7.88 (1H, d, J=9 Hz).

(6) (1S)-(−)-2-(4-Chlorophenyl)-6-(1-carboxyethoxy)-methyl-2H-1,2,4-benzothiadiazine-3(4H)-one 1,1-dioxide mp: 85°–95° C. [α]$_D$17.0° (C=1.0, EtOH).

IR (Nujol): 3200, 1740, 1700, 1665, 1600, 1580, 1200, 1130 cm$^{-1}$.

NMR (CDCl$_3$, δ): 1.75 (3H, d, J=7 Hz), 3.52 (3H, s), 4.95 (1H, q, J=7 Hz), 6.50 (1H, bs), 6.75 H, dd, J=2 Hz and 9 Hz), 6.88 (1H, d, J=2 Hz), 7.32 (2H, d, J=9 Hz), 7.45 (2H, d, J=9 Hz), 7.85 (1H, d, J=9 Hz).

(7) (1R)-(+)-6-(1-Carboxyethoxy)-4-methyl-2-phenyl-2H-1,2,4-benzothiadiazine-3(4H)-one 1,1-dioxide mp: 184°–185.5° C.

IR (Nujol): 3200, 1750, 1660, 1610, 1320, 1180 cm$^{-1}$.

NMR (CDCl$_3$, δ): 1.74 (3H, d, J=7 Hz), 3.53 (3H, s), 3 55–4.1 (1H, br), 4.95 (1H, q, J=7 Hz) 6.76 (1H, dd, J=2 Hz and 9 Hz), 6.85 (1H, d, J=2 Hz), 7.35–7.55 (5H, m), 7.86 (1H, d, J=9 Hz).

(8) (1R)-(+)-6-(1-Carboxyethoxy)-4-methyl-2-(4-phenoxyphenyl)-2H-1,2,4-benzothiadiazine-3(4H)-one 1,1-dioxide mp: 106° C. (dec.).

IR (Nujol): 3600–2400, 1740, 1695, 1665, 1600, 1585, 1345, 1215 cm$^{-1}$.

NMR (CDCl$_3$, δ): 1.74 (3H, d, J=7 Hz), 3.53 (3H, s), 3.63 (1H, br), 4.95 (1H, q, J=7 Hz), 6.76 (1H, dd, J=2 Hz and 9 Hz), 6.85 (1H, d, J=2 Hz), 7.0–7.45 (9H, m), 7.86 (1H, d, J=9 Hz).

(9) (1R)-(+)-6-(1-Carboxyethoxy)-2-(4-isopropylphenyl)-4-methyl-2H-1,2,4-benzothiadiazine-3(4H)-one 1,1-dioxide mp: 74° C. (dec.).

IR (Nujol): 3600–2400, 1730, 1695, 1600, 1340, 1315 cm$^{-1}$.

NMR (CDCl$_3$, δ): 1.27 (6H, d, J=7 Hz), 1.74 (3H, d, J=7 Hz), 2.76 (1H, m), 3.43 (1H, br) 3.52 (3H, s), 4.95 (1H, q, J=7 Hz), 6.76 (1H, dd, J=2 Hz and 9 Hz), 6.85 (1H, d, J=2 Hz), 7.32 (4H, s), 7.85 (1H, d, J=9 Hz).

(10) (1R)-(+)-6-(1-Carboxyethoxy)-2-[(3-chloro-4-methyl)phenyl]-4-methyl)phenyl]-4-methyl-2H-1,2,4-benzothiadiazine-3(4H)-one 1,1-dioxide.

mp: 184°–186° C.

IR (Nujol): 3600–2500, 1720, 1700, 1595, 1330 cm$^{-1}$.

NMR (CDCl$_3$, δ): 1.75 (3H, d, J=7 Hz), 2.42 (3H, s), 3.25 (1H, br), 3.53 (3H, s), 4.94 (1H, q, J=7 Hz), 6.77 (1H, dd, J=2 Hz and 9 Hz), 6.85 (1H, d, J=2 Hz), 7.23 (1H, dd, J=2 Hz and 8 Hz), 7.34 (1H, d, J=8 Hz), 7.41 (1H, d, J=2 Hz), 7.85 (1H, d, J=9 Hz).

(11) (1R)-(+)-6-(1-Carboxyethoxy)-4-methyl-2-(4-trifluoromethylphenyl)-2H-1,2,4-benzothiadiazine-3(4H)-one 1,1-dioxide mp: 162°–163° C.

IR (CHCl$_3$): 3600–3300, 1720, 1690, 1600, 1340, 1320, 1130 cm$^{-1}$.

NMR (CDCl$_3$, δ): 1.75 (3H, d, J=6 Hz), 3.54 (3H, s), 4.90–5.01 (1H, q, J=6 Hz), 6.77 (1H, dd, J=2 Hz and 8 Hz), 6.87 (1H, d, J=2 Hz), 7.54 (2H, d, J=8 Hz), 7.74 (2H, d, J=8 Hz), 7.86 (1H, d, J=8 Hz).

(12) (1R)-(+)-6-(1-Carboxyethoxy)-2-cyclohexyl-4-methyl-2H-1,2,4-benzothiadiazine-3(4H)-one 1,1-dioxide mp: 76°–77° C.

IR (CHCl$_3$): 3600–2400, 1720, 1680, 1600, 1330, 1310, 1170 cm$^{-1}$.

NMR (CDCl$_3$, δ): 1.20–1.45 (3H, m), 1.70 (3H, d, J=6 Hz), 1.82–1.88 (5H, m), 2.20–2.38 (2H, m), 3.44 (3H, s), 4.35–4.47 (1H, m), 4.76 (1H, s), 4.89 (1H, q, J=6 Hz), 6.67–6.74 (2H, m), 7.75 (1H, d, J=8 Hz).

(13) (1R)-(+)-6-(1-Carboxyethoxy)-4-methyl-2-(4-methylphenyl)-2H-1,2,4-benzothiadiazine-3(4H)-one 1,1-dioxide mp: 182°–183° C.

IR (CHCl$_3$): 1700, 1600, 1320, 1130 cm$^{-1}$.

NMR (CDCl$_3$, δ): 1.74 (3H, d, J=6 Hz), 2.40 (3H, s), 3.17 (1H, br s), 3.52 (3H, s), 4.89–5.00 (1H, q, J=6 Hz), 6.75 (1H, dd, J=2 Hz and 8 Hz), 6.84 (1H, d, J=2 Hz), 7.29 (4H, s), 7.85 (1H, d, J=8 Hz).

(14) (1R)-(+)-6-(1-Carboxyethoxy)-4-methyl-2-(2-pyridyl)-2H-1,2,4-benzothiadiazine-3(4H)-one 1,1-dioxide mp: 142°–143° C.

IR (Nujol): 3700–2300, 1700, 1600, 1350, 1320, 1275, 1210, 1190 cm$^{-1}$.

NMR (CDCl$_3$, δ): 1.56 (3H, d, J=7 Hz), 3.47 (3H, s), 5.17 (1H, q, J=7 Hz), 6.92 (1H, dd, J=2 Hz and 9 Hz), 7.08 (1H, d, J=2 Hz), 7.45–7.60 (2H, m), 7.84 (1H, d, J=9 Hz), 8.00 (1H, m), 8.56–8.59 (1H, m).

(15) (1R)-(+)-6-(1-Carboxyethoxy)-2-(3,4-dichlorophenyl)-methyl-4-methyl-2H-1,2,4-benzothiadiazine-3(4H)-one 1,1-dioxide mp 105°–106° C.

IR (Nujol): 3250–2400, 1735, 1690, 1600, 1585, 1300, 1290, 1175 cm$^{-1}$.

NMR (DMSO-d$_6$, δ): 1.57 (3H, d, J=7 Hz), 3.48 (3H, s), 5.20 (1H, q, J=7 Hz), 6.93 (1H, dd, J=2 Hz and 9 Hz), 7.08 (1H, d, J=2 Hz), 7.46 (1H, dd, J=2 Hz and 9 Hz), 7.76–7.93 (3H, m) 7.46 (1H, dd, J=2 Hz and 9 Hz), 7.76–7.93 (3H, m).

(16) (1R)-(+)-6-(1-Carboxyethoxy)-2-(3-chlorophenyl)-4-methyl-2H-1,2,4-benzothiadiazine-3(4H)-one 1,1-dioxide mp: 174°–176° 176°C.

IR (Nujol): 1725, 1700, 1610, 1580, 1330, 1310, 1180 cm$^{-1}$.

NMR (CDCl$_3$, δ): 1.74 (3H, d, J=7 Hz), 2.72 (1H, br s), 3.53 (3H, s), 4.95 (1H, q, J=7 Hz), 6.74–7.51 (6H, m), 7.86 (1H, d, J=9 Hz).

(17) (1R)-(+)-6-(1-Carboxyethoxy)-2-(2-chlorophenyl)-4-methyl-2H-1,2,4-benzothiadiazine-3(4H)-one 1,1dioxide mp: 110–112° C.

IR (Nujol): 1740, 1700, 1600, 1580, 1375, 1190 cm$^{-1}$.

NMR (CDCl$_3$, δ): 1.75 (3H, d, J=7 Hz), 3.55 (3H, s), 4.95 (1H, q, J=7 Hz), 6.74–7.67 (6H, m), 7.85 (1H, d, J=9 Hz).

(18) (1R)-(+)-6-(1-Carboxyethoxy)-2-(4-fluorophenyl)-4-methyl-2H-1,2,4-benzothiadiazine-3(4H)-one 1,1dioxide mp: 130°–132° C.

IR (Nujol): 1740, 1700, 1600, 1500, 1380, 1210 cm$^{-1}$.

NMR (CDCl$_3$, δ): 1.74 (3H, d, J=7 Hz), 3.52 (3H, s), 4.94 (1H, q, J=7 Hz), 5.80 (1H, br s), 6.74–7.43 (6H, m), 7.85 (1H, d, J=9 Hz).

(19) -(+)-6-(1-Carboxyethoxy)-4-methyl-2-(4-methylthiophenyl)-2H-1,2,4-benzothiadiazine-3(4H)-one 1,1-dioxide mp: 143°–144° C.

IR (Nujol): 3350–2300, 1730, 1660, 1600, 1580, 1190, 1090 cm$^{-1}$.

NMR (CDCl$_3$, δ): 1.74 (3H, d, J=7 Hz), 2.50 (3H, s), 3.53 (3H, s), 4.95 (1H, q, J=7 Hz), 6.76 (1H, dd, J=2 Hz and 9 Hz), 6.85 (1H, d, J=2 Hz), 7.32 (4H, s), 7.85 (1H, d, J=9 Hz).

(20) (1R)-(+)-6-(1-Carboxyethoxy)-2-(4-dimethylaminophenyl)-4-methyl-2H-1,2,4-benzothiadiazine-3(4H)-one 1,1-dioxide mp: 190° C. (dec.).

IR (KBr): 3400, 2750–2200, 1690, 1590, 1450, 1320, 1180, 1125 cm$^{-1}$.

NMR (DMSO-d$_6$, δ): 1.57 (3H, d, J=7 Hz), 2.97 (6H, s), 3.47 (3H, s), 5.22 (1H, q, J=7Hz), 6.85 (2H, d, J=9 Hz), 7.15 (2H, d, J=9 Hz), 6.92 (1H, dd, J=2 Hz and 9 Hz), 7.05 (1H, d, J=2 Hz), 7.85 (1H, d, J=9 Hz).

(21) 6-[1-(Carboxy)cyclohexylmethoxy]-2-(4-chlorophenyl)-4-methyl-2H-1,2,4-benzothiadiazine-3(4H)-one 1,1-dioxide mp: 145°–150° C.

IR (Nujol): 3300, 1700, 1600, 1580, 1370, 1310, 1190, 1130 cm$^{-1}$.

NMR (CDCl$_3$, δ): 1.10–2.10 (11H, m), 3.40 (3H, s), 4.40 (1H, br s), 6.60 (1H, d, J=9 Hz), 6.85 (1H, s), 7.25 (2H, d, J=9 Hz), 7.42 (2H, d, J=9 Hz), 7.70 (1H, d, J=9 Hz).

EXAMPLE 17

To a solution of (1R)-(+)-2-(4-chlorophenyl)-6-(1-carboxyethoxy)-4-methyl-2H-1,2,4-benzothiadiazine-3(4H)-one 1,1-dioxide (250 mg) in acetonitrile (5 ml) was added a solution of sodium bicarbonate (51 mg) in water (1 ml) in one portion at ambient temperature. The mixture was concentrated in vacuo. The residue was recrystallized from a mixture of ethanol and acetonitrile to yield sodium salt of (1R)-(+)-2-(4-chlorophenyl)-6-(1-carboxyethoxy)-4-methyl-2H-1,2,4-benzothiadiazine-3(4H)-one, 1,1-dioxide (205 mg) as crystals.

mp: 225°–230° C.

[α]$_D$+8.34° (C=1.0, EtOH).

IR (Nujol): 3300, 1710, 1600, 1580, 1380, 1210, 1190, 1130 cm$^{-1}$.

NMR (DMSO-d$_6$, δ): 1.43 (3H, d, J=7 Hz), 3.45 (3H, s), 4.48 (1H, q, J=7 Hz), 6.80 (1H, dd, J=2 Hz and 9 Hz), 6.95 (1H, d, J=2 Hz), 7.42 (2H, d, J=9 Hz), 7.59 (2H, d, J=9 Hz), 7.77 (1H, d, J=9 Hz).

EXAMPLE 18

In a similar manner to that of EXAMPLE 17, there was obtained the following compound.

Sodium salt of (1S)-(−)-2-(4-chlorophenyl)-6-(1-carboxyethoxy)-4-methyl-2H-1,2,4-benzothiadiazine-3(4H)-one 1,1-dioxide mp: 210°–215° C.

[α]$_D$−8.53° (C=0.1, EtOH)

IR (Nujol): 3550, 3400, 1170, 1600, 1380, 1220, 1180, 1120 cm$^{-1}$.

NMR (DMSO-d$_6$, δ): 1.44 (3H, d, J=7 Hz), 3.45 (3H, s), 4.49 (1H, q, J=7 Hz), 6.81 (1H, dd, J=2 Hz and 9 Hz), 7.39 (1 H, d, J=2 Hz), 7.42 (2H, d, J=9 Hz), 7.59 2H, d, J=9 Hz), 7.77 (1H, d, J=9 Hz).

EXAMPLE 19

A mixture of 2-(4-carboxyphenyl)-6-hydroxy-4-methyl-2H-1,2,4-benzothiadiazine-3(4H)-one 1,1-dioxide (0.13 g), potassium carbonate (0.103 g) and bromomethylcyclohexane (0.14 g) in dry N,N-dimethylformamide (1.3 ml) was stirred at 80° C. for 16 hours. The cooled mixture was poured into diluted hydrochloric acid. The separated oil was extracted with diethyl ether. The organic layer was washed with water, aqueous sodium bicarbonate solution, and brine. The dried solvent was concentrated in vacuo to yield 6-cyclohexylmethoxy-2-(4-cyclohexyl-methoxycarbonylphenyl)-4-methyl-2H-1,2,4-benzothiadiazine-3(4H)-one 1,1-dioxide (0.13 g) as colorless crystals.

mp: 119°–121° C.

IR (Nujol): 1720, 1690, 1600, 1320 cm$^{-1}$.

NMR (DMSO-d$_6$, δ): 0.95–1.40 (10H, m), 1.55–1.95 (12H, m), 3.52 (3H, s), 4.00 (2H, d, J=5.8 Hz), 4.15 (2H, d, J=5.8 Hz), 6.97–7.10 (2H, m), 7.55 and 8.10 (4H, ABq, J=8.3 Hz), 7.87 (1H, d, J=8.7 Hz).

EXAMPLE 20

In a similar manner to that of

EXAMPLE 19, there were obtained the following compounds.

(1) 2-(4-Chlorophenyl)-4-methyl-6-(2-phthalimidoethoxy)-2H-1,2,4-benzothiadiazine-3(4H)-one 1,1-dioxide mp: 175°–180° C.

IR (Nujol): 1770, 1710, 1605, 1585 cm$^{-1}$.

NMR (DMSO-d$_6$, δ): 3.50 (3H, s), 4.0–4.1 (2H, m), 4.4–4.5 (2H, m), 6.95–7.05 (2H, m), 7.35–7.45 (2H, m), 7.55–7.56 (3H, m), 7.8–8.0 (4H, m).

(2) 6-[trans-4-(tert-Butoxycarbonylaminomethyl)-cyclohexylmethoxy]- 2-(4-chlorophenyl)-4-methyl-2H-1,2,4-benzothiadiazine-3(4H)-one 1,1-dioxide mp: 133°–136° C.

IR (Nujol): 3400, 1690, 1600, 1590, 1520, 1450, 1360, 1340, 1180 cm$^{-1}$.

NMR (DMSO-d$_6$, δ): 0.75–1.20 (4H, m), 1.40 (9H, s), 1.40–2.00 (6H, m), 2.73 (2H, t, J=6 Hz), 3.50 (3H, s), 3.98 (2H, d, J=7 Hz), 7.00 (1H, d, J=9 Hz), 7.08 (1H, s), 7.40 (2H, d, J=9 Hz), 7.60 (2H, d, J=9 Hz), 7.88 (1H, d, J=9 Hz).

(3) 2-(4-Chlorophenyl)-6-[1-(ethoxycarbonyl)cyclohexylmethoxyl]-4-methyl-2H-1,2,4-benzothiadiazine-3(4H)-one 1,1-dioxide mp: 128°–131° C.

IR (Nujol): 1730, 1690, 1600, 1590, 1380, 1180 cm$^{-1}$.

NMR (CDCl$_3$, δ): 1.30 (3H, t, J=8 Hz), 1.10–2.10 (11H, m), 3.52 (3H, s), 4.25 (2H, q, J=8 Hz), 4.50 (1H, d, J=5 Hz), 6.75 (1H, dd, J=2 Hz and 9 Hz), 6.82 (1H, d, J=2 Hz), 7.35 (2H, d, J=9 Hz), 7.45 (2H, d, J=9 Hz), 7.85 (1H, d, J=9 Hz).

(4) 2-(4-Chlorophenyl)-4-methyl-6-[2-(tetrahydro-2Hpyranyl)methoxy]-2H-1,2,4-benzothiadiazine-3(4H)-one 1,1-dioxide mp: >250° C.

IR (Nujol): 1700, 1600, 1580, 1490, 1340, 1320, 1190 cm$^{-1}$.

NMR (DMSO-d$_6$, δ): 1.20–1.90 (6H, m), 3.40–3.90 (3H, m), 3.50 (3H, s), 4.10 (2H, d, J=6 Hz), 7.00 (1H, dd, J=2 Hz and 9 Hz), 7.10 (1H, d, J=2 Hz), 7.40 (2H, d, J=9 Hz), 7.60 (2H, d, J=9 Hz), 7.86 (1H, d, J=9 Hz).

EXAMPLE 21

A solution of 2-(4-isopropoxycarbonylmethylphenyl)-6-isopropoxy-4-methyl-2H-1,2,4-benzothiadiazine-3(4H)-one 1,1-dioxide (95 mg) in a mixture of 1,4-dioxane (6 ml), water (2 ml) and conc. hydrochloric acid (1 ml) was refluxed for two hours. After the mixture was concentrated in vacuo, the residue was extracted two times with ethyl acetate. The combined organic layers were washed with water and brine, dried over MgSO$_4$. After the solvent was evaporated under reduced pressure, the crystalline residue was recrystallized from ethanol to yield 2-(4-carboxymethylphenyl)-6-isopropoxy-4-methyl-2H-1,2,4-benzothiadiazine-3(4H)-one 1,1-dioxide (61 mg) as pale yellow crystals.

mp: 232°–233° C.

IR (Nujol): 3600–2500, 1700, 1685, 1600 cm$^{-1}$.

NMR (DMSO-d$_6$, δ): 1.34 (6H, d, J=6.0 Hz), 3.49 (3H, s), 3.66 (2H, s), 4.8–5.0 (1H, m), 6.95–7.01 (2H, m), 7.30 and 7.40 (4H, ABq, J=8.0 Hz), 7.84 (1H, d, J=9.0 Hz).

EXAMPLE 22

In a similar manner to that of

EXAMPLE 21, there were obtained the following compounds.

(1) 2-(4-Carboxyphenyl)-6-isopropoxy-4-methyl-2H-1,2,4-benzothiadiazine-3(4H)-one 1,1-dioxide mp: 247.5°–248.5° C.

IR (Nujol): 3200–2400, 1690, 1605 cm$^{-1}$.

NMR (DMSO-d$_6$, δ): 1.34 (6H, d, J=6.0 Hz), 3.50 (3H, s), 4.80–5.0 (1H, m), 6.95–7.07 (2H, m), 7.51 and 8.09 (4H, ABq, J=8.3 Hz), 7.86 (1H, d, J=8.4 Hz), 13.3 (1H, br s).

(2) 2-(3-Carboxypropyl)-6-isopropoxy-4-methyl-2H-1,2,4-benzothiadiazine-3(4H)-one 1,1-dioxide mp: 150°–152° C.

IR (Nujol): 1710, 1690, 1600, 1580, 1470, 1380, 1100 cm$^{-1}$.

NMR (CDCl$_3$, δ): 1.38 (6H, d, J=6 Hz), 2.05 (2H, m), 2.43 (2H, t, J=7 Hz), 3.46 (3H, s), 3.98 (2H, t, J=7 Hz), 4.67 (1H, m), 6.67 (1H, d, J=2 Hz), 6.76 (1H, dd, J=2 Hz and 9 Hz), 7.76 (1H, d, J=9 Hz)

EXAMPLE 23

A solution of 6-cyclohexylmethoxy-2-(4-cyclohexylmethoxycarbonylphenyl)-4-methyl-2H-1,2,4-benzothiadiazine-3(4H)-one 1,1-dioxide (0.12 g) in a mixture of conc. hydrochloric acid (1 ml), water (2 ml) and 1,4-dioxane (8 ml) was refluxed overnight. The mixture was concentrated in vacuo. The residue was treated with a mixture of ethyl acetate and aqueous 1N sodium hydroxide solution. The precipitates were collected by filtration, washed with ethyl acetate and then dissolved in a mixture of ethyl acetate and aqueous 1N hydrochloric acid. The organic layer was washed with water, dried, and evaporated under reduced pressure. The residue was recrystallized from ethanol to give 2-(4-carboxyphenyl)-6-cyclohexylmethoxy-4-methyl-2H-1,2,4-benzothiadiazine-3(4H)-one 1,1-dioxide as colorless crystals.

mp: 240.5°–241° C.

IR (Nujol): 3300–2400, 1690, 1600, 1330 cm$^{-1}$.

NMR (DMSO-d$_6$, δ): 1.40–1.95 (5H, m), 1.55–1.95 (6H, m), 3.52 (3H, s), 4.00 (1H, d, J=5.8 Hz), 6.95–7.10 (2H, m), 7.50 and 8.05 (4H, ABq, J=8.3 Hz), 7.86 (1H, d, J=8.7 Hz), 13.3 (1H, br s)

EXAMPLE 24

To a solution of 2-(4-chlorophenyl)-4-methyl-6-(N-methylacetylamino)-2H-1,2,4-benzothiadiazine-3(4H)-one 1,1-dioxide (0.14 g) in ethanol (2.8 ml) was added conc. hydrochloric acid (2.8 ml). The mixture was refluxed for one hour and neutralized with aqueous saturated NaHCO$_3$ solution. The resulting crystals were collected by filtration to give 2-(4-chlorophenyl)-4-methyl-6-(N-methylamino)-2H-1,2,4-benzothiadiazine-3(4H)-one 1,1-dioxide (0.105 g) as colorless powder.

mp: 207°–209° C.

IR (Nujol): 3400, 1690, 1600, 1320 cm$^{-1}$.

NMR (CDCl$_3$, δ): 2.95 (3H, s), 3.51 (3H, s), 4.5 (1H, br), 6.28 (1H, br s), 6.4–6.5 (1H, m), 7.3–7.5 (4H, m), 7.62–7.7 (1H, m).

EXAMPLE 25

In a similar manner to that of

EXAMPLE 24, there was obtained the following compound.

Hydrochloride salt of 6-[trans-4-(aminomethyl)cyclohexylmethoxy]-2-(4-chlorophenyl)-4-methyl-2H-1,2,4-benzothiadiazine-3(4H)-one 1,1-dioxide mp: >250° C.

IR (Nujol): 3400, 1700, 1610, 1600, 1380, 1330, 1310, 1280, 1130 cm$^{-1}$.

NMR (DMSO-d$_6$, δ): 0.90–1.20 (4H, m), 1.40–2.10 (6H, m), 2.70 (2H, m), 3.50 (3H, s), 4.02 (2H, d, J=7 Hz), 7.03 (1H, dd, J=2 Hz and 9 Hz), 7.10 (1H, d, J=2 Hz), 7.40 (2H, d, J=9 Hz), 7.60 (2H, d, J=9 Hz), 7.90 (1H, d, J=9 Hz), 8.00 (1H, br s).

EXAMPLE 26

To a solution of 2-(4-chlorophenyl)-4-methyl-6-(2-phthalimidoethoxy)-2H-1,2,4-benzothiadiazine-3(4H)-one 1,1-dioxide (0.153 g) in methanol (1.5 ml) was added hydrazine monohydrate (30 mg). After the mixture was refluxed for one hour, the reaction mixture was treated with conc. HCl and further refluxed for 30 minutes. The precipitate was removed by filtration and the filtrate was washed two times with ether. The aqueous layer was treated with aqueous 1N NaOH solution and extracted with ethyl acetate. The extract was washed with brine and dried over MgSO$_4$. After the solvent was evaporated under reduced pressure, the residue was triturated with IPE. The colorless crystals were collected by filtration and recrystallized from ethanol to give 6-(2-aminoethoxy)-2-(4-chlorophenyl)-4-methyl-2H-1,2,4-benzothiadiazine-(3-(4H)-one 1,1-dioxide (30 mg) as colorless prisms.

mp: 175–176° C.

IR (Nujol): 3370, 3310, 1705, 1685, 1600, 1195 cm$^{-1}$.

NMR (CDCl$_3$, δ): 1.66 (2H, br s), 3.19 (2H, br s), 3.54 (3H, s), 4.12 (2H, t, J=5.0 Hz), 6.77–7.90 (2H, m), 7.35 and 7.46 (4H, ABq, J=8.5 Hz), 7.85 (1H, d, J=8.5 Hz)

EXAMPLE 27

Into a solution of 6-isopropoxy-4-methyl-2-(2-pyridyl)-2H-1,2,4-benzothiadiazine-3(4H)-one 1,1-dioxide (0.174 g) in chloroform (5 ml) was bubbled chlorine gas for a few minutes at 5° C. The mixture was washed with aqueous sodium bicarbonate solution, dried and concentrated in vacuo. The residue was crystallized from ethanol to yield 7-chloro-6-isopropoxy-4-methyl-2-(2-pyridyl)-2H-1,2,4-benzothiadiazine-3(4H)-one 1,1-dioxide (115 mg) as colorless needles.

mp: 193°–194° C.

IR (Nujol): 1685, 1590, 1345 cm$^{-1}$.

NMR (CDCl$_3$, δ): 1.46 (6H, d, J=6 Hz), 3.55 (3H, s), 4.6–4.85 (1H, m), 6.75 (1H, s), 7.35–7.55 (2H, m), 7.90 (1H, s), 7.85–7.95 (1H, m), 8.6–8.7 (1H, m).

EXAMPLE 28

In a similar manner to that of EXAMPLE 27, there was obtained the following compound. 7-Bromo-6-isopropoxy-4-methyl-2-(2-pyridyl)-2H-1,2,4-benzothiadiazine-3(4H)-one 1,1-dioxide mp: 194.5°–195.5° C.

NMR (CDCl$_3$, δ): 1.47 (6H, d, J=6 Hz), 3.55 (3H, s), 4.6–4.85 (1H, m), 6.71 (1H, s), 7.35–7.55 (2H, m), 7.85–7.95 (1H, m), 8.04 (1H, s), 8.60–8.70 (1H, m).

EXAMPLE 29

Into a suspension of 2-(4-chlorophenyl)-6-hydroxy-4-methyl-2H-1,2,4-benzothiadiazine-3(4H)-one 1,1-dioxide (700 mg) in acetic acid (70 ml) was bubbled chlorine gas to give the colorless solution at ambient temperature. The mixture was poured into an ice water. The precipitates was collected by filtration and recrystallized from ethanol to yield 2-(4-chlorophenyl)-5,7-dichloro-6-hydroxy-4-methyl-2H-1,2,4-benzothiadiazine(3(4H)-one 1,1-dioxide (350 mg) as crystals.

mp: 197°–198° C.

IR (Nujol): 1720, 1700, 1500, 1360, 1180 cm$^{-1}$.

NMR (DMSO-d$_6$, δ): 3.55 (3H, s), 7.42 (2H, d, J=9 Hz), 7.60 (2H, d, J=9 Hz), 8.00 (1H, s).

EXAMPLE 30

To a solution of 2-(4-chlorophenyl)-4-methyl-6-(N-methylamino)-2H-1,2,4-benzothiadiazine-3(4H)-one 1,1-dioxide (55 mg) in dry THF (2 ml) was added a 1.5M solution of n-butyl lithium in n-Hexane (0.16 ml) at −78° C. The mixture was stirred at 0° C. for 30 minutes and added methyl iodide (0.05 ml) at the same temperature. After the mixture was stirred at 0° C. for 30 minutes, water was added. The mixture was extracted two times with ethyl acetate and the combined organic layers were washed with water and brine and dried over MgSO$_4$. After the solvent was evaporated under reduced pressure, the residue was purified by preparative thin layer chromatography (eluted with a mixture of benzene and acetone (9:1) to give 2-(4-chlorophenyl)-6-(N,N-dimethylamino)-4-methyl-2H-1,2,4-benzothiadiazine-3(4H)-one 1,1-dioxide (8 mg) as colorless powder.

205°–206° C.

IR (Nujol): 1690, 1605 cm$^{-1}$.

NMR (CDCl$_3$, δ): 3.12 (6H, s), 3.54 (3H, s), 6.32 (1H, d, J=2.0 Hz), 6.56 (1H, dd, J=2.0 and 9.0 Hz), 7.35 and 7.45 (4H, ABq, J=8.8 Hz), 7.70 (1H, d, J=9.0 Hz).

EXAMPLE 31

A mixture of 6-hydroxy-4-methyl-2-(4-trifluoromethylphenyl)-2H-1,2,4-benzothiadiazine-3(4H)-one 1,1-dioxide (1.56 g), (S)-(−)-ethyl-2-[[(4-methylphenyl)sulfonyl]-oxy]propionate (1.37 g) and potassium carbonate (578 mg) in N,N-dimethylformamide (15.6 ml) was stirred at 60°–65° C. for one hour. The cooled mixture was filtered off and the filtrate was poured into a mixture of ice and 1N-hydrochloric acid. The precipitates were collected and dissolved in methylene chloride. The solution was dried and concentrated in vacuo. The residue was crystallized from diisopropyl ether to yield (1R)-(+)-6-[1-(ethoxycarbonyl)methoxy]-4-methyl-2-(4-trifluoromethylphenyl)-2H-1,2,4-benzothiadiazine-3(4H)-one 1,1-dioxide (1.58 g).

mp: 124°–125° C.

IR (Nujol): 1720, 1685, 1595, 1330, 1130, 1060 cm$^{-1}$.

NMR (CDCl$_3$, δ): 1.30 (3H, t, J=6 Hz), 1.70 (3H, d, J=6 Hz), 3.54 (3H, s), 4.26 (2H, q, J=6 Hz), 4.88 (1H, q, J=6 Hz), 6.75 (1H, dd, J=2 Hz and 8 Hz), 6.85 (1H, d, J=2 Hz), 7.55 (2H, d, J=8 Hz), 7.75 (2H, d, J=8 Hz), 7.84 (1H, d, J=8 Hz).

What we claim is:

1. A compound of the formula:

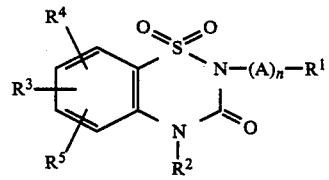

wherein R$^1$ is phenyl, pheny which is substituted with halogen, lower alkyl, alkoxy, halo lower alkyl, lower alkylamino, lower alkylthio, phenoxy, carboxy, lower alkoxycarbonyl, carboxy lower alkyl, lower alkoxycarbonyl lower alkyl, cyclo lower alkyl; lower alkyl which is substituted with carboxy or lower alkoxycabronyl; or pyrimidinyl, pyridyl or pyridyl which is substituted with lower alkyl;

A is lower alkylene;

n is an integer of 0 to 1;

R$^2$ is lower alkyl;

R$^3$ is hydrogen; hydroxy; halogen; halo lower alkyl; lower alkyl; lower alkylamino; lower alkanoyl amino; lower alkanoyl lower alkylamino; lower alkoxy; lower alkoxy which is substituted with phenyl, phthalimido, pyranyl, amino, carboxy, lower alkoxycarbonyl, cyclo lower alkyl or cyclo lower alkyl which is substituted with amino lower alkyl or lower alkoxycarbonylamino lower alkyl; or cyclo lower alkyloxy or cyclo lower alkyloxy which is substituted with carboxy or lower alkoxycarbonyl;

R$^4$ is hydrogen or halogen, and

R$^5$ is hydrogen or halogen, with the proviso that R$^1$ is phenyl substituted with lower alkoxy, lower alkylamino, lower alkylthio, phenoxy, carboxy, lower alkoxycarbonyl, carboxy lower alkyl or lower alkoxycarbonyl lower alkyl; lower alkyl or lower alkyl substituted with carboxy or lower alkoxycarbonyl; pyrimidinyl; pyridyl or pyridyl substituted with lower alkyl, when R$^3$ is hydrogen or halogen, or a pharmaceutically acceptable salt thereof.

2. The compound according to claim 1, wherein
$R^4$ and $R^5$ are both hydrogen, and
n is an integer of 0.
3. The compound according to claim 2, wherein
$R^1$ is phenyl, phenyl which is substituted with halogen, lower alkyl, lower alkoxy, halo lower alkyl, lower alkylamino, lower alkylthio, phenoxy, carboxy, lower alkoxycarbonyl, carboxy lower alkyl or lower alkoxycarbonyl lower alkyl, and
$R^3$ is lower alkoxy, lower alkoxy which is substituted with phenyl, phthalimido, pyranyl, amino, carboxy, lower alkoxycarbonyl, cyclo lower alkyl or cyclo lower alkyl which is substituted with amino lower alkyl or lower alkoxycarbonylamino lower alkyl.
4. The compound according to claim 3, wherein
$R^1$ is phenyl substituted with halogen, and
$R^3$ is lower alkoxy substituted with carboxy.
5. The compound of claim 4, which is
(1R)-(+)-2-(4-Chlorophenyl)-6-(1-carboxyethoxy)-4-methyl-2H-1,2,4-benzothiadiazine-3(4H)-one 1,1-dioxide or its salt.
6. A pharmaceutical composition comprising, as an active ingredient, one or more compounds of claim 1, or pharmaceutically acceptable salts thereof, and a pharmaceutically acceptable carrier or excipient.
7. A method for the treatment of bone diseases exhibiting abnormal bone metabolism in mammals by administering one or more compounds of claim 1, or pharmaceutically acceptable salts thereof to a mammal.

* * * * *